United States Patent [19]

Ayer et al.

[11] Patent Number: 5,502,187
[45] Date of Patent: Mar. 26, 1996

[54] PHARMACEUTICALLY ACTIVE BICYCLIC-HETEROCYCLIC AMINES

[75] Inventors: Donald E. Ayer, Kalamazoo; Gordon L. Bundy, Portage; Eric J. Jacobsen, Plainwell, all of Mich.

[73] Assignee: The Upjohn Company, Kalamazoo, Mich.

[21] Appl. No.: 317,934

[22] Filed: Oct. 3, 1994

Related U.S. Application Data

[63] Continuation-in-part of PCT/US93/02188, Mar. 16, 1993, which is a continuation-in-part of Ser. No. 863,646, Apr. 3, 1992, abandoned, and a continuation of Ser. No. 222,995, Apr. 5, 1994, abandoned, which is a continuation of Ser. No. 128,957, Sep. 29, 1993, abandoned.

[51] Int. Cl.⁶ .............................................. C07D 265/04
[52] U.S. Cl. ........................ 544/117; 544/61; 544/62; 544/127; 544/139; 544/143; 544/144; 544/244; 544/280; 544/336; 544/362; 544/370; 544/373; 546/23; 546/113; 546/118; 548/113; 548/304.4; 548/304.7; 548/306.1; 548/306.4; 548/306.7; 548/307.1; 548/309.4; 548/414; 548/415; 548/466; 548/484; 548/485; 548/486; 548/490; 548/491

[58] Field of Search ...................... 544/117, 127, 544/139, 143, 144, 244, 280, 61, 62, 336, 362, 370, 373; 546/23, 113, 118; 548/113, 304.4, 304.7, 306.1, 306.4, 306.7, 307.1, 309.4, 414, 415, 466, 484, 485, 486, 490, 491

[56] References Cited

U.S. PATENT DOCUMENTS

| | | | |
|---|---|---|---|
| 4,565,816 | 1/1986 | Neumann | 514/253 |
| 4,652,565 | 3/1987 | Neumann | 514/249 |
| 5,120,843 | 6/1992 | McCall et al. | 544/123 |
| 5,349,064 | 9/1994 | Akimoto et al. | 544/280 |
| 5,354,754 | 10/1994 | Akimoto et al. | 514/258 |
| 5,354,756 | 10/1994 | Underiner et al. | 514/263 |

FOREIGN PATENT DOCUMENTS

| | | |
|---|---|---|
| 92/132074 | 4/1992 | European Pat. Off. . |
| 0514540A1 | 11/1992 | European Pat. Off. . |
| 549886A1 | 7/1993 | European Pat. Off. . |
| 3318671 | 12/1983 | Germany . |
| 6220059 | 8/1994 | Japan . |
| 6220060 | 8/1994 | Japan . |
| 260741 | 8/1949 | Switzerland . |
| 864145 | 3/1961 | United Kingdom . |
| 1268772 | 3/1972 | United Kingdom . |
| 2163150A | 2/1986 | United Kingdom . |
| WO87/01706 | 3/1987 | WIPO . |
| WO87/07895 | 12/1987 | WIPO . |
| WO88/07527 | 10/1988 | WIPO . |
| 91/04254 | 4/1991 | WIPO . |
| WO91/06542 | 5/1991 | WIPO . |
| 92/02500A | 2/1992 | WIPO . |
| WO88/08424 | 6/1992 | WIPO . |
| 94/13676 | 6/1994 | WIPO . |
| 94/20459 | 9/1994 | WIPO . |

OTHER PUBLICATIONS

Kratritzky, A. R. and Rees, C. W., *Comprehensive and Heterocyclic Chemistry*, 4, p. 528 (1984).
*J. Chem. Soc.*, 101, 1779 (1912).
*Biochem. Z.*, 49, 182 (1913).
*J. Chem. Soc.*, 95, 1526, (1909).
CA 44, 2041b, 9–Aminoacridine and methyl derivative, Falk, 1950.
Eger et al., The *J. Heterocyclic. Chem.*, 24, 425 (1987).
Journal of Heterocyclic Chemistry, B, Venugopalan, et al., vol. 25, Provo US, pp. 1633–1639 (1988).

*Primary Examiner*—Joseph K. McKane
*Attorney, Agent, or Firm*—Bruce Stein

[57] ABSTRACT

The pharmaceutically active bicyclic heterocyclic amines (XXX)

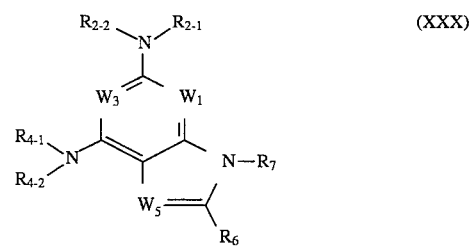

where $W_1$ is —N= or —CH=; $W_3$ is —N= or —CH=; $W_5$ is —N= or —CR$_5$— with the proviso that $W_5$ is —CR$_5$— when both $W_1$ and $W_3$ are —N= which are useful as pharmaceuticals in treating mild and/or moderate to severe head injury, subarachnoid hemorrhage and subsequent ischemic stroke, asthma and reduction of mucous formation/secretion in the lung and other diseases and injuries.

25 Claims, No Drawings

PHARMACEUTICALLY ACTIVE BICYCLIC-HETEROCYCLIC AMINES

CROSS-REFERENCE TO RELATED APPLICATIONS

The present patent application is a continuation-in-part (national phase) patent application of PCT patent application PCT/US93/02188, filed Mar. 16, 1993 which is a continuation-in-part patent application of U.S. patent application Ser. No. 07/863,646, filed Apr. 3, 1992, now abandoned and a continuation of U.S. patent application Ser. No. 08/222,995 filed Apr. 5, 1994 which is a continuation of U.S. patent application Ser. No. 08/128,957 filed Sep. 29, 1993, now abandoned.

BACKGROUND OF THE INVENTION

1. Field of the Invention

The pharmaceutically active bicyclic heterocyclic amines (XXX) of the present invention are useful as pharmaceuticals to treat a number of diseases and injuries.

2. Description of the Related Art

The bicyclic heterocyclic amines (XXX) of the present invention contain a variety of compounds depending on the definitions of $W_1$, $W_3$ and $W_5$.

When $W_1$ is —N=, $W_3$ is —N= and $W_5$ is —$CR_5$= the bicyclic heterocyclic amines (XXX) are pyrrolo[2,3-d])pyrimidines (VII). The pyrrolo[2,3-d]pyrimidine ring system is known. For example, 4-amino-7β-D-ribofuranosyl-7H-pyrrolo[2,3-d]pyrimidine is tubercidin. However, the 2,4-di(tertiary amino)-pyrrolo[2,3-d]pyrimidines of this invention are novel. Other similar compounds have been prepared for study of antiviral and antitumor properties, see Comprehensive Heterocyclic Chemistry, A. R. Katritzky and C. W. Roes, Ed., Vol. 4, Pergamon Press, 1984, p. 528.

When $W_1$ is —N=, $W_3$ is —CH= and $W_5$ is —N= the bicyclic heterocyclic amines (XXX) are 3H-imidazo[4,5b]pyridines (XXV). This ring system is known, see DE 3 318 671 A1, CA 44, 2041b and Swiss Patent 260,741.

When $W_1$ is —N=, $W_3$ is —CH= and $W_5$ is —$CR_5$= the bicyclic heterocyclic amines (XXX) are 1H-pyrrolo[2,3-b]pyridines (XI). This ring system is known, see *J. Chem. Soc.*, 101, 1779 (1912).

When $W_1$ is —CH=, $W_3$ is —N= and $W_5$ is —N= the bicyclic heterocyclic mines (XXX) are 1H-imidazo[4,5-c]pyridines (XXIX). This ring system is known, see *Biochem. Z*, 49, 182 (1913).

When $W_1$ is —CH=, $W_3$ is —N= and $W_5$ is —$CR_5$= the bicyclic heterocyclic amines (XXX) are 1H-pyrrolo[3,2-c]pyridines (XVI). This ring system is known, see *J. Chem. Soc.*, 95, 1526 (1909).

Other substituted amino type compounds which are useful for treating the same diseases and injuries as those of the present invention are disclosed in International Publication No. WO87/01706, published Mar. 26, 1987 based on International Patent Application No. PCT/US86/01797; International Publication No. WO87/07895, published Dec. 30, 1987 based on International Patent Application No. PCT/US87/07895; International Publication No. WO88/08424, published Nov. 3, 1988 based on International Patent Application No. PCT/US88/01212; International Publication No. WO88/07527, published Oct. 6, 1988 based on International Patent Application No. PCT/US88/00817 and U.S. patent application Ser. No. 07/427,143, filed Oct. 25, 1989.

WO92/02500-A discloses 2-phenylindole derivatives useful for treating asthma, allergic disorders, thrombosis and ischaemia.

The *J. Heterocyclic. Chem.*, 24, 425 (1987) [EGER] discloses pyrrolopyrimidines where the amino groups on the pyrimidine moiety are free and unsubstituted, whereas the compounds of the present invention are substituted aminopyrrolopyrimidines.

WO91/04254 discloses pyrrolo[2,3-d])pyrimidines where the groups substituted on the pyrrolo ring are simple. In two of the positions the groups are -H, halogen or alkyl. In the third it is -H, alkyl or aralkyl. The present invention requires that one of $R_5$ or $R_6$ is aromatic or heteroaromatic substituted.

*J. Heterocyclic Chem.*, 25, 1633 (1988) discloses pyrimido[4,5-b]indoles with an aromatic ring attached to the 5-member nitrogen containing ring which have antihypertensive activity.

Great Britain Patent 1,268,772 also discloses pyridinoindoles with an aromatic ring attached to the 5-member nitrogen containing ring. These compounds are reported to have antiviral activity in tissue culture experiments.

Great Britain Patent 864,145 discloses imidazolopyrimidines which have analgesic and coronary vasodilation effects.

European Patent 549,886 discloses pyrrolo(2,3-d)pyrimidines useful as anti-neoplastic agents which differ from the compounds of the present invention in that they do not have any substitutent at $C_6$ and do not include substituted amines for what is $R_1$ and $R_2$ of the present invention. Further, the compounds of European Patent 549,886 are prepared by a synthetic route quite different from the method of preparation of the compounds of the present invention.

European Patent 550,574 discloses amino substituted pyrrolopyrimidines useful for immunoregulation of autoimmune and other diseases. The bicyclic heterocyclic amines (XXX) of the present invention include pyrrolopyrimidines however, the pyrrolopyrimidines of the present invention must have the two amino groups on the pyrimidine ring substituted.

International Publication WO92/132074 (European Patent Application 550,574 A1) discloses amino substituted pyrrolopyrimidines useful for immunoregulation of autoimmune and other diseases (rheumatoid arthritis, multiple sclerosis, type I diabetes and viral diseases (HIV). The bicyclic heterocyclic amines (XXX) of the present invention include pyrrolopyrimidines however, the pyrrolopyrimidines of the present invention must have the two substituted amino groups on the pyrimidine ring. Further, the compounds of WO92/132074 do not permit aromatic substitution on the 5-member ring whereas the claimed invention requires aromatic substitution on the 5-membered ring.

International Publication WO 94/13676 (PCT/US9/10715) discloses pyrrolopyrimidines. The examples set forth indicate a strong preference for alkyl (methyl) attached between the pyrimidinyl nitrogen atoms whereas the claimed invention requires an amino group. These compounds were disclosed as being useful for treating depression and anxiety related disorders.

U.S. Pat. No. 5,249,064 discloses pyrrolopyrimidines where the amino substituent between the pyrimidine nitrogen atoms is unsubstituted and the other substituent on the pyrimidine is a amino, hydroxyl or mercapto group which are useful as antitumor agents. The claimed invention requires that the amino group located at the position between the pyrimidine nitrogen atoms be substituted.

U.S. Pat. No. 5,354,754 discloses pyrrolopyrimidines requires at least one of the amino groups on the pyrimidinyl ring to be unsubstituted amino. The present invention requires that both amino groups be substituted.

U.S. Pat. No. 5,354,756 discloses xanthine compounds lowers elevated blood levels of unsaturated, non-arachidonate phosphatic acid and diacylglycerols. The compounds of the present invention expressly prohibit four nitrogen atoms (xanthine ring system) and are useful for a totally different purpose.

International publication WO94/20459 discloses pyrrolopyridines where the substituent attached to the 3-position is piperidinyl or benzofuranyl. These substituents are not permitted in the corresponding position of the claimed invention.

UK Patent Application GB 2,163,150 discloses bicyclic heterocyclic compounds containing at least one nitrogen heteroatom and having a side chain containing an oxygen atom attached via a second oxygen atom to the six member ring. The present invention does not permit the side chain to be attached by an oxygen atom.

JP 6-220,059 discloses [3,2-d]pyrrolopyrimidinyl compounds useful as blood sugar lowering agents whereas the claimed compounds are [2,3-d]pyrrolopyrimidinyl compounds.

JP 6-220,060 discloses bicyclic pyrimidinyl compounds where the substitutents on the pyrimidinyl ring are amino, hydroxy and thio useful as anti-tumor agents whereas the claimed compounds expressly prohibit unsubstituted amino, hydroxy and thio.

SUMMARY OF INVENTION

Disclosed are bicyclic heterocyclic amines of the formula (XXX)

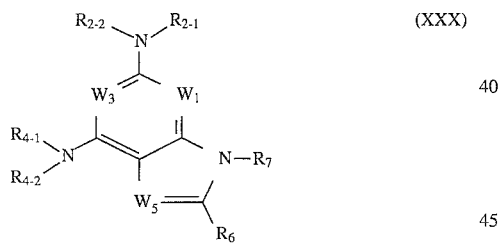

where
$W_1$ is —N═ or —CH═;
$W_3$ is —N═ or —CH═;
$W_5$ is —N═ or —CR$_5$— with the proviso that $W_5$ is —CR$_5$— when both $W_1$ and $W_3$ are —N═;
where
$R_5$ is
($C_5$-1)
(A) —H,
($C_5$-2)
(B) $C_1$–$C_8$ alkyl optionally substituted with 1 thru 4 $R_{5-1}$ where $R_{5-1}$ is
  (1) —F, —Cl, —Br,
  (2) $C_1$–$C_4$ alkyl,
  (3) —CF$_3$,
  (4) -φ,
  (5) —OR$_{5-2}$ where $R_{5-2}$ is
    (a) —H,
    (b) $C_1$–$C_4$ alkyl,
    (c) phosphate,
    (d) sulfate,
    (e) —CO—R$_{5-8}$ where R$_{5-8}$ is $C_1$–$C_4$ alkyl or $C_6$–$C_9$ aralkyl,
    (f) —CO—NR$_{5-10}$R$_{5-11}$ where R$_{5-10}$ and R$_{5-11}$ are the same or different and are —H or $C_1$–$C_3$ alkyl,
    (g) sulfamate,
    (h) glucosyl,
    (i) galactosyl,
    (j) glucuronic acid,
    (k) maltosyl,
    (l) arabinosyl,
    (m) xylosyl,
    (n) —CO—CH(NH$_2$)—H,
    (o) —CO—CH(NH$_2$)—CH$_3$,
    (p) —CO—CH(NH$_2$)—CH(CH$_3$)$_2$,
    (q) —CO—CH(NH$_2$)—CH$_2$—CH(CH$_3$)$_2$,
    (r) —CO—CH(NH$_2$)—CH(CH$_3$)—CH$_2$—CH$_3$,
    (s) —CO—CH(NH$_2$)—CH$_2$—OH,
    (t) —CO—CH(NH$_2$)—CH(OH)—CH$_3$,
    (u) —CO—CH(NH$_2$)—CH$_2$-φ,
    (v) —CO—CH(NH$_2$)—CH$_2$-[p-phenyl]—OH,
    (w) —CO—CH(NH$_2$)—CH$_2$-[2-indolyl]
    (x) —CO—CH(NH$_2$)—CH$_2$—SH,
    (y) —CO—CH(NH$_2$)—CH$_2$—CH$_2$—S—CH$_3$,
    (z) —CO—CH—NH—CH$_2$—CH$_2$—C*H$_2$ where the carbon atoms marked with an "*" are bonded together to form a heterocyclic ring,
    (aa) —CO—C*H—NH—CH$_2$—CH(OH)—C*H$_2$ where the carbon atoms marked with an "*" are bonded together to form a heterocyclic ring,
    (bb) —CO—CH(NH$_2$)—CH$_2$—COOH,
    (cc) —CO—CH(NH$_2$)—CH$_2$—CONH$_2$,
    (dd) —CO—CH(NH$_2$)—CH$_2$—CH$_2$—COOH,
    (ee) —CO—CH(NH$_2$)—CH$_2$—CH$_2$—CONH$_2$,
    (ff) —CO—CH(NH$_2$)—CH$_2$—C*—NH—CH═N—C*H═ where the carbon atoms marked with an "*" are bonded together to form a heterocyclic ring,
    (gg) —CO—CH(NH$_2$)—CH$_2$—CH$_2$—CH$_2$—NH—C(═NH)—NH$_2$,
    (hh) —CO—CH(NH$_2$)—CH$_2$—CH$_2$—CH$_2$—CH$_2$—NH$_2$,
    (ii) —CO—CH(NH$_2$)—CH$_2$—CH$_2$—CH(OH)—CH$_2$—NH$_2$,
    (jj) —CO—CH$_2$—CH$_2$—NH$_2$,
    (kk) —CO—CH$_2$—CH$_2$—CH$_2$—NH$_2$,
    (ll) —CO—CH(NH$_2$)—CH$_2$—CH$_2$—CH$_2$—NH$_2$,
    (mm) —CO—CH(NH$_2$)—CH$_2$—CH$_2$—CH$_2$—NH—CO—NH$_2$,
    (nn) —CO—CH(NH$_2$)—CH$_2$—CH$_2$—OH,
  (6) —SR$_{5-2}$ where R$_{5-2}$ is defined above,
  (7) —NHR$_{5-3}$ where R$_{5-3}$ is —H or $C_1$–$C_4$ alkyl,
  (8) —NR$_{5-4}$R$_{5-5}$ where R$_{5-4}$ and R$_{5-5}$ are the same or different and are $C_1$–$C_4$ alkyl or may taken together with the attached nitrogen atom to form the heterocyclic ring —N*—(CH$_2$)$_{n1}$—R$_{5-6}$—(CH$_2$)$_{n2}$* where the atoms marked with an asterisk (*) are bonded together resulting in the formation of a ring, where $n_1$ is 1 thru 5, $n_2$ is 0 thru 3 and R$_{5-6}$ is
    (a) —CH$_2$—,
    (b) —O—,
    (c) —S—,
    (d) —NR$_{5-9}$ where R$_{5-9}$ is
      (i) $C_1$–$C_6$ alkyl optionally substituted with 1 thru 3 —OH or —OCH$_3$,
      (ii) $C_1$–$C_6$ alkylcarbonyl,
      (iii) $C_1$–$C_6$ alkoxycarbonyl, (iv) $C_6-C_{12}$ arylalkyl,
(v) -φ,
(vi) $-SO_2-C_1-C_8$ alkyl,
(vii) $CH_3-C^*-O-CO-O-C^*-CH_2-$ where the carbon atoms designated by * are attached by a double bond to form a five member ring,
(9) $-(CH_2)_{n3}CO_2R_{5-2}$, where $n_3$ is 0 thru 6 and $R_{5-2}$ is as defined above,
(10) $-(CH_2)_{n3}CON(R_{5-3})_2$ where $n_3$ is as defined as above and where $R_{5-3}$ may be the same or different and is defined above,
(11) $-(CH_2)_{n3}CONR_{5-4}R_{5-5}$ where $n_3$, $R_{5-4}$, $R_{5-5}$ are as defined above,
(12) $-(CH_2)_{n1}OR_{5-2}$ where $R_{5-2}$ and $n_1$ are as defined above,
(13) $-(CH_2)_{n1}OCOR_{5-3}$ where $R_{5-3}$ and $n_1$ are as defined above,
(14) $-(CH_2)_{n1}SR_{5-2}$ where $R_{5-2}$ and $n_1$ are as defined above,
(15) $-(CH_2)_{n1}NHR_{5-3}$ where $R_{5-3}$ and $n_1$ are as defined above,
(16) $-(CH_2)_{n1}NR_{5-4}R_{5-5}$ where $R_{5-4}$, $R_{5-5}$, and $n_1$ are as defined above,
($C_5$-3)
(C) $-(CH_2)_{n3}$-φ optionally substituted with 1 thru 4 $R_{5-1}$ where $R_{5-1}$ and $n_3$ are as defined as above,
(D) $-(CH_2)_{n3}$-pyridin-2-, 3- or 4-yl optionally substituted with 1 thru 4 $R_{5-1}$ where $n_3$ and $R_{5-1}$ are as defined above,
(E) $-(CH_2)_{n3}$-naphthalin-1-, 2-yl optionally substituted with 1 thru 4 $R_{5-1}$ where $n_3$ and $R_{5-1}$ are as defined above,
($C_5$-5)
(F) $-(CH_2)_{n3}CO_2R_{5-2}$ where $n_3$ and $R_{5-2}$ are as defined above,
($C_5$-6)
(G) $-(CH_2)_{n3}CON(R_{5-3})_2$ where $n_3$ is as defined as above and where $R_{5-3}$ may be the same or different and is as defined above,
($C_5$-7)
(H) $-(CH_2)_{n3}CONR_{5-4}R_{5-5}$ where $n_3$, $R_{5-4}$, $R_{5-5}$ are as defined above,
($C_5$-8)
(I) $-(CH_2)_{n3}SO_3R_{5-2}$ where $n_3$ and $R_{5-2}$ are as defined above,
($C_5$-9)
(J) $-C_3-C_7$ cycloalkyl;
where
$R_{2-1}$ is
(A) $-H$,
(B) $C_1-C_8$ alkyl optionally substituted with 1 thru 4
(1) $-F$,
(2) $-Cl$,
(3) $-OR_{5-2}$ where $R_{5-2}$ is as defined above,
(4) $-N(R_{5-9})_2$ where $R_{5-9}$ may be the same or different and is as defined above;
where
$R_{2-2}$ is
(A) $-H$,
(B) $C_1-C_8$ alkyl optionally substituted with 1 thru 4
(1) $-F$,
(2) $-Cl$,
(3) $-OR_{5-2}$ where $R_{5-2}$ is as defined above,
(4) $-N(R_{5-9})_2$ where $R_{5-9}$ may be the same or different and is as defined above, or $R_{2-1}$ and $R_{2-2}$ are taken together with the attached nitrogen atom to form a heterocyclic ring selected from the group consisting of (A) 1-pyrrolidinyl optionally substituted on carbon with 1 thru 3 $R_{2-3}$ where $R_{2-3}$ is selected from the group of
(1) $C_1-C_6$ alkyl optionally substituted with 1 thru 3 $-OH$ or $-OCH_3$,
(2) $C_1-C_6$ alkenyl optionally substituted with 1 thru 3 $-OH$ or $-OCH_3$,
(3) $C_1-C_6$ alkylcarbonyl,
(4) $C_1-C_6$ alkoxycarbonyl,
(5) $C_6-C_{12}$ arylalkyl,
(6) $=O$,
(7) $-OH$,
(8) $-C\equiv N$,
(9) $-CO_2R_{2-4}$ where $R_{2-4}$ is
  (a) $-H$,
  (b) $C_1-C_4$ alkyl,
  (c) $C_6-C_{12}$ aryl,
  (d) $C_6-C_{12}$ aralkyl,
(10) $-NH_2$,
(11) $-Cl$,
(12) $-F$,
(13) $-Br$,
(14) -φ optionally substituted with 1 thru 3 $-F$, $-Cl$, $-Br$, $-OH$, $-OCH_3$, $-OCH_2$-φ, $-NO_2$, $C_1-C_3$ alkyl, $-NH_2$, $-NHCH_3$, $N(CH_3)_2$, $-CO_2R_{2-4}$ where $R_{2-4}$ is as defined above,
(15) $-(CH_2)_{n4}NR_{2-6}R_{2-7}$ where $R_{2-6}$ and $R_{2-7}$ are the same or different and $C_1-C_4$ alkyl or may taken together with the attached nitrogen atom to form the heterocyclic ring $-N^*-(CH_2)_{n5}-R_{2-8}-(CH_2)_{n6}$ * where the atoms marked with an asterisk (*) are bonded together resulting in the formation of a ring, where $n_4$ is 0 thru 3, $n_5$ is 1 thru 5, $n_6$ is 0 thru 3 and $R_{2-8}$ is
  (a) $-CH_2-$,
  (b) $-O-$,
  (c) $-S-$,
  (d) $-NR_{2-4}$ where $R_{2-4}$ is as defined above,
(B) 1-piperdinyl optionally substituted on carbon with 1 thru 3 $R_{2-3}$ where $R_{2-3}$ is as defined above,
(C) 1-morpholinyl optionally substituted on carbon with 1 thru 3 $R_{2-3}$ where $R_{2-3}$ is as defined above,
(D) 1-piperazinyl optionally substituted on carbon with 1 thru 3 $R_{2-3}$ where $R_{2-3}$ is as defined above and optionally substituted in the 4-position with $R_{2-5}$ where $R_{2-5}$ is
(1) $C_1-C_6$ alkyl optionally substituted with 1 thru 3 $-OH$ or $-OCH_3$,
(2) $C_1-C_6$ alkylcarbonyl,
(3) $C_1-C_6$ alkoxycarbonyl,
(4) $C_6-C_{12}$ arylalkyl,
(5) -φ,
(6) $-SO_2-C_1-C_8$ alkyl,
(7) $CH_3-C^*-O-CO-O-C^*-CH_2-$ where the carbon atoms designated by * are attached by a double bond to form a five member ring,
(E) 1-aziridinyl optionally substituted on carbon with 1 thru 2 $R_{2-3}$ where $R_{2-3}$ is as defined above,
(F) 1-azetidinyl optionally substituted on carbon with 1 thru 3 $R_{2-3}$ where $R_{2-3}$ is as defined above,
(G) 1-hexamethyleneimino optionally substituted on carbon with 1 thru 3 $R_{2-3}$ where $R_{2-3}$ is as defined above,
(H) 1-pyrrolyl optionally substituted on carbon with 1 thru 3 $R_{2-3}$ where $R_{2-3}$ is as defined above, (I) 1-imidazolyl optionally substituted on carbon with 1 thru 3 $R_{2-3}$ where $R_{2-3}$ is as defined above, (J) 1-pyrazoyl optionally substituted on carbon with 1 thru 3 $R_{2-3}$ where $R_{2-3}$ is as defined above, (K) 1-pyrazolidinyl optionally substituted on carbon with 1 thru 3 $R_{2-3}$ where $R_{2-3}$ is as defined above, (L) 1,2,3-triazolyl optionally substituted on carbon with 1 thru 3 $R_{2-3}$ where $R_{2-3}$ is as defined above, (M) 1,2,4-triazolyl optionally substituted on carbon with 1 thru 3 $R_{2-3}$ where $R_{2-3}$ is as defined above, (N) 1-tetrazolyl optionally substituted on carbon with 1 thru 3 $R_{2-3}$ where $R_{2-3}$ is as defined above, (O) 1-thiomorpholinyl optionally substituted on carbon with 1 thru 3 $R_{2-3}$ where $R_{2-3}$ is as defined above, (P) 1-thiazolidinyl, optionally substituted on carbon with 1 thru 3 $R_{2-3}$ where $R_{2-3}$ is as defined above,

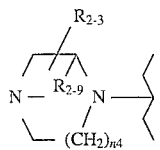 (Q)($R_{2-1}$/$R_{2-2}$-1)

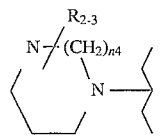 (R)($R_{2-1}$/$R_{2-2}$-2)

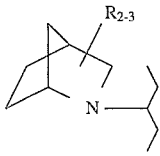 (S)($R_{2-1}$/$R_{2-2}$-3)

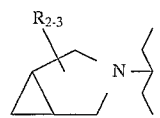 (T)($R_{2-1}$/$R_{2-2}$-4)

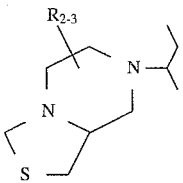 (U)($R_{2-1}$/$R_{2-2}$-5)

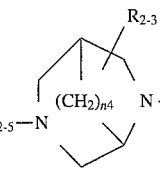 (V)($R_{2-1}$/$R_{2-2}$-6)

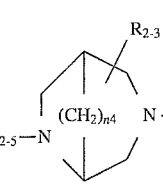 (W)($R_{2-1}$/$R_{2-2}$-7)

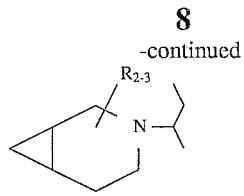 (X)($R_{2-1}$/$R_{2-2}$-8)

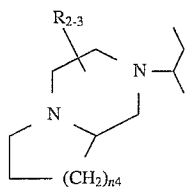 (Y)($R_{2-1}$/$R_{2-2}$-9)

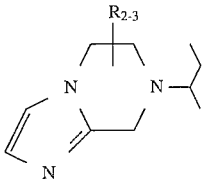 (Z)($R_{2-1}$/$R_{2-2}$-10)

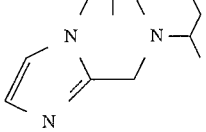 (AA)($R_{2-1}$/$R_{2-2}$-11)

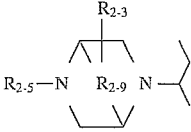 (BB)($R_{2-1}$/$R_{2-2}$-12)

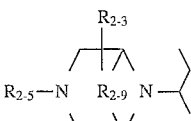 (CC)($R_{2-1}$/$R_{2-2}$-13)

where
$R_{2-3}$ and $R_{2-5}$ are as defined above,
where
$R_{2-9}$ is
(A) —$(CH_2)_{n4}$ where $n_4$ is 1 thru 3,
(B) —$CH_2OCH_2$,
(C) —$CH_2SCH_2$,
(D) —$CH_2SO_2CH_2$,
(E) —$CH_2S$,
(F) —$CH_2SO_2$,
(G) —$CH_2N(R_{2-5})CH_2$ where $R_{2-5}$ is as defined above, with the proviso that $R_{2-1}$ and $R_{2-2}$ can not both be —H;
where $R_{4-1}$ is defined the same as $R_{2-1}$, but may be the same or different than $R_{2-1}$,
where $R_{4-2}$ is defined the same as $R_{2-2}$, but may be the same or different than $R_{2-2}$, with the proviso that $R_{4-1}$ and $R_{4-2}$ can not both be —H;
where ($R_6$-1) $R_6$ is defined the same as $R_5$, but may be the same or different than $R_5$, with the proviso that:
(I) one of $R_5$, $R_6$ or $R_7$ must be selected from the group consisting of
($C_5$-3)
(C) —$(CH_2)_{n3}$-φ optionally substituted with 1 thru 4 $R_{5-1}$ where $R_{5-1}$ and $n_3$ as defined as above,
(D) —$(CH_2)_{n3}$-pyridin-2-, 3- or 4-yl optionally substituted with 1 thru 4 $R_{5-1}$ where $n_3$ and $R_{5-1}$ are as defined above, (E) —$(CH_2)_{n3}$-naphthalin-1-, 2-yl optionally substituted with 1 thru 4 $R_{5\text{-}1}$ where $n_3$ and $R_{5\text{-}1}$ are as defined above, and (II) for at least one of these three aromatic substituents, $n_3$ must be 0;

where $R_7$ is defined the same as $R_5$, but may be the same or different than $R_5$; with the proviso that $W_1$ and $W_3$ can not both be —CH=, and pharmaceutically acceptable salts thereof.

Also disclosed are bicyclic heterocyclic amines of the formula (XXX)

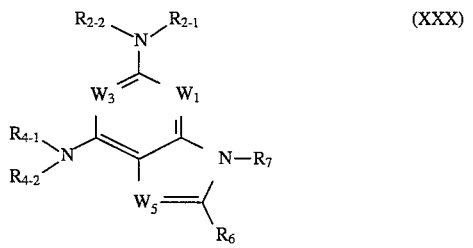

where $W_1$ is —N=;

$W_3$ is —N=;

$W_5$ is —$CR_5$—;

($R_6$-2) where $R_5$ and $R_6$ are taken together with the attached carbon atoms to form a ring selected from the group consisting of ($R_6$-2A)

—C*—$(CH_2)_{n7}$—C*  - where the carbon atoms marked by an asterick (*) are the carbon atoms in the 5-member nitrogen containing ring which are bonded together by the double bond (C=C), where $n_7$ is 3–5, and ($R_6$-2B)

—C*—$CR_{56\text{-}1}$=$CR_{56\text{-}2}$—$CR_{56\text{-}3}$=$CR_{56\text{-}4}$—C*  - where the carbon atoms marked by an asterick (*) are the carbon atoms in the 5-member nitrogen containing ring which are bonded together by the double bond (C=C), where $R_{56\text{-}1}$, $R_{56\text{-}2}$, $R_{56\text{-}3}$ and $R_{56\text{-}4}$ are —H, —F, —Cl, —Br, —OH, —$NO_2$, $C_1$-$C_3$ alkyl, —$NH_2$, —$NHCH_3$, $N(CH_3)_2$, —$CO_2R_{56\text{-}5}$ where $R_{56\text{-}5}$ is:

—H, $C_1$-$C_4$ alkyl, $C_6$-$C_{12}$ aryl, $C_6$-$C_{12}$ aralkyl;

where $R_{2\text{-}1}$ is (A) —H, (B) $C_1$-$C_8$ alkyl optionally substituted with 1 thru 4
(1) —F,
(2) —Cl,
(3) —$OR_{2\text{-}10}$ where $R_{2\text{-}10}$ is
  (a) —H,
  (b) $C_1$-$C_4$ alkyl,
  (c) phosphate,
  (d) sulfate,
  (e) —CO—$R_{2\text{-}11}$ where $R_{2\text{-}11}$ is $C_1$-$C_4$ alkyl or $C_6$-$C_9$ aralkyl,
  (f) —CO—$NR_{2\text{-}12}R_{2\text{-}13}$ where $R_{2\text{-}12}$ and $R_{2\text{-}13}$ are the same or different and are —H or $C_1$-$C_3$ alkyl,
  (g) sulfamate,
  (h) glucosyl,
  (i) galactosyl,
  (j) glucuronic acid,
  (k) maltosyl,
  (l) arabinosyl,
  (m) xylosyl,
  (n) —CO—CH($NH_2$)—H,
  (o) —CO—CH($NH_2$)—$CH_3$,
  (p) —CO—CH($NH_2$)—CH($CH_3$)$_2$,
  (q) —CO—CH($NH_2$)—$CH_2$—CH($CH_3$)$_2$,
  (r) —CO—CH($NH_2$)—CH($CH_3$)—$CH_2$—$CH_3$,
  (s) —CO—CH($NH_2$)—$CH_2$—OH,
  (t) —CO—CH($NH_2$)—CH(OH)—$CH_3$,
  (u) —CO—CH($NH_2$)—$CH_2$-φ,
  (v) —CO—CH($NH_2$)—$CH_2$-[p-phenyl]—OH,
  (w) —CO—CH($NH_2$)—$CH_2$-[2-indolyl]
  (x) —CO—CH($NH_2$)—$CH_2$—SH,
  (y) —CO—CH($NH_2$)—$CH_2$—$CH_2$—S—$CH_3$,
  (z) —CO—C*H—NH—$CH_2$—$CH_2$—C*$H_2$ where the carbon atoms marked with an "*" are bonded together to form a heterocyclic ring,
  (aa) —CO—C*H—NH—$CH_2$—CH(OH)—C*$H_2$ where the carbon atoms marked with an "*" are bonded together to form a heterocyclic ring,
  (bb) —CO—CH($NH_2$)—$CH_2$—COOH
  (cc) —CO—CH($NH_2$)—$CH_2$—$CONH_2$,
  (dd) —CO—CH($NH_2$)—$CH_2$—$CH_2$—COOH,
  (ee) —CO—CH($NH_2$)—$CH_2$—$CH_2$—$CONH_2$,
  (ff) —CO—CH($NH_2$)—$CH_2$—C*—NH—CH=N—C*H= where the carbon atoms marked with an "*" are bonded together to form a heterocyclic ring,
  (gg) —CO—CH($NH_2$)—$CH_2$—$CH_2$—$CH_2$—NH—C(=NH)—$NH_2$,
  (hh) —CO—CH($NH_2$)—$CH_2$—$CH_2$—$CH_2$—$CH_2$—$NH_2$,
  (ii) —CO—CH ($NH_2$)—$CH_2$—$CH_2$—CH(OH)—$CH_2$—$NH_2$,
  (jj) —CO—$CH_2$—$CH_2$—$NH_2$,
  (kk) —CO—$CH_2$—$CH_2$—$CH_2$—$NH_2$,
  (ll) —CO—CH($NH_2$)—$CH_2$—$CH_2$—$CH_2$—$NH_2$,
  (mm) —CO—CH($NH_2$)—$CH_2$—$CH_2$—$CH_2$—NH—CO—$NH_2$,
  (nn) —CO—CH($NH_2$)—$CH_2$—$CH_2$—OH,
(4) —N($R_{2\text{-}14}$)$_2$ where $R_{2\text{-}14}$ may be the same or different and is
  (a) $C_1$-$C_6$ alkyl optionally substituted with 1 thru 3 —OH or —$OCH_3$,
  (b) $C_1$-$C_6$ alkylcarbonyl,
  (c) $C_1$-$C_6$ alkoxycarbonyl,
  (d) $C_6$-$C_{12}$ arylalkyl,
  (e) -φ,
  (f) —$SO_2$—$C_1$-$C_8$ alkyl,
  (g) $CH_3$—C*—O—CO—O—C*—$CH_2$— where the carbon atoms marked by an asterick (*) are attached by a double bond to form a five member ring,
where
$R_{2\text{-}2}$ is
(A) —H,
(B) $C_1$-$C_8$ alkyl optionally substituted with 1 thru 4
(1) —F,
(2) —Cl,
(3) —$OR_{2\text{-}10}$ where $R_{2\text{-}10}$ is as defined above,
(4) —N($R_{2\text{-}14}$)$_2$ where $R_{2\text{-}14}$ may be the same or different and is as defined above, or $R_{2\text{-}1}$ and $R_{2\text{-}2}$ are taken together with the attached nitrogen atom to form a heterocyclic ring selected from the group consisting of (A) 1-pyrrolidinyl optionally substituted on carbon with 1 thru 3 $R_{2\text{-}3}$ where $R_{2\text{-}3}$ is selected from the group of (1) $C_1$-$C_6$ alkyl optionally substituted with 1 thru 3 —OH or —OCH$_3$,
(2) $C_1$-$C_6$ alkenyl optionally substituted with 1 thru 3 —OH or —OCH$_3$,
(3) $C_1$-$C_6$ alkylcarbonyl,
(4) $C_1$-$C_6$ alkoxycarbonyl,
(5) $C_6$-$C_{12}$ arylalkyl,
(6) =O,
(7) —OH,
(8) —C≡N,
(9) —CO$_2$R$_{2-4}$ where R$_{2-4}$ is
 (a) —H,
 (b) $C_1$-$C_4$ alkyl,
 (c) $C_6$-$C_{12}$ aryl,
 (d) $C_6$-$C_{12}$ aralkyl,
(10) —NH$_2$,
(11) —Cl,
(12) —F,
(13) —Br,
(14) -φ optionally substituted with 1 thru 3 —F, —Cl, —Br, —OH, —OCH$_3$, —OCH$_2$-φ, —NO$_2$, $C_1$-$C_3$ alkyl, —NH$_2$, —NHCH$_3$, N(CH$_3$)$_2$, —CO$_2$R$_{2-4}$ where R$_{2-4}$ is as defined above,
(15) —(CH$_2$)$_{n4}$NR$_{2-6}$R$_{2-7}$ where R$_{2-6}$ and R$_{2-7}$ are the same or different and are $C_1$-$C_4$ alkyl or may taken together with the attached nitrogen atom to form the heterocyclic ring —N*—(CH$_2$)$_{n5}$—R$_{2-8}$—(CH$_2$)$_{n6}$* where the atoms marked with an asterisk (*) are bonded together resulting in the formation of a ring, where $n_4$ is 0 thru 3, $n_5$ is 1 thru 5, $n_6$ is 0 thru 3 and R$_{2-8}$ is
 (a) —CH$_2$—,
 (b) —O—,
 (c) —S—,
 (d) —NR$_{2-4}$ where R$_{2-4}$ is as defined above,
(B) 1-piperdinyl optionally substituted on carbon with 1 thru 3 R$_{2-3}$ where R$_{2-3}$ is as defined above,
(C) 1-morpholinyl optionally substituted on carbon with 1 thru 3 R$_{2-3}$ where R$_{2-3}$ is as defined above,
(D) 1-piperazinyl optionally substituted on carbon with 1 thru 3 R$_{2-3}$ where R$_{2-3}$ is as defined above and optionally substituted in the 4-position with R$_{2-5}$ where R$_{2-5}$ is
 (1) $C_1$-$C_6$ alkyl optionally substituted with 1 thru 3 —OH or —OCH$_3$,
 (2) $C_1$-$C_6$ alkylcarbonyl,
 (3) $C_1$-$C_6$ alkoxycarbonyl,
 (4) $C_6$-$C_{12}$ arylalkyl,
 (5) -φ,
 (6) —SO$_2$—$C_1$-$C_8$ alkyl,
 (7) CH$_3$—C*—O—CO—O—C*—CH$_2$— where the carbon atoms marked by an asterick (*) are attached by a double bond to form a five member ring,
(E) 1-aziridinyl optionally substituted on carbon with 1 thru 2 R$_{2-3}$ where R$_{2-3}$ is as defined above,
(F) 1-azetidinyl optionally substituted on carbon with 1 thru 3 R$_{2-3}$ where R$_{2-3}$ is as defined above,
(G) 1-hexamethyleneimino optionally substituted on carbon with 1 thru 3 R$_{2-3}$ where R$_{2-3}$ is as defined above,
(H) 1-pyrrolyl optionally substituted on carbon with 1 thru 3 R$_{2-3}$ where R$_{2-3}$ is as defined above,
(I) 1-imidazolyl optionally substituted on carbon with 1 thru 3 R$_{2-3}$ where R$_{2-3}$ is as defined above,
(J) 1-pyrazoyl optionally substituted on carbon with 1 thru 3 R$_{2-3}$ where R$_{2-3}$ is as defined above,
(K) 1-pyrazolidinyl optionally substituted on carbon with 1 thru 3 R$_{2-3}$ where R$_{2-3}$ is as defined above,
(L) 1,2,3-triazolyl optionally substituted on carbon with 1 thru 3 R$_{2-3}$ where R$_{2-3}$ is as defined above,
(M) 1,2,4-triazolyl optionally substituted on carbon with 1 thru 3 R$_{2-3}$ where R$_{2-3}$ is as defined above,
(N) 1-tetrazolyl optionally substituted on carbon with 1 thru 3 R$_{2-3}$ where R$_{2-3}$ is as defined above,
(O) 1-thiomorpholinyl optionally substituted on carbon with 1 thru 3 R$_{2-3}$ where R$_{2-3}$ is as defined above,
(P) 1-thiazolidinyl, optionally substituted on carbon with 1 thru 3 R$_{2-3}$ where R$_{2-3}$ is as defined above,

(Q)(R$_{2-1}$/R$_{2-2}$-1)

(R)(R$_{2-1}$/R$_{2-2}$-2)

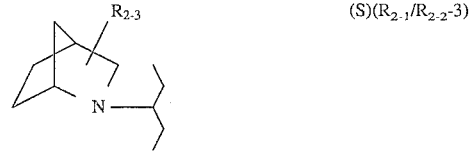
(S)(R$_{2-1}$/R$_{2-2}$-3)

(T)(R$_{2-1}$/R$_{2-2}$-4)

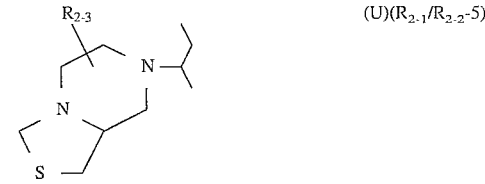
(U)(R$_{2-1}$/R$_{2-2}$-5)

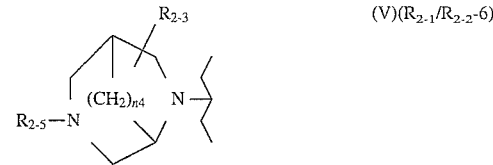
(V)(R$_{2-1}$/R$_{2-2}$-6)

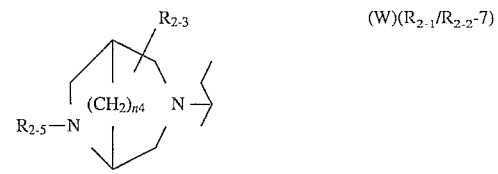
(W)(R$_{2-1}$/R$_{2-2}$-7)

-continued

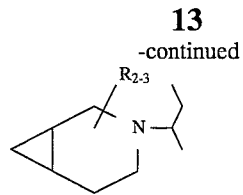  (X)(R$_{2-1}$/R$_{2-2}$-8)

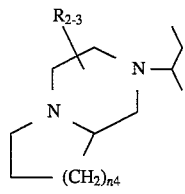  (Y)(R$_{2-1}$/R$_{2-2}$-9)

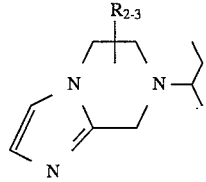  (Z)(R$_{2-1}$/R$_{2-2}$-10)

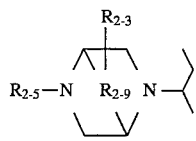  (AA)(R$_{2-1}$/R$_{2-2}$-11)

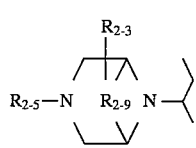  (BB)(R$_{2-1}$/R$_{2-2}$-12)

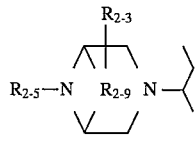  (CC)(R$_{2-1}$/R$_{2-2}$-13)

where
R$_{2-3}$ and R$_{2-5}$ are as defined above,
where
R$_{2-9}$ is
(A) —(CH$_2$)$_{n4}$ where n$_4$ is 1 thru 3,
(B) —CH$_2$OCH$_2$,
(C) —CH$_2$SCH$_2$,
(D) —CH$_2$SO$_2$CH$_2$,
(E) —CH$_2$S,
(F) —CH$_2$SO$_2$,
(G) —CH$_2$N(R$_{2-5}$)CH$_2$ where R$_{2-5}$ is as defined above,
where R$_{4-1}$ is defined the same as R$_{2-1}$, but may be the same or different than R$_{2-1}$, where R$_{4-2}$ is defined the same as R$_{2-2}$, but may be the same or different than R$_{2-2}$;
where
R$_7$ is
(C$_7$-1)
(A) —H,
(C$_7$-2)
(B) C$_1$-C$_8$ alkyl optionally substituted with 1 thru 4 R$_{7-1}$ where R$_{7-1}$ is
(1) —F, —Cl, —Br,
(2) C$_1$-C$_4$ alkyl,
(3) —CF$_3$,
(4) -φ,
(5) —OR$_{7-2}$ where R$_{7-2}$ is (a) —H,
(b) C$_1$-C$_4$ alkyl,
(c) phosphate,
(d) sulfate,
(e) —CO—R$_{7-8}$ where R$_{7-8}$ is C$_1$-C$_4$ alkyl or C$_6$-C$_9$ aralkyl,
(f) —CO—NR$_{7-10}$R$_{7-11}$ where R$_{7-10}$ and R$_{7-11}$ are the same or different and are —H or C$_1$-C$_3$ alkyl,
(g) sulfamate,
(h) glucosyl,
(i) galactosyl,
(j) glucuronic acid,
(k) maltosyl,
(l) arabinosyl,
(m) xylosyl,
(n) —CO—CH(NH$_2$)—H,
(o) —CO—CH(NH$_2$)—CH$_3$,
(p) —CO—CH(NH$_2$)—CH(CH$_3$)$_2$,
(q) —CO—CH(NH$_2$)—CH$_2$—CH(CH$_3$)$_2$,
(r) —CO—CH(NH$_2$)—CH(CH$_3$)—CH$_2$—CH$_3$,
(s) —CO—CH(NH$_2$)—CH$_2$—OH,
(t) —CO—CH(NH$_2$)—CH(OH)—CH$_3$,
(u) —CO—CH(NH$_2$)—CH$_2$-φ,
(v) —CO—CH(NH$_2$)—CH$_2$-[p-phenyl]—OH,
(w) —CO—CH(NH$_2$)—CH$_2$-[2-indolyl]
(x) —CO—CH(NH$_2$)—CH$_2$—SH,
(y) —CO—CH(NH$_2$)—CH$_2$—CH$_2$—S—CH$_3$,
(z) —CO—C*H—NH—CH$_2$—CH$_2$—C*H$_2$ where the carbon atoms marked with an asterick (*) are bonded together to form a heterocyclic ring,
(aa) —CO—C*H—NH—CH$_2$—CH(OH)—C*H$_2$ where the carbon atoms marked with an asterick (*) are bonded together to form a heterocyclic ring,
(bb) —CO—CH(NH$_2$)—CH$_2$—COOH,
(cc) —CO—CH(NH$_2$)—CH$_2$—CONH$_2$,
(dd) —CO—CH(NH$_2$)—CH$_2$—CH$_2$—COOH,
(ee) —CO—CH(NH$_2$)—CH$_2$—CH$_2$—CONH$_2$,
(ff) —CO—CH(NH$_2$)—CH$_2$—C*—NH—CH=N—C*H= where the carbon atoms marked with an asterick (*) are bonded together to form a heterocyclic ring,
(gg) —CO—CH(NH$_2$)—CH$_2$—CH$_2$—CH$_2$—NH—C(=NH)—NH$_2$,
(hh) —CO—CH(NH$_2$)—CH$_2$—CH$_2$—CH$_2$—CH$_2$—NH$_2$,
(ii) —CO—CH(NH$_2$)—CH$_2$—CH$_2$—CH(OH)—CH$_2$—NH$_2$,
(jj) —CO—CH$_2$—CH$_2$—NH$_2$,
(kk) —CO—CH$_2$—CH$_2$—CH$_2$—NH$_2$,
(ll) —CO—CH(NH$_2$)—CH$_2$—CH$_2$—CH$_2$—NH$_2$,
(mm) —CO—CH(NH$_2$)—CH$_2$—CH$_2$—CH$_2$—NH—CO—NH$_2$,
(nn) —CO—CH(NH$_2$)—CH$_2$—CH$_2$—OH,
(6) —SR$_{7-2}$ where R$_{7-2}$ is defined above,
(7) —NHR$_{7-3}$ where R$_{7-3}$ is —H or C$_1$-C$_4$ alkyl,
(8) —NR$_{7-4}$R$_{7-5}$ where R$_{7-4}$ and R$_{7-5}$ are the same or different and are C$_1$-C$_4$ alkyl or may taken together with the attached nitrogen atom to form the heterocyclic ring —N*—(CH$_2$)$_{n1}$—R$_{5-6}$—(CH$_2$)$_{n2}$* where the atoms marked with an asterisk (*) are bonded together resulting in the formation of a ring, where n$_1$ is 1 thru 5, n$_2$ is 0 thru 3 and R$_{5-6}$ is
(a) —CH$_2$—,
(b) —O—,
(c) —S—,
(d) —NR$_{7-9}$ where R$_{7-9}$ is (i) $C_1$-$C_6$ alkyl optionally substituted with 1 thru 3 —OH or —OCH$_3$,
(ii) $C_1$-$C_6$ alkylcarbonyl,
(iii) $C_1$-$C_6$ alkoxycarbonyl,
(iv) $C_6$-$C_{12}$ arylalkyl,
(v) -φ,
(vi) —SO$_2$—$C_1$-$C_8$ alkyl,
(vii) CH$_3$—C*—O—CO—O—C*—CH$_2$— where the carbon atoms designated by * are attached by a double bond to form a five member ring, (9) —(CH$_2$)$_{n3}$CO$_2$R$_{7-2}$, where n$_3$ is 0 thru 6 and R$_{7-2}$ is as defined above,

(10) —(CH$_2$)$_{n3}$CON(R$_{7-3}$)$_2$ where n$_3$ is as defined as above and where R$_{7-3}$ may be the same or different and is defined above,

(11) —(CH$_2$)$_{n3}$CONR$_{7-4}$R$_{7-5}$ where n$_3$, R$_{7-4}$, R$_{7-5}$ are as defined above,

(12) —(CH$_2$)$_{n1}$OR$_{7-2}$ where R$_{7-2}$ and n$_1$ are as defined above,

(13) —(CH$_2$)$_{n1}$OCOR$_{7-3}$ where R$_{7-3}$ and n$_1$ are as defined above,

(14) —(CH$_2$)$_{n1}$SR$_{7-2}$ where R$_{7-2}$ and n$_1$ are as defined above,

(15) —(CH$_2$)$_{n1}$NHR$_{7-3}$ where R$_{7-3}$ and n$_1$ are as defined above,

(16) —(CH$_2$)$_{n1}$NR$_{7-4}$R$_{7-5}$ where R$_{7-4}$, R$_{7-5}$, and n$_1$ are as defined above, (C$_5$-3)
(C) —(CH$_2$)$_{n3}$-φ optionally substituted with 1 thru 4 R$_{7-1}$ where R$_{7-1}$ and n$_3$ are as defined as above, (D) —(CH$_2$)$_{n3}$-pyridin-2-, 3- or 4-yl optionally substituted with 1 thru 4 R$_{7-1}$ where n$_3$ and R$_{7-1}$ are as defined above, (E) —(CH$_2$)$_{n3}$-naphthalin-1-, 2-yl optionally substituted with 1 thru 4 R$_{7-1}$ where n$_3$ and R$_{7-1}$ are as defined above, (C$_5$-5)
(F) —(CH$_2$)$_{n3}$CO$_2$R$_{7-2}$ where n$_3$ and R$_{7-2}$ are as defined above, (C$_5$-6)
(G) —(CH$_2$)$_{n3}$CON(R$_{7-3}$)$_2$ where n$_3$ is as defined as above and where R$_{7-3}$ may be the same or different and is as defined above, (C$_5$-7)
(H) —(CH$_2$)$_{n3}$CONR$_{7-4}$R$_{7-5}$ where n$_3$, R$_{7-4}$, R$_{7-5}$ are as defined above, (C$_5$-8)
(I) —(CH$_2$)$_{n3}$SO$_3$R$_{7-2}$ where n$_3$ and R$_{7-2}$ are as defined above, (C$_5$-9)
(J) —C$_3$-C$_7$ cycloalkyl; with the provisos:
(1) that when R$_7$ is —H, R$_{56-1}$, R$_{56-3}$ and R$_{56-4}$ can not be —OH;
(2) that when R$_{2-1}$ and R$_{2-2}$ is taken together with the attached nitrogen atom to form 1-pyrrolidinyl, and R$_{4-1}$ and R$_{4-2}$ is taken together with the attached nitrogen atom to form 1-pyrrolidinyl, R$_7$ is not —CH$_2$—CH$_2$—morphinyl; and pharmaceutically acceptable salts thereof.

Further disclosed are the compounds of EXAMPLES 192, 193, 195 and 197–202.

DETAILED DESCRIPTION OF THE INVENTION

The bicyclic heterocyclic amines (XXX) of the present invention encompass a number of different type of ring systems depending on the definitions of W$_1$, W$_3$ and W$_5$. These novel pharmaceutically active agents are produced by methods known to those skilled in the art from known starting compounds. The invention is the bicyclic heterocyclic amines (XXX), not the chemistry used to produce them.

The starting point in the synthesis of the pharmacologically active bicyclic heterocyclic amines (XXX) is the halogenated aryl ring whether it is a pyrimidine ring (W$_1$ and W$_3$ are both —N==) or a pyridine ring (one of W$_1$ or W$_3$ is —N== and the other is —CH==). Before forming the second ring, the final desired substituents (—NR$_{2-1}$R$_{2-2}$ and —NR$_{4-1}$R$_{4-2}$) on the heteroaryl ring are added or formed. The substituents —NR$_{2-1}$R$_{2-2}$ and —NR$_{4-1}$R$_{4-2}$ may be the same or different, it is preferred that they be the same for simplicity of chemical synthesis. The formation of the tertiary amines (—NR$_{2-1}$R$_{2-2}$, —NR$_{4-1}$R$_{4-2}$) from halogenated aromatic/heteroaromatic compounds is known to those skilled in the art, see *J. Med. Chem.*, 33, 1145 (1990). Generally, after the desired groups at the C$_2$ and C$_4$ positions are formed, the 5-membered ring is formed. However, in some cases the —NR$_{2-1}$NR$_{2-2}$ and NR$_{4-1}$R$_{4-2}$ are added to the preformed bicyclic-heterocyclic amine (XXX). The —NR$_{2-1}$NR$_{2-2}$ and NR$_{4-1}$R$_{4-2}$ groups can be cyclized to form rings including 1-pyrrolidinyl, 1-piperidinyl, 1-morpholinyl, 1-piperazinyl, 1-aziridinyl, 1-azetidinyl or a number of other heterocyclic rings. These rings can be substituted with 1 thru 3 groups, R$_{2-3}$. When R$_{2-3}$ is alkyl, no more than two such groups can be on any one carbon atom in the ring. When R$_{2-3}$ is other than alkyl, only one such group can be on any one carbon atom.

The 5-membered ring is formed by methods known to those skilled in the art.

Specific cases of the different ring formations of the bicyclic heterocyclic amines (XXX) will be discussed individually below.

When W$_1$ is —N==, W$_3$ is —N== and W$_5$ is —C==R$_5$ the bicyclic heterocyclic amines (XXX) are pyrrolo[2,3-d]pyrimidines (VII) and are prepared by the process of CHART B and known means, see Comprehensive Heterocyclic Chemistry, A. R. Katritzky and C. W. Rees, Ed., Vol. 4, Pergamon Press, 1984, p. 528. The pyrrolo[2,3-d]pyrimidine ring system is known, see for example, 4-amino-7β-D-ribofuranosyl-7H-pyrrolo[2,3-d]pyrimidine which is tubercidin. The pyrrolo[2,3-d])pyrimidines (VII) are prepared starting from trihalopyrimidines (I) which are well known to those skilled in the art or are commercially available. The preferred 2,4,6-trihalopyrimidine (I) is trichloropyrimidine (I). A mixture of the trihalopyrimidine (I) in an inert solvent such as THF is allowed to react with 1 equivalent of a primary amine, R$_7$—NH$_2$ (II) in the presence of an acid scavenger. Organic amines such as pyridine, triethylamine, diisopropylethylamine and inorganic bases such as potassium carbonate are useful acid scavengers. The reactants are mixed at a reduced temperature (−80° to 0°) and the reaction mixture is allowed to warm to room temperature (20°–25°) and then is often concentrated at reduced pressure. The residue is partitioned between an organic solvent such as ethyl acetate or methylene chloride and an aqueous inorganic base such as potassium bicarbonate. The extract is dried, concentrated, and the residue chromatographed on silica gel to separate the desired 4-aminopyrimidine (III). The 4-aminopyrimidine (III) is mixed with an excess of a secondary amine, NHR$_{2-1}$R$_{2-2}$ (IV) and the mixture is heated under reflux for 2 to 24 hours. The mixture is allowed to cool and then is concentrated. The residue is partitioned as described above to remove the inorganic salts. The crude product is purified by conventional means (e.g. crystallization and/or chromatography) to give the desired trisubstituted pyrimidine (V). If a relatively nonvolatile secondary amine is used, the reaction mixture is diluted with an organic solvent such as ethyl acetate and the mixture is washed with an aqueous inorganic base. Alternatively, the required trisubstituted pyrimidine (V) intermediate may be obtained from reaction of a 2,4-di-amino-6-halopyridine with the appropriate primary amine (II) at elevated temperatures. The trisubstituted pyrimidine (V) is contacted with an α-haloketone, $R_5$—$CHX_1$—CO—$R_6$ (VI) where $X_1$ is preferrably —Cl or —Br which provides a ketopyrimidine intermediate. The ketopyrimidine may cyclize to the desired pyrrolo[2,3-d]pyrimidine (VII) spontaneously at 20°–25°. The cyclization may be accomplished by warming the ketopyrimidine intermediate in an inert solvent (e.g. THF, ethyl acetate, toluene, methylene chloride) in the presence (or absence) of a mild dehydrating agent such as magnesium sulfate, molecular sieve, trialkylorthoformate, etc. The cyclization may also be achieved by chromatography of the intermediate on silica gel in the conventional way. The final product is purified by chromatography and/or crystallization.

When $W_1$ is —N=, $W_3$ is —CH= and $W_5$ is —N= the bicyclic heterocyclic amines (XXX) are 3H-imidazo[4,5-b]pyridines (XXV), a known system, see DE 3 318 671 A1 CA 44, 2041b, Swiss Patent 260,741, and are prepared by the process of CHART C. The 2-(primary amino)-4,6-diaminopyridine (X) are prepared as described in CHART D. Nitration of the 2-(primary amino)-4,6-diaminopyridines (X) by conventional methods such as nitric acid (or sodium nitrate to form the analogous nitroso compound) provides the nitrotriaminopyridines (XXIII) and the regioisomer which may be separated by fractional crystallization or chromatography. The nitro group of the nitrotriaminopyridines (XXIII) may be reduced by hydrogenation in an inert solvent such as ethanol in the presence of palladium on carbon to provide the tetraaminopyridines (XXIV). The tetraaminopyridines (XXIV) are reacted with an acid halide or aldehyde as described above for CHART A to provide the desired 3H-imidazo[4,5-b]pyridines (XXV).

When $W_1$ is —N=, $W_3$ is —CH= and $W_5$ is —$CR_5$= the bicyclic heterocyclic amines (XXX) are 1H-pyrrolo[2,3-b]pyridines (XI), a known ring system, see J. Chem. Soc. 101, 1912, 1779, and are prepared by the process of CHART D. The amino group of 4-amino-2,6-dichloropyridines (VIII) is alkylated by conventional methods known to those skilled in the art to provide aminopyridines (VIIIA). Displacement of one of the chlorine atoms of the aminopyridines (VIIIA) is accomplished by treatment of the aminopyridines (VIIIA) with one equivalent of the desired secondary mines, $HNR_{4-1}R_{4-2}$, (IV) in an inert solvent such as THF or acetonitrile in the presence of an inorganic base such as potassium carbonate to provide the 2,4-di-amino-6-halopyridines (IX). Displacement of the remaining halo group with a primary mine, $NH_2R_7$, (II) is accomplished in a similar manner at elevated temperature. Alternatively, the order of addition of the two amines may be reversed where $NH_2R_7$ is added to aminopyridine (VIIIA) followed by reaction with a secondary amine $HNR_{2-1}R_{2-2}$ (IV). Reaction of 2-(amino or substituted amino)-4,6-diaminopyridines (X) with an α-haloketone ($R_5CHX_1COR_6$, VI) as described for CHART B provides a keto-pyridine intermediate which is cyclized to 1H-pyrrolo[2,3-b]pyridines (XI) in a similar fashion to that mentioned previously.

When $W_1$ is —CH=, $W_3$ is —N= and $W_5$ is —N= the bicyclic heterocyclic amines (XXX) are 1H-imidazo[4,5-c] pyridines (XXIX) and are prepared by the process of CHART E. This ring system is known, see Biochem. Z. 49, 1913, 182. In much the same manner as CHART C, the amino group of 4-amino-2,6-dichloropyridine (VIII) is alkylated by conventional methods using the alkylating agent, $R_7$—X, (XIV) which are known to those skilled in the art to provide 3-nitro-2,4,6-triaminopyridines (XXVI). In some cases the 3-nitro-2,4,6-triaminopyridines (XXVI) are protected with conventional protecting groups such as BOC, acetamide or N-benzyl by methods known to those skilled in the art. Displacement of the chlorines may be accomplished by treatment of the 3-nitro-2,4,6-triaminopyridines (XXVI) with excess of the desired secondary amines, $HNR_{2-1}R_{2-2}$ and $HNR_{4-1}R_{4-2}$ (IV) in an inert solvent such as THF or acetonitrile in the presence of an inorganic base such as potassium carbonate to provide the 4-amino-2,6-diaminopyridines (XV). Nitration of the 4-amino-2,6-diaminopyridines (XV) by conventional methods as described in CHART C with a nitrating agent such as nitric acid provides the 3-nitro-2,4,6-triaminopyridines (XXVII) and the regioisomer which may be separated by fractional crystallization or chromatography. The nitro group may be reduced by hydrogenation of the 3-nitro-2,4,6-triaminopyridines (XXVII) in an inert solvent such as ethanol in the presence of palladium on carbon to provide the 2,3,4,6-tetraaminopyridines (XXVIII). Any protecting groups may be removed at this moment by conventional methods. The 2,3,4,6-tetraaminopyridines (XXVIII) may be reacted with an acid chloride followed by base or with an aldehyde in the presence of cupric acetate as described for CHART C to provide the 1H-imidazo[4,5-c]pyridines (XXIX).

When $W_1$ is —CH=, $W_3$ is —N= and $W_5$ is —$CR_5$= the bicyclic heterocyclic amines (XXX) are 1H-pyrrolo[3,2-c]pyridines (XVI) and are prepared by the process of CHART F. This ring system is known, see J. Chem. Soc. 1909, 95, 1526. Following a similar process to that described for CHART D, displacement of the —Cl groups of 4-amino-2,6-dichloropyridine (VIII) is be accomplished by treatment with excess of the desired secondary amine, $HNR_{2-1}R_{2-2}$, (IV) in an inert solvent such as THF or acetonitrile in the presence of an inorganic base such as potassium carbonate to provide 4-amino-2,6-(substituted amino)pyridines (XIII). The primary amino group of the 4-amino-2,6-(substituted amino)pyridines (XIII) is alkylated by conventional methods using the alkylating agent, $R_7$—X, (XIV) which is known to those skilled in the art to provide alkylaminopyridine (XV). Reaction of alkylaminopyridine (XV) with an α-haloketone ($R_5CHX_1COR_6$, VI) as described above provides a keto-pyridine intermediate which is cyclized to 1H-pyrrolo[3,2-c]pyridines (XVI) in a similar fashion to that described above.

CHART A discloses a process when the functionality $R_5$ of the bicyclic heterocyclic amines (XXX) is —H, it can be transformed to other functionality at $C_5$. The formyl, hydroxymethyl, and cyano analogs have biological activities themselves and are also useful intermediates for further functionalization. The formyl compound is obtained by Vilsmeier-type formulation of pyrrolo[2,3-d])pyrimidines (VII) (phosphorous oxychloride, DMF) and from that, the hydroxylmethyl compound is derived by hydride reduction (e.g. sodium borohydride). The nitrile can be made by conversion of the formyl group to the oxime (=N—OH) with hydroxylamine ($NH_2OH$) followed by dehydration of the oxime (e.g. by heating in DMF).

CHART G discloses process where the functionality $R_5$, $R_6$ and/or $R_7$ can be modified after the formation of the bicyclic heterocyclic amines (XXX). For instance $R_7$ may be a removable group such as tert-butyl or N-benzyl. Deprotection of such a compound by methods known to those skilled in the art will provide the —N—H analog. Alkylation, acylation, or other routine operations will provide compounds of formula (XXX) with a new $R_7$. Alternatively, the substituents at $X_5$, $X_6$, and $X_7$ may contain a modifiable functional group that can produce new compounds containing altered $R_5$, $R_6$, and $R_7$ substituents. For example, an aromatic ether can be dealkylated by routine methods such as hydrogen bromide to provide a phenol. The resultant phenol can be modified by routine methods to provide additional analogs and/or possible prodrugs including alcohols, amines or thiol sidechains. These can be modified by conventional methods, or in the case of the alcohol sidechains, converted to leaving groups which are subsequently reacted with various nucleophiles. When $R_{5-2}$ is an amino acid derivative, it is understood that the connection is via an ester bond formed between the hydroxylic group on the substrate and the carboxyl group on the amino acid. In much the same manner, the amine groups (—$NR_{2-1}R_{2-2}$, —$NR_{4-1}R_{4-2}$) may contain modifiable functional groups (possibly in a protected form) which can be modified as described above to form compounds containing new —$NR_{2-1}R_{2-2}$ and/or —$NR_{4-1}R_{4-2}$.

It is preferred that the bicyclic heterocylic amine compounds of formula (XXX) be a pyrrolo[2,3-d]pyrimidine (VII) where $W_1$ and $W_3$ are both —N= and $W_5$ is —$CR_5$=.

The bicyclic heterocyclic amines (XXX) in general and the pyrrolo[2,3-d]pyrimidines (VII) more specifically, are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids hydrochloric, hydrobromic, sulfuric, phosphoric, nitric, citric, methanesulfonic $CH_3$—$(CH_2)_{n1}$—COOH where $n_1$ is 0 thru 4, HOOC—$(CH_2)_{n1}$—COOH where n is as defined above, HOOC—CH=CH—COOH, φ—COOH. For other acceptable salts, see *Int. J. Pharm.*, 33, 201–217 (1986).

It is preferred that $W_1$ and $W_3$ are both —N=. It is preferred that $W_5$ is —$CR_5$=. It is preferred that $R_5$ is —H, —$CH_3$, -φ and 4-hydroxyphenyl. It is preferred that —$NR_{2-1}R_{2-2}$ be the same as —$NR_{4-1}R_{4-2}$. It is preferred that $R_{2-1}$ and $R_{2-2}$ are taken together with the attached nitrogen atom to form 1-pyrrolidinyl, 1-piperazinyl, 1-thiomorpholinyl and 4-methylpiperazin-1-yl; it is more preferred that $R_{2-1}$ and $R_{2-2}$ form 1-pyrrolidinyl and 1-piperazinyl. It is preferred that $R_6$ is is —H, —$CH_3$, -φ and 4-hydroxyphenyl. It is preferred that $R_7$ is is —H, —$CH_3$, -φ, 2-(1-morpholinyl-)ethyl and 2-(1-piperazinyl)ethyl. It is preferred that the non-cyclized bicyclic heterocyclic amines (XXX) be selected from the group consisting of compounds of EXAMPLES 6, 8, 9, 12–15, 18–22, 24–29, 36–38, 40, 41, 44, 46–48, 49, 50, 54, 56, 60, 65, 70, 73, 76, 78–80, 82, 84, 86, 91, 94, 99, 101, 103–105, 107, 109, 110, 115, 118–123, 126–133, 139–151, 153–156 and 169–191. It is more preferred that the non-cyclized bicyclic heterocyclic amine (XXX) be selected from the group consisting of compounds of EXAMPLEs 6, 25, 26, 29, 54, 70, 84, 86, 141 and 145; it is most preferred that the non-cyclized bicyclic heterocyclic amines (XXX) be the compound of EXAMPLEs 6 and 54. It is preferred that the $C_5$–$C_6$-cyclized bicyclic amines (XXX) be selected from the group consisting of compounds of the EXAMPLEs 112, 138, 161 and 168, it is more preferred that the $C_5$–$C_6$ bicyclic amine (XXX) be the compound of EXAMPLE 112. In addition there are certain preferred compounds which are not within the scope of the bicyclic hetercyclic amines (XXX), these include 7, 30, 32–34, 52, 89, 96, 136, 152, 157–160, 162–165 and 167; more preferred are the compounds of EXAMPLEs 7, 52 and 136. It is preferred that the bicyclic heterocyclic amine (XXX) be a salt rather than the free base.

It is preferred that the bicyclic heterocyclic amines (XXX) be in the form of a pharmaceutically acceptable salt and it is preferred that the salt be selected from the group consisting of hydrochloride, hydrobromide, maleate and methanesulfonate.

The bicyclic heterocyclic amines (XXX) are useful in treating/preventing spinal trauma, mild and/or moderate to severe head injury, subarachnoid hemorrhage and subsequent ischemic (thromboembolic) stroke, asthma and reduction of mucous formation/secretion in the lung, muscular dystrophy, adriamycin cardiac toxicity, Parkinsonism, Alzheimer's disease, other degenerative neurological disorders, multiple sclerosis, organ damage during reperfusion after transplant, skin graft rejection, hemorrhagic, traumatic and septic shock, and conditions such as severe burns, ARDS, inflammatory diseases such as osteo- or rheumatoid arthritis, nephrotic syndrome (immunological), systemic lupus erythematosis, allergic reactions, diabetes, atherosclerosis, inflammation (dermatological antiinflammatory and antipsoriasis agents), emphysema, cancer (limit metastasis, limit tumor growth), (stress induced) ulcers, inflammatory bowel diseases such as ulcerative colitis and Crohn's disease. The compounds are also useful for prophylactic treatment before neurological procedures, for treatment of myocardial infarctions, drug allergic reactions, post-resuscitation ischemia, and migraine and cluster headaches. The compounds have use in ophthalmology, e.g., in treatment of diabetic retinopathy, age-related macular degeneration, cataracts and glaucoma, light-induced retinal damage and in irrigation mixtures used in eye surgery. The bicyclic heterocyclic amines (XXX) of the present invention are also useful in early management of cardiac arrest and resuscitation.

In humans, the bicyclic heterocyclic amines (XXX) of the present invention are useful in treating subarachnoid hemorrhage and subsequent cerebral vasospasm, global cerebral ischemia, with resuscitation (CPR) to prevent post-ischemic brain damage, brain tumor (neuroprotective), Bells Palsy, other degenerative neurological disorders, hepatic necrosis (e.g. from viral hepatitis), some forms of radiation damage (for example during radiation treatment or from accidental exposure to radiation), myocardial damage after myocardial ischemia, pre-birth infant strangulation and infant hypoxia syndrome, such opthalmic disorders as uveitis and optic neuritis and ischemic bowel syndrome.

In humans, the bicyclic heterocyclic amines (XXX) are useful in preventing damage following cardiopulmonary resuscitation, neurological or cardiovascular surgery and from cardiac infarction, occular damage after opthalmic surgery (e.g. cataritic surgery).

In humans, the bicyclic heterocyclic amines are useful in prevention of hyperoxic lung injury and in treating skeletal muscle ischemic injury as well as diaphragm fatigue injury.

It is preferred that the bicyclic heterocyclic amines (XXX) are useful in treating asthma (and reduction of mucous formation/secretion in the lung), muscular dystrophy, Parkinsonism, Alzheimer's disease and stroke.

Generally, the bicyclic heterocyclic amines (XXX) are used like the glucocorticoid pharmaceuticals for the treatment of the above human conditions as well as the animal conditions listed below. While the bicyclic heterocyclic amines (XXX) are useful in both humans and animals in treating many of the same conditions and preventing damage from the same problems as the glucocorticoids, the bicyclic heterocyclic amines (XXX) are useful in treating a number of conditions and preventing damage from conditions where the glucocorticoids are not useful. The bicyclic heterocyclic amines (XXX) have no glucocorticoid activity and therefore, unlike the glucocorticoids, they can be given daily for long periods of time (used chronically) without the side effects associated with the glucocorticoids. This is a distinct advantage.

It is to be understood that each of the bicyclic heterocyclic amines (XXX) is useful to a different degree for treating each of the conditions above. However, as is known to those skilled in the art, some of the bicyclic heterocyclic amines (XXX) are better for treating some conditions and others are better for treating other conditions.

The rat brain malonyldialdehyde and mouse spinal neuron lipid peroxidation assays (Hall et at, J. of Pcol. Exptl. Ther., 258, 688–694 (1991) identifies compounds which are antioxidants, which inhibit lipid peroxidation, and are useful in treating spinal trauma, mild and/or moderate to severe head injury, degenerative neurological disorders, etc. This test also will permit one skilled in the art to determine the relative degree to which each of the bicyclic heterocyclic amines (XXX) are useful and which are the preferred compounds. Another method useful for determining which particular compounds inhibit lipid peroxidation, and which are therefore useful in treating spinal trauma, mild and/or moderate to severe head injury, degenerative neurological disorders, etc is described by Pryor in Methods of Enzymology 105, 293 (1984). This test also will permit one skilled in the art to determine the relative degree to which each of the bicyclic heterocyclic amines (XXX) are useful and which are the preferred compounds. Further, the mouse head injury assay of Hall, J. Neurosurg., 62, 882 (1980) discloses an assay from which one skilled in the art can readily determine which particular bicyclic heterocyclic amines (XXX) are useful in the acute treatment of spinal trauma or mild and/or moderate to severe head injury. This test also will permit one skilled in the art to determine the relative degree to which each of the bicyclic heterocyclic amines (XXX) are useful and which are the preferred compounds. Additionally, the cat 48 hour motor nerve degeneration model of Hall et at, Exp. Neurol., 79, 488 (1983) discloses a routine assay from which one skilled in the art can readily determine which particular bicyclic heterocyclic amines (XXX) are useful in treating chronic degenerative neurological disorders such as Parkinsonism, Alzheimer's disease etc. This test also will permit one skilled in the art to determine the relative degree to which each of the bicyclic heterocyclic amines (XXX) are useful and which are the preferred compounds. H. Johnson in Int. Arch. Allergy Appl. Immunol., 70, 169 (1983) has described the ascaris sensitized rhesus monkey assay for anti-asthma drugs.

The standard conditions for treatment are to give the bicyclic heterocyclic amines (XXX) orally or parenterally, e.g. IV (that is by injection, infusion or continuous drip) or IM, with a standard dose of about 0.05 to about 20 mg/kg/day IV for up to 10 days or about 0.05 to about 20 mg/kg/day; one to four times daily by mouth.

For treating spinal trauma, mild and moderate to severe head injury, damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used.

Typical treatment will involve an initial loading dose, e.g. an IV dose of 0.01 mg to 2 mg/kg followed by maintenance dosing e.g. IV infusion for a day to a week depending on the particular condition of the patient and the particular compound used. This may be supplemented with IM or oral dosing for days, weeks or months to prevent delayed neuronal degeneration in neurological applications (eg spinal trauma, head injury).

In treating subarachnoid hemorrhage and subsequent cerebral vasospasm or ischemic (thromboembolic) stroke the standard conditions are used and patients at risk are pre-treated orally.

In treating excess mucous secretion and asthma, the bicyclic heterocyclic amines (XXX) are administered orally, IV and by inhalation in the standard dose. In treating excess mucous secretions the oral dose of the bicyclic heterocyclic amines (XXX) used is from about 0.05 to about 20 mg/kg/day. The frequency of administration is one thru 4 times dally. The oral administration of the bicyclic heterocyclic amines (XXX) to treat excess mucous secretions may go on for months or even years. The susceptible individuals can be pre-treated a few hours before an expected problem. The IV dose is about 0.05 to about 20 mg/kg/day. The aerosol formulation contains about 0.01 to about 1.0% of the bicyclic heterocyclic amines (XXX) and is administered or used about four times daily as needed.

The bicyclic heterocyclic amines (XXX) are useful in treating various cardiovascular conditions. They are useful in treatment of individuals who have suffered a heart attack. The bicyclic heterocyclic amines (XXX) will decrease the incidence and/or severity of a second heart attack by decreasing the incidence of serious arrhythmias in this population. The bicyclic heterocyclic amines (XXX) will be taken orally for an indefinite length of time. The bicyclic heterocyclic amines (XXX) are also useful in treating myocardial infarctions to decrease infarct size and improve survival. These individuals will suffer fewer dysrhythmic events. The bicyclic heterocyclic amines (XXX) may be given by IV in this population. In addition, the bicyclic heterocyclic amines (XXX) are useful for treating individuals after various cardiac procedures such as bypass. The bicyclic heterocyclic amines (XXX) will decrease pericardial inflammation and reduce the post-surgical complications of these procedures. The bicyclic heterocyclic amines (XXX) will be administered before the surgical procedure and for about 5 to about 90 days after the procedure. Further, the bicyclic heterocyclic amines (XXX) are useful for treating individuals before and after angioplasty to decrease complications from this procedure.

In early management of cardiac arrest and resuscitation, the bicyclic heterocyclic mines (XXX) are administered IV with a dose of about 0.1 to about 10 mg/kg/day.

The bicyclic heterocyclic mines (XXX) will be useful in lung, cardiac, liver, kidney and pancreatic transplants. With regard to transplants, the bicyclic heterocyclic mines (XXX) will useful to treat the recipient for about 1 to about 30 days to improve condition of the transplanted organ and to reduce rejection. In addition, the bicyclic heterocyclic mines (XXX) will be useful to treat the donor of the organ to improve quality of the stored organ. For these transplants, the bicyclic heterocyclic mines (XXX) can be administered by IV to the donor or it can be incorporated in preservation solutions to improve storage of the organ. In the former case, dose is usually about 1 to about 20 mg/kg/day. In the case of storage, final concentrations should be about 0.5 to about 100 υmolar. The bicyclic heterocyclic mines (XXX) can be formulated as an emulsion, in an aqueous vehicle, or in an organic solvent for use in preservation solutions.

Other uses of the bicyclic heterocyclic mines (XXX) include the full spectrum of degenerative neurologic disorders, inflammatory maladies such as rheumatoid arthritis and lupus, lung insults such as smoke inhalation, blast injury, hyperoxic injury and chemical toxic insults (such as bleomycin toxicity). The drugs also are useful in prevention of radiation injury, for example to gut and brain. They are useful in bowel, disorders such as Crohn's and ulcerative colitis.

In treating muscular dystrophy, Parkinsonism, Alzheimer's disease and other degenerative neurological disorders (amyotrophic lateral sclerosis; multiple sclerosis) bicyclic heterocyclic mines (XXX) are administered orally using a dose of about 0.05 to about 20 mg/kg/day, administered or used one to four times a day. The treatment may go on for years.

In addition, the bicyclic heterocyclic amines (XXX) are useful in treating embryo implantation (antifertility), arthritis, and atherosclerosis with or without co-administered oral heparin or systemic heparin fragments, see Science 221,719 (1983).

In treating adriamycin-induced cardiac toxicity, the bicyclic heterocyclic mines (XXX) are administered orally or IV using a dose of about 0.05 to about 50 mg/kg/day, preferably about 0.5 to about 10 mg/kg/day. The bicyclic heterocyclic mines (XXX) are preferably given concomitantly with IV adriamycin or the individual is pre-treated with the bicyclic heterocyclic mines (XXX).

For prophylaxis prior to and preventing damage after neurological or cardiovascular surgery the bicyclic heterocyclic mines (XXX) are used according to the standard conditions. The patient can be pretreated with a single IV or IM dose just prior to surgery or orally before and after surgery.

In treating osteo- or rheumatoid arthritis and other inflammatory diseases, the bicyclic heterocyclic amines (XXX) are given orally or IM in doses of about 0.05 to about 20 mg/kg/day, one to four times daily. Orally the drug will be given over a period of months or years alone with other steroidal or nonsteroidal antiinflammatory agents. The initial dose with some severe rheumatoid patients may be given IV and followed with an IV drip for up to 24 hours or more. In addition, intra-arterial administration may be employed.

In treating drug allergic reactions, the bicyclic heterocyclic amines (XXX) are given in a dose of about 0.05 to 20 mg/kg/day, administered one to four times daily orally and IV. Typical treatment would be an initial IV loading dose followed by oral dosing for a few days or more.

In treating atherosclerosis and emphysema, the bicyclic heterocyclic amines (XXX) are given orally in a dose of about 0.05 to about 20 mg/kg/day, one to four times daily for months or years.

In treating dermatological inflammatory conditions including psoriasis, the bicyclic heterocyclic amines (XXX) are given orally in a dose of about 0.05 to about 20 mg/kg/day, one to four times daily or applied topically as a cream, ointment or lotion or equivalent dosage form in a concentration of about 0.05 to about 5% as long as needed. In treating these conditions the bicyclic heterocyclic amines (XXX) can be used with steroidal agents.

The bicyclic heterocyclic amines (XXX) are useful in the prevention and treatment of stress ulcers and of gastric intolerance caused by drugs such as nonsteroidal anti-inflammatory compounds (NOSAC). Stress ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented by these compounds. NOSAC include drugs such as ibuprofen, aspirin, indomethacin, naproxen, piroxicam and the like that are usually taken for analgesia, and that are often associated with gastrointestinal intolerance characterized by pain and lesions that may lead to bleeding. The bicyclic heterocyclic amines (XXX) will be administered preferentially by the oral route either as tablets, capsules or liquids, in doses ranging from about 5 to about 500 mg, two to four times a day. The treatment would be wither preventive, i.e., starting before ulcers have formed in patients at risk of developing such lesions, or therapeutic, i.e., once the ulcers have formed. In patients whose clinical conditions precludes swallowing the oral dosage forms, the bicyclic heterocyclic amines (XXX) would be given either through a nasogastric tube, or parenterally, i.e., IV or IM. The parenteral doses would range from about 1 to about 100 mg and be administered one to four times a day or by IV.

In dogs, the bicyclic heterocyclic amines (XXX) are useful in treating trauma, intervertebral diseases (slipped disk), traumatic shock, flea bite and other allergies.

In horses, the bicyclic heterocyclic amines (XXX) are useful in treating endotoxic or septic shock which follows colic, pretreatment before surgery for colic and treatment of Founder (laminitis).

In cattle, the bicyclic heterocyclic amines (XXX) are useful in treating acute coliform mastitis, bovine mastitis, acute allergic reaction to feed lot vaccination and shipping fever.

In pigs, the bicyclic heterocyclic amines (XXX) are useful in treating porcine stress syndrome and thermal stress syndrome.

The term treatment or treating as used in this patient is used broadly and includes both treatment of an existing condition as well as preventing the same condition for occurring where such is possible as is well known to those skilled in the art. For example, the bicyclic heterocyclic amines (XXX) can be used to treat existing asthma conditions and to prevent future ones from occurring. For example, the bicyclic heterocyclic amines (XXX) treat spinal trauma and prevent rejection of skin grafts.

The bicyclic heterocyclic amines (XXX) can be used with other pharmaceutical agents in treatment of the conditions listed above as is known to those skilled in the art.

The exact dosage and frequency of administration depends on the particular bicyclic heterocyclic amines (XXX) used, the particular condition being treated, the severity of the condition being treated, the age, weight, general physical condition of the particular patient, other medication the individual may be taking as is well known to those skilled in the art and can be more accurately determined by measuring the blood level or concentration of the bicyclic heterocyclic amines (XXX) in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)H$. Groups $R_i$ and $R_j$ would represent monovalent variable substituents if attached to the formula $CH_3$—$CH_2$—$C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*$(CH_2)_2$—$N(C_2H_5)$—$CH_2$—C*$H_2$.

A rigid cyclic (ring) structure for any compounds herein defines an orientation with respect to the plane of the ting for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or "...". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —$C(α-R_{i-j})(β-R_{i-k})$—. For example, when the bivalent variable $R_6$, —$C(=R_6)$— is defined to consist of two monovalent variable substituents, the two monovalent variable substituents are α-$R_{6-1}$:β-$R_{6-2}$, ... α-$R_{6-9}$:β-$R_{6-10}$, etc, giving —$C(α-R_{6-1})(β-R_{6-2})$—, ... —$C(α-R_{6-9})(β-R_{6-10})$—, etc. Likewise, for the bivalent variable $R_{11}$, —$C(=R_{11})$—, two monovalent variable substituents are α-$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a rust and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO— ..." means a lactone in which the carbonyl is bonded to $C_2$. However, when designated "... $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The rust method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

DMF refers to dimethylformamide.

Saline refers to an aqueous saturated sodium chloride mixture.

IR refers to infrared spectroscopy.

CMR refers to C-13 magnetic resonance spectroscopy, chemical shifts are reported in ppm ($\delta$) downfield from tetramethylsilane.

NMR refers to nuclear (proton) magnetic resonance spectroscopy, chemical shifts are reported in ppm ($\delta$) downfield from tetramethylsilane.

TMS refers to tetramethylsilane.

-$\phi$ refers to phenyl ($C_6H_5$).

MS refers to mass spectrometry expressed as m/z or mass/charge unit [M+H]$^+$ refers to the positive ion of a parent plus a hydrogen atom. EI refers to electron impact. CI refers to chemical ionization. FAB refers to fast atom bombardment HRMS refers to high remixture mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable salts include the salts of the following acids hydrochloric, hydrobromic, sulfuric, phosphoric, nitric, citric, methanesulfonic $CH_3$—$(CH_2)_{n1}$—COOH where $n_1$ is 0 thru 4, HOOC—$(CH_2)_{n1}$—COOH where n is as defined above, HOOC—CH=CH—COOH, $\phi$—COOH.

When solvent pairs are used, the ratios of solvents used are volume/volume (v/v).

When the solubility of a solid in a solvent is used the ratio of the solid to the solvent is weight/volume (wt/v).

BOC refers to —CO—O—(t-butyl).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

2,6 Dichloro-4-methylaminopyrimidine (III)

2,4,6-Trichloropyrimidine (I, 30 g) is added to a suspension of methylamine hydrochloride (II, 10 g) in THF (250 ml). The mixture is cooled to −6° and diisopropylethylamine (55 ml) is added slowly. The mixture is stirred for 3 days at 20°–25° and then is concentrated under reduced pressure. The residue is absorbed on silica gel (75 g) with ethyl acetate/methylene chloride (1/1) and applied to a silica gel (1 kg) column packed in ethyl acetate/hexane (1/1). Elution is performed with ethyl acetate/hexane (1/1) collecting 500 ml fractions. The appropriate fractions (8–14) are pooled and concentrated to give the title compound, NMR ($CDCl_3$) 6.29, 6.2 and 2.9$\delta$.

EXAMPLE 2

2,6-Dichloro-4-n-propylaminopyrimidine (III)

A mixture of 2,4,6-trichloropyrimidine (I, 11 g) in THF (160 ml) is cooled to −70°. Diisopropylethylamine (11 ml) is added, followed by the addition of a mixture of n-propylamine (II, 4.9 ml) in THY (15 ml). The mixture is allowed to stand for 3 days at 20°–25° and then is concentrated. The residue is partitioned between ethyl acetate and aqueous potassium bicarbonate. The organic extract is washed with water and saline, then dried and concentrated to give a solid. The solid is chromatographed on silica gel (650 g) packed in ethyl acetate/hexane (10/90) and eluted with ethyl acetate/hexane (10→30/90→70). The appropriate fractions (14–18) are pooled and concentrated to give the tire compound, NMR ($CDCl_3$) 6.29, 5.87, 3.21, 1.65 and 0.99$\delta$.

EXAMPLE 3

4-Methylamino-2,6-di-1-pyrrolidinopyrimidine (V)

Pyrrolidine (IV, 25 ml) is added (exothermic) to 2,6-dichloro-4-methylaminopyrimidine (III, EXAMPLE 1, 1.81 g). The mixture is stirred and heated under reflux for 23 hours, then is allowed to cool and concentrated under reduced pressure. The residue is partitioned between ethyl acetate and aqueous potassium bicarbonate, the phases separated and organic phase is concentrated to give a solid. The solid is crystallized from hexane to give the title compound, mp 100.5°–103°; NMR ($CDCl_3$) 4.74, 3.51, 3.43, 2.81 and 1.9$\delta$; CMR ($CDCl_3$) 164.50, 161.92, 160.18, 70.78, 46.06, 45.85, 28.47, 25.44, 25.19$\delta$.

Alternatively, the title compound can be obtained by the reaction of 4-chloro-2,6-di-1-pyrrolidinylpyrimidine and methylamine (II) in pyridine in a pressure tube at 100°, MS (M+) 247.

EXAMPLE 4

4-n-Propylamino-2,6-di-1-pyrrolidinopyrimidine (V)

Pyrrolidine (IV, 30 ml) is added (exothermic) to 2,6-dichloro-4-n-propyl-pyrimidine (III, EXAMPLE 2, 3.09 g). The mixture is stirred and heated under reflux for about 18 hours, then is allowed to cool and is concentrated under reduced pressure. The residue is partitioned between ethyl acetate and aqueous potassium bicarbonate as in EXAMPLE 3 to give a solid which crystallized from ethyl acetate/hexane to give the title compound, NMR ($CDCl_3$) 4.70, 4.34, 3.50, 3.42, 3.12, 1.9, 1.61 and 0.97δ; CMR (CDCl₃) 163.69, 161.91, 160.29, 79.11, 46.07, 46.85, 43.61, 25.45, 25.20, 22.68, 11.56δ.

EXAMPLE 5

2,6-bis-(2—Hydroxyethyl)methylamino-4-methylaminopyrimidine (V)

A mixture of 2,6-dichloro-4-methylamino-pyrimidine (III, EXAMPLE 1, 1.78 g) and 2-(methylamino)ethanol (IV, 25 ml) is heated under reflux for about 18 hours, then is allowed to cool and is diluted with ethyl acetate (100 ml). The mixture is washed with aqueous potassium bicarbonate (0.5N), water (4×25 ml) and with saline (50 ml). The aqueous phases are backwashed with ethyl acetate. The organic extracts are combined, dried and concentrated to give the title compound, NMR (CDCl₃) 4.82, 3.8, 3.68, 3.11, 3.00 and 2.84δ; CMR (CDCl₃) 164.0, 161.76, 71.16, 63.08, 62.47, 52.64, 36.91, 36.49 and 28.35δ.

EXAMPLE 6

6-Phenyl-2,4-di-(1-pyrrolidinyl)-7-methyl-7H-pyrrolo[2,3-d]pyrimidine (VII)

Powdered α-bromoacetophenone (VI, 1.83 g) is added to a stirred, cold mixture of 4-methylamino-2,6-di-(1-pyrrolidinyl)pyrimidine (V, EXAMPLE 3, 2.23 g) in acetonitrile (75 ml) containing diisopropylethylamine (2 ml). The mixture is stirred for 1 hour at 20°–25° a precipitate separates and the mixture is allowed to stand for 2 days and then is concentrated under reduced pressure. The residue is partitioned between methlene chloride and aqueous potassium bicarbonate as described in EXAMPLE 3. The phases are separated, the organic phase is washed, dried and concentrated to give a solid. The solid is absorbed on silica gel (22.5 g) from methylene chloride and applied to a column of silica gel (200 g) packed in acetone/methylene chloride (5/95). The column is eluted with acetone/methylene chloride (5/95), the appropriate fractions are pooled and concentrated to give a solid. The solid is crystallized from acetone/methlene chloride to give the title compound, mp 160.5°–161°; NMR (CDCl₃) 7.5–7.25, 6.43, 3.79, 3.68, 3.63 and 1.95δ; CMR (CDCl₃) 157.94, 155.41, 133.28, 133.04, 128.33, 128.07, 126.62, 100.84, 96.40, 47.36, 46.47, 29.69 and 25.55δ; MS (m/z) M⁺=347.

EXAMPLE 7

6-[2-(2-Methyl)propyl]-7-methyl-2,4-di-(1-pyrrolidinyl)-7H-pyrrolo[2,3-d]pyrimidine (VII)

Following the general procedure of EXAMPLE 6 and making non-critical variations but starting with 4-methylamino-2,6-di-(1-pyrrolidinyl)pyrimidine (V, EXAMPLE 3, 0.495 g) and 1-bromopinacolone (VI, 0.4 g), the title compound is obtained, mp 207°–208°; NMR (CDCl₃) 6.10, 3.79, 3.76, 3.59, 1.95 and 1.39δ; CMR (CDCl₃) 157.66, 155.22, 140.45, 96.13, 94.64, 47.27, 46.41, 30.30, 29.94 and 25.52δ.

EXAMPLE 8

6-Phenyl-7-n-propyl-2,4-di-(1-pyrrolidinyl)-7H-pyrrolo[2,3-d]pyrimidine (VII)

Following the general procedure of EXAMPLE 6 and making non-critical variations but starting with 4-n-propylamino-2,6-di-1-pyrrolidino-pyrimidine (V, EXAMPLE 4, 3.85 g) and powdered α-bromoacetophenone (VI, 2.84 g), the title compound is obtained, mp at 83°; NMR (CDCl₃) 7.5–7.25, 6.38, 4.14, 3.79, 3.61, 1.95, 1.62 and 0.72δ; CMR (CDCl₃) 157.80, 155.44, 155.31, 133.82, 132.83, 128.29, 128.26, 126.66, 102.52, 101.29, 47.33, 46.44, 43.82, 25.54, 22.87 and 11.14δ.

EXAMPLE 9

7-Methyl-2,4-di-[N-methyl-N-(2-hydroxy)ethyl]-6-phenyl-7H-pyrrolo[2,3-d]pyrimidine (VII)

Following the general procedure of EXAMPLES 6–8 and making non-critical variations and using α-bromoacetophenone (VI, 1.18 g) and 2,6-bis-(2-hydroxyethyl)methylamino-4-methylaminopyrimidine (V, EXAMPLE 5, 1.5 g) the title compound is obtained, NMR (CDCl₃) 7.5–7.3, 6.44, 3.90, 3.78, 3.62, 3.44 and 3.23δ.

The methanesulfonic acid salt of the title compound is obtained as a hygroscopic solid.

EXAMPLE 10

2-[(2,6-Dichloropyrimidin-4-yl)amino]ethanol (III)

Following the general procedure of EXAMPLE 1 and making non-critical variations but starting with ethanolamine (II, 1.65 ml) and 2,4,6-trichloropyrimidine (I, 5.00 g), the title compound is obtained, NMR (CDCl₃) 6.33, 3.86, 3.59, 1.59δ.

EXAMPLE 11

2-[(2,6-Di-(1-pyrrolidinyl)pyrimidin-4-yl)amino]ethanol (V)

Following the general procedure of EXAMPLE 3 and making non-critical variations but starting with pyrrolidine (IV, 10.0 ml) and 2-[(2,6-Dichloropyrimidin-4-yl)amino]ethanol (III, EXAMPLE 10, 2.77 g), the title compound is obtained, mp 138°–140°; IR (mineral oil) 1600, 1571, 1508, 1476, 1449, 1432, 1417, 1343 cm⁻¹; NMR (CDCl₃) 5.9–6.6, 4.8–5.1, 4.76, 3.74, 3.25–3.6, 1.7–2.0δ; MS (m/z) 277, 249, 233 and 205.

EXAMPLE 12

2-[6-Phenyl-2,4-di-1-pyrrolidinyl-7H-pyrrolo[2,3-d]pyrimidin-7-yl]ethanol hydrochloride (VII-salt)

Following the general procedure of EXAMPLE 6 and making non-critical variations but starting with 2-[(2,6-di-(1-pyrrolidinyl)pyrimidin-4-yl)amino]ethanol (V, EXAMPLE 11, 2.00) and 2-bromoacetophenone (VI, 1.46 g), the free base of the title compound is obtained, mp 156°–157°; IR (mineral oil) 2953, 2924, 2860, 1572, 1529, 1478, 1473, 1453, 1449, 753 cm⁻¹; NMR (CDCl₃) 7.84, 7.25–7.5, 6.40, 4.1–4.2, 3.95–4.05, 3.79, 3.59 and 1.9–2.1δ; MS (m/z) 377, 346, 333, 305 and 188.

The hydrochloride salt is prepared in methanol and crystallized from hot acetone to provide the title compound, mp 131°–133°.

EXAMPLE 13

2-[6-Phenyl-2,4-di-1-pyrrolidinyl-7H-pyrrolo[2,3-d]pyrimidin-7-yl]ethyl methanesulfonate (VII-salt)

Methanesulfonyl chloride (0.25 ml) is added to a mixture of 2-[6-phenyl-2,4-di-1-pyrrolidinyl-7H-pyrrolo[2,3-d]pyrimidin-7-yl]ethanol (VII, EXAMPLE 12, 0.83 g), triethylamine (1.0 ml) and THF (20 ml) at 0°. The mixture is stirred at 0° for 1 hour, quenched with ice, and concentrated. Aqueous workup (ethyl acetate, saline wash, magnesium sulfate) gives the title compound as a solid; NMR (CDCl₃) 7.3–7.5, 6.41, 4.63, 4.43, 3.7–3.85, 3.5–3.75, 2.65, 1.9–2.1 δ.

EXAMPLE 14

2-[6-Phenyl-2,4-di-1-pyrrolidinyl-7H-pyrrolo[2,3-d]pyrimidin-7-yl]-S-ethyl-1-thioacetate (VII)

Thiolacetic acid (0.60 ml) is added to a mixture of 2-[6-phenyl-2,4-di-1-pyrrolidinyl-7H-pyrrolo[2,3-d]pyrimidin-7-yl]ethyl methanesulfonate (VII, EXAMPLE 13, 0.95 g), potassium carbonate (0.58 g), and acetonitrile (10 ml) at 0°. The mixture is allowed to warm to 20°–25° and is heated at reflux for 2 hr. After cooling to 20°–25°, basic workup (ethyl acetate, 1N potassium bicarbonate, saline wash, magnesium sulfate) and purification by flash chromatography eluting with ethyl acetate/hexane (4/96), pooling and concentrating the desired fractions gives the title compound, IR (mineral oil) 2968, 2951, 2925, 2869, 2860, 1689, 1566, 1516, 1470, 1452 and 756 cm$^{-1}$; NMR (CDCl$_3$) 7.25–7.5, 6.39, 4.34, 3.75–3.85, 3.55–3.65, 3.24, 2.16 and 1.9–2.1δMS (m/z) 435, 393, 333 and 43.

EXAMPLE 14A

2-[6-Phenyl-2,4-di-1-pyrrolidinyl-7H-pyrrolo[2,3-d]pyrimidin-7-yl]ethanethiol (VII)

Sodium hydroxide (300 mg) is added to a mixture of 2-[6-phenyl-2,4-di-1-pyrrolidinyl-7H-pyrrolo[2,3-d]pyrimidin-7-yl]-S-ethyl-1-thioacetate (VII, EXAMPLE 14, 240 mg), ethanol (11.5 ml), and water (2.9 ml, deoxygenated with argon). The mixture is heated at reflux for 80 rain and is allowed to cool to 20°–25°. Concentration, aqueous workup (methylene chloride, sodium sulfate), and purification by flash chromatography eluting with ethyl acetate/hexane (5/95), pooling and concentrating the desired fractions gives the title compound, IR (mineral oil) 2963, 2948, 2929, 2866, 1563, 1518, 1484, 1469, 1455, 1415, 1355, 754 cm$^{-1}$; NMR (CDCl$_3$) 7.2–7.5, 6.39, 4.2–4.5, 3.4–3.9, 2.83, 1.8–2.1δ; MS (m/z) 393, 360, 346, 333, 305.

EXAMPLE 15

2-[6-phenyl-2,4-di-1-pyrrolidinyl-7H-pyrrolo[2,3-d]pyrimidin-7-yl]ethyl acetate (VII)

Prepared by standard methods to give the title compound as a solid, mp 145°–148°; IR (mineral oil) 2953, 2924, 2866, 2855, 1742, 1569, 1519, 1471, 1456, 1448, 1233 cm$^{-1}$; $^1$H NMR (CDCl$_3$) 7.25–7.5, 6.41, 4.43, 4.30, 3.7–3.85, 3.55–3.65, 1.85–2.1, 1.82δ; MS m/z 419, 391, 376, 333, 209.

EXAMPLE 16

4-tert-Butylamino-2,6-dichloropyrimidine (III)

Tert-butylamine (II, 6.23 ml) is slowly added to 2,4,6-trichloropyrimidine (I, 10.0 g) at −20° (temp. rose to −14°). Diisopropylethylamine (9.50 ml) is added and the mixture is stirred at 20°–25° for 72 hours. Basic workup (ethyl acetate, 1N potassium bicarbonate, magnesium sulfate) and purification by flash chromatography eluting with hexane/ethyl acetate (9/1), pooling and concentrating the desired fractions gives the title compound, mp 192°–193°; NMR (CDCl$_3$) 6.29, 1.44δ.

EXAMPLE 17

4-tert-Butylamino-2,6-di-(1-pyrrolidinyl)pyrimidine (V)

Pyrrolidine (IV, 10.0 ml) is added to 4-tert-butylamino-2,6-dichloropyrimidine (III, EXAMPLE 16, 3.55 g) at −10°, and the mixture heated at reflux for 30 hours. After cooling to 20°–25°, basic workup (ethyl acetate, 1N potassium bicarbonate, saline wash, magnesium sulfate) gives the title compound as a liquid; NMR (CDCl$_3$) 4.78, 4.26, 3.3–3.6, 1.85–2.0 and 1.41δ.

EXAMPLE 18

7-tert-Butyl-6-phenyl-2,4-di-1-pyrrolidinyl-7H-pyrrolo[2,3-d]pyrimidine (VII)

2-Bromoacetophenone (VI, 1.4 g) is added to a mixture of diisopropylethylamine (1.5 ml) and 4-tert-butylamino-2,6-di-(1-pyrrolidinyl)pyrimidine (V, EXAMPLE 17, 2.0 g) in acetonitrile (60 ml) at 0°. The mixture is allowed to warm to 20°–25° and is then heated at reflux for 115 hr. After cooling to 20°–25°, basic workup (methylene chloride, 1N potassium bicarbonate, magnesium sulfate), and purification by flash chromatography eluting with ethyl acetate/hexane (5/95), and pooling the desired fractions gives the title compound, mp 87°–89°; IR (mineral oil) 2960, 2925, 2856, 1577, 1561, 1510, 1467, 1453, 1388, 1360 cm$^{-1}$; NMR (CDCl$_3$) 7.25–7.45, 6.15, 3.7–3.8, 3.55–3.65, 1.85–2.05, 1.62δ; MS (m/z) 389, 333, 305.

EXAMPLE 19

6-Phenyl-2,4-di-1-pyrrolidinyl-7H-pyrrolo[2,3-d]pyrimidine (VII)

Trifluoroacetic acid (18.0 ml) is slowly added to a mixture of 7-tert-butyl-6-phenyl-2,4-di-1-pyrrolidinyl-7H-pyrrolo[2,3-d]pyrimidine (VII, EXAMPLE 18, 1.2 g) and methylene chloride (4.0 ml) at 0°. The mixture is permitted to warm to 20°–25° and the resulting mixture is stirred at 20°–25° for 4 hr. Concentration and basic workup (chloroform, 1N sodium hydroxide, sodium sulfate) gives the title compound; IR (mineral oil) 2954, 2924, 2855, 1611, 1595, 1566, 1548, 1519, 1483, 1470, 1456 cm$^{-1}$; NMR (CDCl$_3$) 10.45, 7.49, 7.32, 7.17, 6.68, 3.83, 3.57, 2.02, 1.8–2.0δ; MS (m/z) 333, 305, 291, 278, 264, 166.

EXAMPLE 20

7-tert-Butyl-6-(4-methoxyphenyl)-2,4-di-1-pyrrolidinyl-7H-pyrrolo[2,3-d]pyrimidine (VII)

Following the general procedure of EXAMPLE 1 and making non-critical variations but starting with 2-bromo-4'-methoxyacetophenone (VI, 2.37 g) and 4-tert-butylamino-2,6-di-(1pyrrolidinyl)pyrimidine (V, EXAMPLE 17, 3.00 g), the title compound is obtained, mp 204°–206°; IR (mineral oil) 2953, 2926, 2858, 1586, 1579, 1561, 1553, 1510, 1467, 1452, 1444 cm$^{-1}$; NMR (CDCl$_3$) 7.29, 6.85, 6.13, 3.84, 3.65–3.80, 3.5–3.65, 1.85–2.0, 1.61δ; MS m/z 419, 363, 348, 335.

EXAMPLE 21

6-(4—Hydroxyphenyl)-2,4-di-1-pyrrolidinyl-7H-pyrrolo[2,3-d]pyrimidine (VII) and

EXAMPLE 22

6-(4-methoxyphenyl)-2,4-di-1-pyrrolidinyl-7H-pyrrolo[2,3-d]pyrimidine (VII)

Hydrogen bromide (5.0 ml, 48% aq.) is used to dissolve 7-tert-butyl-6-(4-methoxyphenyl)-2,4-di-1-pyrrolidinyl-7H-pyrrolo[2,3-d]pyrimidine (VII, EXAMPLE 20, 0.21 g) and the mixture heated at 120° for 30 min. After cooling to 20°–25°, concentration, aqueous workup (ethyl acetate, ammonium hydroxide, water, saline washes, magnesium sulfate) and purification by flash chromatography eluting with hexane/ethyl acetate (3/1). The appropriate fractions are pooled and concentrated to give the title compound, 6-(4-methoxyphenyl)-2,4-di-1-pyrrolidinyl-7H-pyrrolo[2,3-d]pyrimidine, mp 203°–205°; IR (mineral oil) 2955, 2925, 2864, 2857, 1617, 1564, 1518, 1500, 1485, 1472, 1457 cm$^{-1}$; NMR (CDCl$_3$) 9.25, 7.41, 6.90, 6.56, 3.82, 3.7–3.9, 3.5–3.65, 1.85–2.1 δ; MS m/z 363, 335, 320, 308, 181.

Further elution provides 6-(4-hydroxyphenyl)-2,4-di-1-pyrrolidinyl-7H-pyrrolo[2,3d]pyrimidine as a solid, IR (mineral oil) 2954, 2924, 2856, 1602, 1581, 1567, 1554, 1525, 1499, 1455 cm$^{-1}$; NMR (d$_6$-DMSO) 11.32, 9.40, 7.57, 6.73, 6.64, 3.6–3.8, 3.45–3.55, 1.8–2.0 δ; MS (m/z) 349, 321, 294, 174.

EXAMPLE 23

4-Methyl-2,6-di-(1-thiomorpholinyl)pyrimidine (V)

Thiomorpholine (IV, 4.30 g) is added to a mixture of 2,6-dichloro-4-methylaminopyrimidine (III, EXAMPLE 1, 1.5 g), diisopropylethylamine (7.3 ml) and acetonitrile (16.8 ml) at 20°–25°. The mixture is heated at reflux for 24 hours. After cooling to 20°–25°, concentration, basic workup (ethyl acetate, 1N potassium bicarbonate, magnesium sulfate) and purification by flash chromatography eluting with ethyl acetate/hexane (20/80). The appropriate fractions are pooled and concentrated, NMR (CDCl$_3$) 5.69, 4.69, 4.08, 2.89, 2.6–2.7 δ.

Thiomorpholine (1.18 g) is added to a mixture of the mono substituted product (1.87 g) and pyridine (3.8 ml) and the mixture heated in a bomb at 150° for 41 hours. Concentration, basic workup (ethyl acetate, 1N potassium bicarbonate, magnesium sulfate) and purification by flash chromatography eluting with ethyl acetate/hexane (20/80). The appropriate fractions are pooled and concentrated to give the title compound, NMR (CDCl$_3$) 4.90, 4.3–4.5, 3.95–4.1, 3.8–3.95, 2.85, 2.5–2.7 δ.

EXAMPLE 24

7-Methyl-6-phenyl-2,4-di-1-thiomorpholinyl-7H-pyrrolo[2,3-d]pyrimidine (VII)

Following the general procedure of EXAMPLE 6 and making non-critical variations but starting with 2-bromoacetophenone (VI, 0.902 g) is added to a mixture of 4-methyl-2,6-di-(1-thiomorpholinyl)pyrimidine (V, EXAMPLE 23, 1.38 g), the title compound is obtained, mp 133°–135°; IR (mineral oil) 2929, 2867, 2855, 1585, 1555, 1507, 1464, 1449, 1377, 1367, 949 cm$^{-1}$; NMR (CDCl$_3$) 7.25–7.5, 6.29, 4.1–4.25, 3.66, 2.6–2.8 δ; MS (m/z) 411, 378, 364, 350, 338.

EXAMPLE 25

6-Phenyl-7-[2-(1-piperazinyl)ethyl]-2,4-di-1-pyrrolidinyl-7H-pyrrolo[2,3-d]pyrimidine maleate (VII-salt)

A slurry of piperazine (4.85 g) and acetonitrile (25 ml) is added to a suspension of 2-[6-phenyl-2,4-di-1-pyrrolidinyl-7H-pyrrolo[2,3-d]pyrimidin-7-yl]ethyl methanesulfonate (VII, EXAMPLE 13, 0.558 g), potassium carbonate (0.641 g), sodium iodide (0.005 g) and acetonitrile (25 ml) at 20°–25°. The mixture is heated at reflux for 16.5 hours. After cooling to 20°–25°, basic workup (methylene chloride, 1N potassium bicarbonate, sodium sulfate) and purification by flash chromatography eluting with methanol/methylene chloride (10/90). The appropriate fractions are pooled and concentrated to give the free base corresponding to the title compound, NMR (CDCl$_3$) 7.2–7.55, 6.38, 4.29, 3.65–3.9, 3.5–3.65, 2.7–2.9, 2.58, 2.45, 1.8–2.1 δ.

The maleic acid salt is prepared in methanol and methylene chloride. Concentration and trituration (acetone) gives the title compound, mp 181°–183°; IR (mineral oil) 2954, 2925, 2855, 1574, 1517, 1484, 1474, 1451, 1424, 1376, 1361, 750 cm$^{-1}$; MS (m/z) 445, 333, 305.

EXAMPLE 26

7-[2-(1-Morpholinyl)ethyl]-6-phenyl-2,4-di-1-pyrrolidinyl-7H-pyrrolo[2,3-d]pyrimidine maleate (VII-salt)

A mixture of morpholine (4.85 g) in acetonitrile (23 ml) is added to a mixture of 2-[6-phenyl-2,4-di-1-pyrrolidinyl-7H-pyrrolo[2,3-d]pyrimidin-7-yl]ethyl methanesulfonate (VII, EXAMPLE 13, 0.530 g), sodium iodide (10.0 mg), potassium carbonate (0.641 g) and acetonitrile (23 ml) at 20°–25°. The mixture is heated at reflux for 21.5 hr. After cooling to 20°–25°, basic workup (1N potassium carbonate, methylene chloride, sodium sulfate) and purification by flash chromatography eluting with acetone/methylene chloride (5/95). The appropriate fractions are pooled and concentrated to give the the free base corresponding to the title compound, NMR (CDCl$_3$) 7.25–7.55, 6.38, 4.29, 3.7–3.9, 3.5–3.7, 2.59, 2.3–2.45, 1.85–2.1 δ.

The maleic acid salt is prepared in methanol and methylene chloride. Concentration and trituration (ethyl acetate) gives the title compound as a solid, mp 169.5°–171°; IR (mineral oil) 953, 2925, 2856, 1616, 1586, 1570, 1542, 1524, 1488, 1481, 1455, 1378, 1353 cm$^{-1}$; MS (m/z) 446, 333.

EXAMPLE 27

7-[2-(1-(4-Methyl)piperazinyl)ethyl]-6-phenyl-2,4-di-1-pyrrolidinyl-7H-pyrrolo[2,3-d]pyrimidine maleate (VII-salt)

A mixture of 1-methylpiperazine (5.64 g) in acetonitrile (25 ml) is added to a mixture of 2-[6-phenyl-2,4-di-1-pyrrolidinyl-7H-pyrrolo[2,3-d]pyrimidin-7-yl]ethyl methanesulfonate (VII, EXAMPLE 13, 0.556 g), sodium iodide (10.0 mg), potassium carbonate (0.641 g) and acetonitrile (25 ml) at 20°–25°. The mixture is heated at reflux for 7 hours. After cooling to 20°–25°, basic workup (1N potassium carbonate, methylene chloride, sodium sulfate) and purification by flash chromatography eluting with methanol/methylene chloride (5/95). The appropriate fractions are pooled and concentrated to give the the free base corresponding to the title compound, NMR (CDCl$_3$) 7.25–7.5, 6.37, 4.28, 3.7–3.9, 3.60, 2.62, 2.2–2.7, 2.26, 1.85–2.1 δ.

The maleic acid salt is prepared in methanol (20 ml), mp 159°–162°; IR (mineral oil) 954, 2925, 2868, 2856, 1571, 1564, 1518, 1483, 1467, 1456, 1419, 1377, 1356 cm$^{-1}$; MS (m/z) 459, 389, 333.

EXAMPLE 28

2-[6-(4-Methoxyphenyl)-2,4-di-1-pyrrolidinyl-7H-pyrrolo[2,3-d]pyrimidin-7-yl]ethanol hydrochloride (VII-salt)

Following the general procedure of EXAMPLE 61 and making non-critical variations but starting with 2-bromo-4'-methoxyacetophenone (VI, 0.825 g) and 2-[(2,6-di-(1-pyrrolidinyl)pyrimidin-4-yl)amino]ethanol (V, EXAMPLE 11, 1.0 g) the free base corresponding to the title compound is obtained, mp 211.5°–213°: IR (mineral oil) 2954, 2924, 2854, 1571, 1528, 1496, 1484, 1474, 1457, 1446, 1250, 776 cm$^{-1}$; NMR (CDCl$_3$) 7.87, 7.25–7.35, 6.95, 6.33, 4.05–4.2, 3.95–4.05, 3.85, 3.7–3.9, 3.5–3.65, 1.8–2.1 δ; MS (m/z) 407, 379, 376, 363.

The hydrochloride salt is prepared in methylene chloride and methanol, mp 175°–177°; MS (m/z) 407, 376, 363, 348, 203.

EXAMPLE 29

2-[6-(4—Hydroxyphenyl)-2,4-di-1-pyrrolidinyl-7H-pyrrolo[2,3-d]pyrimidin-7-yl]ethanol hydrochloride (VII-salt)

2-[6-(4-methoxyphenyl)-2,4-di-1-pyrrolidinyl-7H-pyrrolo[2,3-d]pyrimidin-7-yl]ethanol (VII, EXAMPLE 28, 0.204 g) is heated at 120° in aqueous hydrogen bromide (48%, 5 ml) for 0.5 hours. After cooling to 20°–25°, concentration, basic workup (ethyl acetate, ammonium hydroxide, magnesium sulfate) and purification by flash chromatography eluting with methanol/methylene chloride (2/98), pooling and concentrating the appropriate fractions gives the free base corresponding to the title compound, NMR (CDCl$_3$) 7.21, 6.88, 6.32, 4.05–4.15, 3.95–4.05, 3.78, 3.5–3.65, 1.8–2.1δ; MS (m/z) 393, 365, 362, 349, 321, 196.

The hydrochloride salt is prepared in methylene chloride and methanol, mp 258°–259°; IR (mineral oil) 3057, 3034, 3014, 1619, 1613, 1545, 1450, 1271 cm$^{-1}$; MS (m/z) 393, 362, 349, 338, 321, 196.

EXAMPLE 30

2-[6-Methyl-2,4-di-1-pyrrolidinyl-7H-pyrrolo[2,3-d]pyrimidin-7-yl]ethanol (VII)

Chloroacetone (VI, 2.44 g) is added to a mixture of 2-[(2,6-di-(1-pyrrolidinyl)pyrimidin-4-yl)amino]ethanol (V, EXAMPLE 11, 5.50 g), diisopropylethylamine (6.00 ml), lithium bromide (2.31 g) and acetonitrile (200 ml) at 20°–25°. The mixture is heated at reflux for 19.5 hours. After cooling to 20°–25°, basic workup (methylene chloride, 1N potassium bicarbonate, sodium sulfate), and purification by flash chromatography eluting with methanol/methylene chloride (1/99→2/98). The appropriate fractions are pooled and concentrated to give the title compound, NMR (CDCl$_3$) 7.65, 6.09, 4.10, 3.93, 3.74, 3.55, 2.26, 1.8–2.1δ.

EXAMPLE 31

2-[6-Methyl-2,4-di-1-pyrrolidinyl-7H-pyrrolo[2,3-d]pyrimidin-7-yl]ethyl methanesulfonate (VII-salt)

Methanesulfonyl chloride (0.67 ml) is added to a mixture of 2-[6-methyl-2,4-di-1-pyrrolidinyl-7H-pyrrolo[2,3-d]pyrimidin-7-yl]ethanol (VII, EXAMPLE 30, 2.70 g), triethylamine (1.2 ml), and methylene chloride (32 ml) at 20°–25° and the mixture stirred for 2 hours. Basic workup (1N potassium bicarbonate, methylene chloride, sodium sulfate) gives the title compound, mp 141°–143°; NMR (CDCl$_3$) 6.07, 4.60, 4.29, 3.72, 3.55, 2.60, 2.31, 1.8–2.05δ.

EXAMPLE 32

6-Methyl-7-[2-(1-morpholinyl)ethyl]-2,4-di-1-pyrrolidinyl-7H-pyrrolo[2,3-d]pyrimidine maleate (VII-salt)

A mixture of morpholine (10.4 g) in acetonitrile (25 ml) is added to a mixture of 2-[6-methyl-2,4-di-1-pyrrolidinyl-7H-pyrrolo[2,3-d]pyrimidin-7-yl]ethyl methanesulfonate (VII, EXAMPLE 31, 0.875 g), sodium iodide (10.0 mg), potassium carbonate (1.18 g) and acetonitrile (25 ml) at 20°–25°. The mixture is heated at reflux for 7 hours. After cooling to 20°–25°, basic workup (1N potassium carbonate, methylene chloride, sodium sulfate) and purification by flash chromatography eluting with methanol/methylene chloride (5/95) and pooling the desired fractions gives the free base corresponding to the title compound, NMR (CDCl$_3$) 6.06, 4.14, 3.6–3.8, 3.56, 2.65, 2.5–2.7, 2.31, 1.85–2.05δ.

The maleic acid salt is prepared in methanol and methylene chloride, mp 162°–165°; IR (mineral oil) 1621, 1577, 1560, 1524, 1469, 1356, 872 cm$^{-1}$; MS (m/z) 384, 271.

EXAMPLE 33

6-Methyl-7-[2-(1-(4-methyl)piperazinyl)ethyl]-2,4-di-1-pyrrolidinyl-7H-pyrrolo[2,3-d]pyrimidine maleate (VII-salt)

A mixture of 1-methylpiperazine (11.9 g) in acetonitrile (25 ml) is added to a mixture of 2-[6-methyl-2,4-di-1-pyrrolidinyl-7H-pyrrolo[2,3-d]pyrimidin-7-yl]ethyl methanesulfonate (VII, EXAMPLE 31, 0.875 g), sodium iodide (10.0 mg), potassium carbonate (1.18 g) and acetonitrile (25 ml) at 20°–25°. The mixture is heated at reflux for 7 hours. After cooling to 20°–25°, basic workup (1N potassium carbonate, methylene chloride, sodium sulfate) and purification by flash chromatography eluting with methanol/methylene chloride (5/95) and pooling the desired fractions gives the free base corresponding to the title compound, NMR (CDCl$_3$) 6.05, 4.14, 3.65–3.85, 3.56, 2.65, 2.2–2.8, 2.30, 1.8–2.1δ.

The maleic acid salt is prepared in methanol and methylene chloride, mp 187°–188°; IR (mineral oil) 1576, 1559, 1521, 1358, 866 cm$^{-1}$; MS (m/z) 397, 327, 271.

EXAMPLE 34

6-Methyl-7-[2-(1-piperazinyl)ethyl)]-2,4.di-1-pyrrolidinyl-7H-pyrrolo[2,3-d]pyrimidine maleate (VII-salt)

A mixture of piperazine (10.3 g) in acetonitrile (25 ml) is added to a mixture of 2-[6-methyl-2,4-di-1-pyrrolidinyl-7H-pyrrolo[2,3-d]pyrimidin-7-yl]ethyl methanesulfonate (VII, EXAMPLE 31, 0.875 g), sodium iodide (10.0 mg), potassium carbonate (1.18 g) and acetonitrile (25 ml) at 20°–25°. The mixture is heated at reflux for 7 hr. After cooling to 20°–25°, basic workup (1N potassium carbonate, methylene chloride, sodium sulfate) and purification by flash chromatography eluting with methanol/methylene chloride (5/95), pooling and concentrating the desired fractions gives the free base corresponding to the title compound, NMR (CDCl$_3$) 6.05, 4.15, 3.73, 3.56, 2.91, 2.64, 2.4–2.75, 2.31, 1.7–2.1δ.

The maleic acid salt is prepared in methanol, mp 168°–171°; IR (mineral oil) 1645, 1571, 1558, 1520, 1424, 1356 cm$^{-1}$; MS (m/z) 383, 271.

EXAMPLE 35

2-[6-Phenyl-2,4.di-1-pyrrolidinyl-7H-pyrrolo[2,3-d]pyrimidin-7-yl]acetophenone

2-Bromoacetophenone (0.699 g) is added to a mixture of diisopropylethylamine (0.19 ml), and 2-[2,6-di-1-pyrrolidinylpyrimidin-4-yl]aminoacetophenone (200 mg) in acetonitrile (10 ml) at −2°. After stirring for 40 min at −2° the mixture is allowed to warm to 20°–25° and is stirred for 18 h. Basic workup (methylene chloride, 1N potassium bicarbonate, magnesium sulfate) and purification by flash chromatography eluting with 2%→10% methanol: methylene chloride and pooling the appropriate fractions gives the title compound. An analytical sample is prepared by crystallization from methylene chloride-acetone-hexane to give the product as a solid; IR (mineral oil) 2954, 2924, 2871, 2855, 1701, 1684, 1613, 1600, 1590, 1582, 1454, 1444 cm$^{-1}$; $^1$H NMR (CDCl$_3$) 8.28, 8.02, 7.5–7.7, 7.38, 7.2–7.3, 6.72, 3.7–4.05, 3.58, 2.18, 1.6–2.15δ; MS m/z 451,346, 332, 105.

EXAMPLE 36

7-Methyl-6-phenyl-2,4-di-1-pyrrolidinyl-7H-pyrrolo[2,3-d]pyrimidine, methanesulfonate (VII-salt)

A suspension of 6-phenyl-2,4-di-(1-pyrrolidinyl)-7-methyl-7H-pyrrolo[2,3-d]pyrimidine (VII, EXAMPLE 6, 500 mg) in 50 ml of 2-propanol/water (95/5) is treated with 4.7 ml of a 0.308M methanesulfonic acid mixture in 2-propanol/ water (95/5), and the reaction mixture is stirred at 20°–25° for 1 hour. The reaction mixture became homogenous within 1 hr. The reaction mixture is filtered and then concentrated under reduced pressure. The crude product s triturated with ethyl acetate/hexane (1:1, 70 ml) at 5° for 30 mm in the dark. The solid is isolated in the dark and dried in a vacuum oven (24 hr, 0.005 mm, 40°) to give the title compound, mp 177°–178°; recrystallization from ethanol/ethyl acetate, mp 180°–181°; NMR (CDCl$_3$, TMS) 12,07, 7.55–7.35, 6.45, 4.05–3.60, 2.80 and 2.22–1.90δ; CMR (CDCl$_3$, TMS) 154.7, 149.3, 141.5, 135.3, 130.8, 129.1, 128.7, 128.3, 102.1, 97.0, 48.6, 48.4, 48.2, 39.6, 33.4, 26.2, 25.3 and 24.0δ.

EXAMPLE 37

6-Phenyl-7-phenylmethyl-2,4-di-1-pyrrolidinyl-7H-pyrrolo [2,3-d]pyrimidine (VII)

A stirred mixture of 4-chloro-2,6-di-1-pyrrolidinylpyrimidine IV, J. Med. Chem., 33, 1145 (1990), 253 mg] and benzylamine (1 ml) is heated at 140° for 48 hr under nitrogen. The mixture is then cooled to 20°–25°, poured into aqueous sodium bicarbonate, and extracted with ethyl acetate/hexane (1/1). The extracts are washed with saline, dried over anhydrous sodium sulfate and evaporated, and the crude product is chromatographed on silica gel (20 g). The column is packed and eluted with ethyl acetate/hexane (50/50, 250 d fractions). Fractions 22–44 are combined to give the 6-benzylamino intermediate, NMR (CDCl$_3$, TMS) 7.34–7.24, 4.72, 4.44–4.42, 3.54–3.38 and 1.91–1.86δ; MS (m/z) M$^+$ observed at m/z 323.2121, calc'd for C$_{19}$H$_{25}$N$_5$, 323.2110.

A mixture of 6-benzylamino intermediate (150 mg) from the preceding paragraph in acetonitrile (3 ml) is cooled to 0° and treated with diisopropylethylamine (0.1 ml), followed by phenacyl bromide (VI, 93 mg). The resulting mixture is stirred at 0° for 1 hr and 25° for 66 hr, then diluted with acetonitrile (20 ml) and heated at reflux for 4 hr, all under an atmosphere of nitrogen. The reaction mixture is cooled to 20°–25° and the acetonitrile is removed under reduced pressure. The residue is partitioned between ethyl acetate and water/saturated aqueous sodium bicarbonate (1/1). The organic layers are separated, combined and dried over sodium sulfate and evaporated. The crude solid product is recrystallized from ethyl acetate (4 ml). The solids are isolated by filtration, washed with ethyl acetate (–20°, 3×2 ml), and dried (2 hr, 0.05 mm, 40°), thereby giving the title compound, mp 173°–175°; NMR (CDCl$_3$, TMS) 7.30–7.02, 6.44, 5.36, 3,80, 3.58, and 2.05–1.89δ; MS (m/z) M$^+$ observed at m/z 423.2440, calc'd for C$_{27}$H$_{29}$N$_5$, 423.2423, other ions observed at (m/z) 395, 381,368, 354, 332, 304, 263, 140, 91.

EXAMPLE 38

6,7-Diphenyl-2,4-di-1-pyrrolidinyl-7H-pyrrolo[2,3-d]pyrimidine (VII)

A mixture of 4-chloro-2,6-di-1-pyrrolidinylpyrimidine IV, J. Med. Chem., 33, 1145 (1990), 253 mg] in aniline (1 ml) is heated at 140° for 16 hours under nitrogen. The reaction mixture is cooled, diluted with methylene chloride (100 ml) and put onto a 75 g column of silica gel. The column is wrapped in foil and eluted without lights in the room (i.e. only ambient light from outdoors), since the product appeared to be rather photosensitive. Fractions of 90 ml are collected rapidly using house vacuum to speed the elution. The column is eluted with methylene chloride (500 ml), then with ethyl acetate/methylene chloride (5/95 50 ml, 10/90 100 ml and 20/80 500 ml).

Fractions 14–30 are homogeneous by TLC and upon combination giveed a N-phenyl intermediate. Due to its photosensitivity, this material is used immediately in the next reaction without any characterization. All of this material is dissolved in acetonitrile (8 ml), then treated at 20°–25° with diisopropylethylamine (0.26 ml) and phenacyl bromide (VI, 200 mg). The mixture is stirred at 25° for 16 hours and 70° for 1 hour, then diluted with acetonitrile (50 ml) and heated at reflux for 4 hours. Following removal of the solvent, the residue is partitioned between dilute aqueous sodium bicarbonate and chloroform. The organic layer is dried and concentrated, and the crude product (500 mg) is chromatographed on silica gel (55 g). The column is packed and eluted with acetone/methylene chloride (3/97). The appropriate fractions are pooled and concentrated. Recrystallization from ethyl acetate yielded the title compound, mp 206°–207°; NMR (CDCl$_3$, TMS) 7.34–7.18, 6.64, 3.83, 3.53, 2.01–1.86δ; MS (m/z) M$^+$ observed=409.2288, calc'd for C$_{26}$H$_{27}$N$_5$=409.2266, other ions observed 381,367, 352, 340, 326, 311,297, 284, 270, 204.

EXAMPLE 39

N-Methyl-2,6-di-4-morpholinyl-4-pyrimidinamine (V)

A mixture of 2,6-dichloro-4-methylaminopyrimidine (III, EXAMPLE 1, 2 g) dissolved in 29 ml of morpholine (IV) is refluxed for 18 hours. The reaction mixture is concentrated under reduced pressure. The resulting residue is partitioned between chloroform and saturated sodium bicarbonate. The organic layer is separated, washed with saline, dried over anhydrous sodium sulfate, and concentrated under reduced pressure. The crude product is recrystallized from hexane and the solid is isolated and dried (18 hr, 0.05 mm, 40°), to give the title compound, mp 127°–128°; IR (mineral oil) 2956, 2952, 2925, 2898, 2855, 1591, 1571, 1494, 1465, 1451, 1443, 1424, 1365, 1258, 1236, 1213, 1194, 1113, 1007 and 789 cm$^{-1}$; NMR (CDCl$_3$, TMS) 7.55–7.3, 6.36, 4.0–3.75 and 3.68δ; MS (m/z) calc'd for C$_{13}$H$_{21}$N$_5$O$_2$, M$^+$=279.1695, found=279.1707, other ions=262, 248, 234, 222, 204, 192, 164, 124 and 81.

EXAMPLE 40

7-Methyl-2,4-di-4-morpholinyl-6-phenyl-7H-pyrrolo[2,3-d] Pyrimidine (VII)

A mixture of N-methyl-2,6-di-4-morpholinyl-4-pyrimidinamine (V, EXAMPLE 39, 1.4 g) dissolved in 95 ml of acetonitrile is treated with 1.11 ml of N,N-diisopropylethylamine followed by 0.997 g of 2-bromoacetophenone. The reaction mixture is stirred at 20°–25° for 66 hours and refluxed for 8 hours. The reaction mixture is concentrated under reduced pressure. The resulting residue is partitioned between chloroform and saturated sodium bicarbonate. The organic layer is separated, washed with saline, dried over anhydrous sodium sulfate, and concentrated under reduced pressure.

The crude product (2.03 g) is chromatographed on 180 g of silica gel. The column is packed and eluted with chloroform/acetone (95/5). An initial fraction of 200 ml is collected, followed by 8 ml fractions. Based on their TLC homogeneity, fractions 57–120 are combined. The solid is recrystallized from chloroform/hexane, isolated and dried under reduced pressure with heat (18 hours, 0.4 mm, 42°), to give the title compound, mp 208°–2090; IR (mineral oil) 953, 2924, 2856, 1584, 1472, 1559, 1538, 1498, 1480, 1459, 1442, 1397, 1377, 1365, 1308, 1261, 1245, 1232, 1209, 1118, 1011, 1003, 748, 623 and 602 cm$^{-1}$; NMR (CDCl$_3$, TMS) 7.55–7.3, 6.36, 4.0–3.75 and 3.68δ; MS (m/z) calc'd for C$_{21}$H$_{25}$N$_5$O$_2$, M$^+$=379.2008, found= 79.1997, other ions 348, 322, 304, 290, 276, 264, 236, 221,207, 189, 174 and 145.

EXAMPLE 41

1,1'-(7-Methyl-6-phenyl-7H-pyrrolo[2,3-d]pyrimidine-2,4-diyl)bis-3,4-pyrrolidinediol (VII)

The preparation of (S,S)-3,4-dihyroxypyrrolidine from (+)-tartaric acid is accomplished following literature precedent (N-benzyltartrimide formation; borane reduction; hydrogenation). A mixture containing 2,6-dichloro-4-methylaminopyrimidine (III, EXAMPLE 1,424 mg) and (S,S)-3,4-dihydroxypyrrolidine (IV, 820 mg) in pyridine (8 ml) is heated at reflux under nitrogen for 36 hours. The mixture is cooled, the pyridine is removed under reduced pressure, and the residue is chromatographed on silica gel (280 g). The column is packed and eluted with 4M ammonia-methanol/chloroform (30/70) collecting 20 ml fractions. Fractions 45–56 are combined to give an intermediate completely clean by TLC, MS M$^+$ observed at m/z 311.

A mixture of the intermediate (423 mg) in dimethylformamide (5 ml) is treated with diisopropylethylamine (0.3 ml), followed by phenacyl bromide (270 mg). The resulting mixture is stirred at 25° for 18 hr, then diluted with acetonitrile (40 ml) and heated at reflux for 4 hr. When the reaction mixture is recooled to 20°–25°, solids precipitated. Filtration, washing with fresh acetonitrile (2×10 ml), and drying (18 hours, 0.05 mm, 40°) gives the title compound, mp 276°–278°; NMR (d$_6$-DMSO, TMS) 7.58–7.32, 6.54, 5.15, 4.99, 3.98–3.47δ; MS (m/z) M$^+$ observed=411.1919, calcd for C$_{21}$H$_{25}$N$_5$O$_4$=411.1906.

EXAMPLE 42

N-Methyl-2,6-di-(4'-t-butoxycarbonyl-1'-piperazinyl)-4-pyrimidinamine (V)

A mixture of 2,6-dichloro-4-methylaminopyrimidine (III, EXAMPLE 1, 5 g) dissolved in o-xylene (300 ml) is treated with mono-t-BOC-piperazine (IV, 20.92 g) and the reaction mixture is refluxed for 50 hr. The reaction mixture is concentrated under reduced pressure. The resulting residue is partitioned between chloroform and saturated sodium bicarbonate. The organic layer is separated, washed with saline, dried over anhydrous sodium sulfate, and concentrated under reduced pressure.

The crude product (24.53 g) is chromatographed on silica gel (590 g). The column is packed and eluted with chloroform/acetone (97/3). An initial fraction of 400 ml is collected followed by 8 ml fractions. Based on their TLC homogeneity, fractions 132–326 are combined and concentrated to give the title compound, NMR (CDCl$_3$, TMS) 4.94, 4.96, 3.75–3.65, 3.55–3.4, 2.85 and 1.48 8; MS (m/z) M$^+$ (found) 477, other ions at m/z 420, 376, 364, 348, 321,265, 221, 178, 164 and 57.

EXAMPLE 43

7-Methyl-6-phenyl-2,4-di- (4'-t-butoxycarbonyl-1'-piperazinyl)-7-H-pyrrolo[2,3-d]pyrimidine (VII-protected)

Following the general procedure of EXAMPLE 40 and making non-critical variations but starting with N-methyl-2,6-di-(4'-t-butoxycarbonyl-1'-piperazinyl)-4-pyrimidinamine (VII-protected, EXAMPLE 42, 4.65 g) and 2'-bromoacetophenone (VI), the title compound is obtained, mp 212°–213°; NMR (CDCl$_3$, TMS) 7.5–7.3, 6.35, 3.95–3.75, 3.68, 3.65–3.5 and 1.49δ; MS (m/z) M$^+$=577, other ions 521,477, 465, 421,365 and 57.

EXAMPLE 44

7-Methyl-6-phenyl-2,4-di-1-piperazinyl-7H-pyrrolo[2,3-d]pyrimidine (VII)

A mixture of 7-methyl-6-phenyl-2,4-di-4'-t-butoxycarbonyl-1'-piperazinyl)-7-H-pyrrolo[2,3-d]pyrimidine (VII, EXAMPLE 43, 200 mg) in hydrochloric acid (3.1M, 5 ml) in ethyl acetate is stirred at 20°–25° for 1 hr. The reaction mixture is concentrated under reduced pressure.

The crude product (169 mg) is chromatographed on silica gel (40 g). The column is packed and eluted with chloroform/5.0M ammonia in methanol (89/11). An initial fraction of 30 ml is collected, followed by 3 ml fractions. Based on their TLC homogeneity, fractions 27–35 are combined to give the title compound, mp 131°–135°; IR (mineral oil) 2953, 2926, 2869, 2854, 1581, 1573, 1558, 1508, 1485, 1467, 1440, 1399, 1377, 1370, 1314, 1307, 1258, 1245, 1002 and 750 cm$^{-1}$; NMR (CDCl$_3$, TMS) 7.5–7.3, 6.37, 3.8, 3.79, 3.67 and 3.05–2.9δ; MS (m/z) calc'd for C$_{21}$H$_{27}$N$_7$, M$^+$=377.2328, found=377.2332, other ions 347, 335, 321, 308 292, 278, 264, 252, 188 and 147.

EXAMPLE 45

7-Methyl-6-phenyl-2,4-di-1-piperazinyl-7H-pyrrolo[2,3-d]pyrimidine, trihydrochloride (VII-salt)

A mixture of 7-methyl-6-phenyl-2,4-di-4'-t-butoxycarbonyl-1'-piperazinyl)-7-H-pyrrolo[2,3-d]pyrimidine (VII, EXAMPLE 43, 200 mg, 0.35 mmol) in hydrochloric acid (3.1M, 5 ml) in ethyl acetate is stirred at 20°–25° for 40 min. The reaction mixture is concentrated under reduced pressure. The reaction mixture is filtered and washed several times with fresh ethyl acetate.

The solid is dried in a vacuum desiccator (66 hours, 0.1 mm, 40°) to give the title compound, mp 238°–242°; IR (mineral oil) 3415, 2953, 2925, 2867, 2855, 2700, 2640, 1621, 1594, 1556, 1533, 1484, 1461, 1451, 1376, 1334, 1288 and 1267 cm$^{-1}$; NMR (CDCl$_3$, TMS) 7.5–7.3, 6.37, 3.88, 3.79, 3.67 and 3.05–2.9 δ; MS (m/z) calc'd for C$_{21}$H$_{27}$N$_7$ (free base) M$^+$=377.2328, found=377.2322, other ions 347, 335, 321, 278, 264, 188, 146 and 79.

EXAMPLE 46

3,3'-[(7-Methyl-6-phenyl-7H-pyrrolo[2,3-d]pyrimidine-2, 4.diyl)di-1,4-piperazinediyl]bis-1,2-propanediol (VII)

A mixture of 7-methyl-6-phenyl-2,4-di-1-piperazinyl-7H-pyrrolo[2,3-d]pyrimidine (VII, EXAMPLE 44, 92 mg) in tolluene (10 ml) is treated with (+) glycidol (76 μl) and the reaction mixture is refluxed for 23 hr and concentrated under reduced pressure. The resulting residue is partitioned between chloroform and water. The organic layer is separated, washed with saline, dried over anhydrous sodium sulfate, and concentrated under reduced pressure. The crude product is chromatographed on silica gel (20 g). The column is packed and eluted with chloroform/4.1M ammonia in methanol (4/1). An initial fraction of 12 ml is collected, followed by 2 ml fractions. Based on their TLC homogeneity, fractions 14–22 are combined can concentrated to give the title compound, NMR (CDCl$_3$; TMS) 7.50–7.30, 6.36, 4.00–3.80, 3.76–3.61, 3.60–3.5, 3.20–2.90 and 2.85–2.40δ; CMR (CDCl$_3$; TMS) 157.8, 156.8, 155.5, 134.9, 132.6, 128.3, 128.2, 127.2, 100.1, 96.6, 70.0, 67.0, 64.7, 60.7, 53.3, 53.1, 45.2, 44.1 and 29.5δ; MS (m/z) calc'd for $C_{27}H_{39}N_7O_4$, $M^+$=525.3063, found=525.3047, other ions 510, 494, 464, 450, 395, 304, 278, 264 and 201.

EXAMPLE 47

4,4'-(7-Methyl-6-phenyl-7H-pyrrolo[2,3-d]pyrimidine-2,4-diyl)bis-1-piperazineacetic acid diethyl ester (VII)

A mixture of 7-methyl-6-phenyl-2,4-di-1-piperazinyl-7H-pyrrolo[2,3-d]pyrimidine (VII, EXAMPLE 44, 300 mg) in THF (30 ml) is treated with N,N-diisopropylethylamine (0.29 ml) followed by ethyl bromoacetate (0.28 g) and the reaction mixture is stirred at 20°–25° for 66 hr. The reaction mixture is concentrated under reduced pressure and the residue is partitioned between chloroform and saturated sodium bicarbonate. The organic layer is separated washed with saline, dried over anhydrous sodium sulfate, and concentrated under reduced pressure. The crude product is chromatographed on silica gel (180 g). The column is packed and eluted with chloroform/4.0M ammonia in methanol (98/2). An initial fraction of 150 ml is collected, followed by 6 ml fractions. Based on their TLC homogeneity, fractions 12–27 are combined and concentrated to give the title compound, IR (liquid) 2934, 2845, 1748, 1582, 1474, 1509, 1484, 1441, 1400, 1380, 1371, 1344, 1331, 1309, 1279, 1255, 1245, 1227, 1204, 1186, 1159, 1033, 1007 and 751 cm$^{-1}$; NMR (CDCl$_3$, TMS) 7.5–7.3, 6.35, 4.3–4.15, 4.05–3.8, 3.66, 3.26 and 1.4–1.2δ; MS (m/z) calc'd for $C_{29}H_{39}N_7O_4$, $M^+$=549.3063, found=549.3073, other ions 534, 476, 462, 407, 304, 292, 278, 264, 262, 238, 201, and 187.

EXAMPLE 48

4,4'-(7-Methyl-6-phenyl-7H-pyrrolo[2,3-d]pyrimidine-2,4-diyl)bis-1-piperazineacetic acid, dipotassium salt (VII)

A mixture of 4,4'-(7-methyl-6-phenyl-7H-pyrrolo[2,3-d] pyrimidine-2,4-diyl)bis-1-piperazine acetic acid diethyl ester (VII, EXAMPLE 47, 49 mg) in methanol (3 ml) and water (10 ml) is treated with potassium hydroxide (1M, 0.18 ml) mixture and the reaction mixture is stirred at 20°–25° for 66 hr and concentrated under reduced pressure. The resulting residue is redissolved in water (25 ml) and then placed on the lyophilizer for 18 hr. The solid is then dried in a vacuum oven (5 hours, 0.01 mm, 4°) to give the title compound, mp 218°–220°; IR (mineral oil) 3390, 3049, 2953, 2923, 2867, 2855, 1628, 1582, 1561, 1508, 1484, 1457, 1445, 1401, 1377, 1316, 1309, 1284, 1267, 1251, 1208, 1006, 982, 749 and 699 cm$^{-1}$; NMR (DMSO-d$_6$, TMS) 7.57, 7.45, 7.37, 6.61, 3.7, 3.61, 2.98 and 2.50δ; MS (m/z) calc'd for $C_{25}H_{32}N_7O_4$ (acid) $(M+H)^+$=494.25 16, found=494.2537, other ions 478, 464, 448, 436, 393, 379, 335, 319, 292, 278, 264 and 222.

EXAMPLE 49

5,7-Dimethyl-6-phenyl-2,4-di-1-pyrrolidinyl-7H-pyrrolo[2,3-d]pyrimidine (VII)

A mixture of 4-methylamino-2,6-di-1-pyrrolidinopyrimidine (V, EXAMPLE 3, 500 mg) in acetonitrile (20 ml) is treated with N,N-diisopropylethylamine (0.45 ml) followed by 2-bromopropiophenone (0.31 ml), the reaction mixture is stirred at reflux for 26 hr and concentrated reduced pressure, and the resulting residue is partitioned between chloroform and saturated sodium bicarbonate. The organic layer is separated, washed with saline, dried over anhydrous sodium sulfate, and concentrated under reduced pressure. The crude product is chromatographed on silica gel (180 g). The column is packed and eluted with methylene chloride/acetone (98/2). An initial fraction of 400 ml is collected, followed by 6 ml fractions. Based on their TLC homogeneity, fractions 16–65 are combined and concentrated to give a solid which is recrystallized from absolute ethanol. The solid is isolated and dried (18 hours, 0.15 mm) to give the title compound, mp 139°–140°; NMR (CDCl$_3$, TMS) 7.46–7.32, 3.75, 3.62, 3.48, 2.25 and 1.96–1.91δ; MS (m/z) calc'd for $C_{22}H_{27}N_5M^+$=361.2266, found=361.2263, other ions 333, 318, 306, 292, 264, 180 and 145.

EXAMPLE 50

6-(4-Methoxyphenyl)-7-methyl-2,4-di-1-pyrrolidinyl-7H-pyrrolo[2,3-d]pyrimidine (VII)

Following the general procedure of EXAMPLE 49 and making non-critical variations but starting with 2-bromo-4'-methoxyacetophenone (VI), mp 247°–248°; NMR (CDCl$_3$, TMS) 7.37, 6.95, 6.34, 3.85–3.64 and 1.98–1.92δ; MS (m/z) calc'd for $C_{22}H_{27}N_5O$ $M^+$= 377.2215, found=377.2222, other ions at m/z 349, 322, 279, 237, 188 and 167.

EXAMPLE 51

6-(4-Methoxyphenyl)-7-methyl-2,4-di-1-pyrrolidinyl-7H-pyrrolo[2,3-d]pyrimidine methanesulfonate (VII-salt)

Following the general procedure of EXAMPLE 36 and making non-critical variations but starting with 6-(4-methoxyphenyl)-7-methyl-2,4-di-1-pyrrolidinyl-7H-pyrrolo[2, 3d]pyrimidine (VII, EXAMPLE 50, 3 g), methanesulfonic acid (765 mg), mp 195°–196°; IR (mineral oil) 2956, 2923, 2870, 2855, 1630, 1613, 1591, 1577, 1559, 1536, 1500, 1480, 1463, 1459, 1445, 1378, 1357, 1338, 1305, 1246, 1209, 1195, 1171, 1046 and 1041 cm$^{-1}$.

EXAMPLE 52

6,7-Dimethyl-2,4-di-1-pyrrolidinyl-7H-pyrrolo[2,3-d]pyrimidine (VII)

Following the general procedure of EXAMPLE 49 and making non-critical variations but starting with bromoacetone (VI), the title compound is obtained, mp 195°–197°; NMR (CDCl$_3$, TMS) 6.07, 3.74, 3.61–3.55, 2.28, and 1.98–1.90δ; MS (m/z) calc'd for $C_{16}H_{23}N_5$ $(M)^+$=285.1953, found=285.1952, other ions 257, 243, 229, 216, 188, 159, 142, 121, 107 and 43.

EXAMPLE 53

6,7-Dimethyl-2,4-di-1-pyrrolidinyl-7H-pyrrolo[2,3-d]pyrimidine methanesulfonate salt (VII-salt)

A stirred suspension of 6,7-dimethyl-2,4-di-1-pyrrolidinyl-7H-pyrrolo[2,3-d]pyrimidine (VII, EXAMPLE 52, 500 mg) in 2-propanol/water (95/5, 60 ml) is treated with a mixture of methanesulfonic acid (169 mg) in 4 ml of the same solvent mixture. The reaction mixture is stirred until it became completely homogeneous (30 min) and then concentrated under reduced pressure. The residue is triturated with ethyl acetate/hexane (1/1, 50 ml), filtered and dried (18 hours, 0.02 mm, 25°) to give the title compound, mp 181°–183°.

EXAMPLE 54

4(7-Methyl-2,4-di-1-pyrrolidinyl-7H-pyrrolo[2,3-d]pyrimidin-6-yl)phenol (VII)

A mixture of 6-(4-methoxyphenyl)-7-methyl-2,4-di-1-pyrrolidinyl-7H-pyrrolo[2,3-d]pyrimidine (VII, EXAMPLE 50, 200 mg) in hydrobromic acid (48%, 20 ml) is refluxed for 30 min. The reaction mixture is concentrated under reduced pressure. The resulting reside due partitioned between chloroform and saturated sodium bicarbonate. The organic layer is separated, washed with saline, dried over anhydrous sodium sulfate, concentrated and recrystallized from chloroform/hexane to give the title compound, mp 268°–270°; IR (mineral oil) 3119, 3035, 2955, 2926, 2869, 2855, 2805, 2659, 1611, 1565, 1527, 1502, 1468, 1454, 1406, 1377, 1355, 1318, 1265, 1257, 1241, 1227, 1171, 838 and 772 cm$^{-1}$; NMR (DMSO-$d_6$, TMS) 7.34, 6.83, 6.36, 3.75–3.45 and 2.00–1.80δ; MS (m/z) calc'd for $C_{21}H_{25}N_5O_2$ M$^+$=363.2059, found=363.2053, other ions at m/z 355, 321, 308, 292, 280, 265, 238, 223, 181, 160 and 146.

EXAMPLE 55

4-(7-Methyl-2,4-di-1-pyrrolidinyl-7H-pyrrolo[2,3-d]pyrimidin-6-yl)phenol, hydrobromide salt (VII-salt)

A mixture of 6-(4-methoxyphenyl)-7-methyl-2,4-di-1-pyrrolinyl-7H-pyrrolo[2,3d]pyrimidine (VII, ee 54, 5 g) in concentrated hydrobromic acid (48%, 85 ml) is heated at reflux under nitrogen for 45 min. The reaction mixture is then cooled to 20°–25° and diluted with 35 ml of water. The resulting solid product is isolated by filtration, washed with cold water (3× 25 ml), and dried (16 hours, 0.02 mm, 40°), to give the title compound, mp 298°–300° (decomp). Recrystallization from 95% ethanol (40–50 ml per g), NMR (DMSO-$d_6$, TMS) 9.77, 7.37, 6.89, 6.67, 3.70, 3.8–3.45, 2.1–1.9δ.

EXAMPLE 56

7-Methyl-6-(4-fluorophenyl)-2,4-di-1-pyrrolidinyl-7H-pyrrolo[2,3-d]pyrimidine (VII)

Following the general procedure of EXAMPLE 40 and making non-critical variations but starting with 4-methylamino-2,6-di-1-pyrrolidinopyrimidine (V, EXAMPLE 3, 1.44 g) and 2-bromo-4'-fluoroacetophenone (VI, 1.27 g), the title compound is obtained, mp 194.5°–196°; NMR (CDCl$_3$, TMS) 7.4, 7.10, 6.38, 3.79, 3.64, 3.60, 1.95δ; IR (mineral oil) 1575, 1563, 1521, 1496, 1483, 1397, 1359, 1346, 1319, 1307, 1219, 1155, 845, 837, 776 cm$^{-1}$; MS (m/z) calc'd for $C_{21}H_{24}FN_5$ M$^+$=365, found=365.

EXAMPLE 57

7-Methyl-6-(4-fluorophenyl)-2,4-di-1-pyrrolidinyl-7H-pyrrolo[2,3-d]pyrimidine monomethanesulfonate (VII-salt)

Following the general procedure of EXAMPLE 36 and making non-critical variations but starting with 7-methyl-6-(4-fluorophenyl)-2,4-di-1-pyrrolidinyl-7H-pyrrolo[2,3-d]pyrimidine (VII, EXAMPLE 56, 1.657 g), the title compound is obtained, mp 200°–202°; NMR (CDCl$_3$, TMS) 7.4, 7.14, 6.41, 3.85, 2.80, 2.05δ; IR (mineral oil) 1626, 1599, 1574, 1541, 1500, 1444, 1390, 1356, 1332, 1314, 1235, 1225, 1174, 1040, 845, 827, 767, 760, 739 cm$^{-1}$; MS (m/z) calc'd for $C_{21}H_{24}FN_5$ (M)$^+$ free base=365.2016, found=365.2034.

EXAMPLE 58

(3,5-Di-t-butyl-4-hydroxyphenyl)ethanone (VI)

A mixture of 2,6-di-t-butylphenol (1 g) in trifluoroacetic anhydride (5 ml) is carefully treated with 0.28 ml of glacial acetic acid and the reaction mixture is stirred at 20°–25° for 1 hr. The reaction mixture is diluted with chloroform and is separated, washed with saline, dried over anhydrous sodium sulfate, and concentrated under reduced pressure. The crude product (1.39 g) is chromatographed on 180 g of silica gel. The column is packed and eluted with chloroform/acetone (99/1). An initial fraction of 200 ml is collected, followed by 7 ml fractions. Based on their TLC homogeniety, fractions 20–55 are combined and concentrated. Recrystallized from hexane gives the tire compound, mp 148°–150°; IR (mineral oil) 3581, 3007, 2956, 2925, 2871, 2856, 1663, 1596, 1581, 1465, 1463, 1442, 1423, 1370, 1364, 1356, 1320, 1305, 1274, 1239, 1232, 1138, 1124, 1108 an 886 cm$^{-1}$; NMR (CDCl$_3$, TMS) 7.84, 5.73, 2.56, and 1.47δ; CMR (CDCl$_3$, TMS) 197.6, 158, 4, 135.8, 129.1, 126.1, 34.4, 30.2 and 26.3δ; MS (m/z) M$^+$ (found)=248; other ions at m/z 233, 217, 205, 189, 178, 115, 57 and 43.

EXAMPLE 59

2-Bromo-1-(3,5-di-t-butyl-4-hydroxyphenyl)ethanone (VI)

A mixture of (3,5-Di-t-butyl-4-hydroxyphenyl)ethanone (EXAMPLE 58, 800 mg) in ether (15 ml) and chloroform (10 ml) is cooled to 0° and then treated in a dropwise manner with a mixture containing 0. 17 ml of bromine dissolved in 5 ml of chloroform. The reaction mixture is allowed to warm to 20°–25° and stirred for 1 hr. Standard work-up gives the crude product (1.21 g) which is chromatographed on 180 g of silica gel. The column is packed and eluted with chloroform. An initial fraction of 200 ml is collected, followed by 7 ml fractions. Based on their TLC homogeneity, fractions 36–65 are combined and concentrated. Recrystallization from hexane gives the title compound, mp 105°–106°; IR (mineral oil) 3590, 2955, 2925, 2871, 2856, 1685, 1594, 1581, 1466, 1459, 1451, 1438, 1426, 1366, 1328, 1302, 1282, 1242, 1194, 1153, 1139, 1121, 860 and 615 cm$^{-1}$; NMR (CDCl$_3$; TMS) 7.88, 5.85, 4.40 and 1.47δ; CMR (CDCl$_3$; TMS) 190.6, 159.0, 135.9, 126.8, 125.6, 34.2, 30.6 and 29.9δ; MS (m/z) M$^+$ found=327, other ions at m/z 326, 311,233, 219, 203, 189, 175, 115, 101, 87, 57 and 40.

EXAMPLE 60

2,6-Bis(1,1-dimethylethyl)-4-(7-methyl-2,4-di-1-pyrrolidinyl-7H-pyrrolo[2,3-d]pyrimidin-6-yl)phenol (VII)

Following the general procedure of EXAMPLE 40 and making non-critical variations but starting with 4-methylamino-2,6-di-1-pyrrolidino-pyrimidine (V, EXAMPLE 3, 378 mg) and 2-bromo-1-(3,5-di-t-butyl-4-hydroxyphenyl)ethanone (VI, EXAMPLE 59, 500 mg), the title compound is obtained, mp 222°–224°; IR (mineral oil) 3635, 3620, 2957, 2925, 2870, 2857, 1577, 1563, 1532, 1516, 1488, 1450, 1398, 1375, 1366, 1358, 1347, 1336, 1233, 1221, 766 and 629 cm$^{-1}$; NMR (CDCl$_3$, TMS) 7.26, 6.32, 5.24, 3/85–3.55, 2.05–1.90 and 1.47δ; CMR (CDCl$^3$, TMS) 157.7, 155.2, 152.9, 135.7, 124.3, 99.4, 96.1, 47.2, 46.4, 34.2, 30.1, 29.5, 25.5 and 25.2δ; MS (m/z) calc'd for $C_{29}H_{41}N_5O$ M$^+$=475.3311, found=475.3317, other ions at m/z 460, 447, 433, 418, 404, 388, 377, 237, 216, 194 and 181.

EXAMPLE 61

2,6-Bis(1,1-dimethylethyl)-4-(7-methyl-2,4-di-1-pyrrolidinyl-7H-pyrrolo[2,3-d]pyrimidin-6-yl)-phenol monomethanesulfonate (VII-salt)

Following the general procedure of EXAMPLE 36 and making non-critical variations but starting with 2,6-bis(1,1-dimethylethyl)-4-(7-methyl-2,4-di-1-pyrrolidinyl-7H-pyrrolo[pyrimidin-6-yl)-phenol (VII, EXAMPLE 60), the title compound is obtained, NMR (CDCl$_3$, TMS) 7.16, 6.36, 5.4, 3.90, 3.9–3.75, 2.83, 2.2–2.0, 1.47δ; MS (m/z) calc'd for $C_{29}H_{41}N_5O$ (M)$^+$=475.3311, found=475.3325; IR (mineral oil) 3246, 1627, 1601, 1541, 1434, 1355, 1313, 1231, 1222, 1203, 1175, 1049, 1043 cm$^{-1}$.

EXAMPLE 62

2,6-Diisopropylphenyl acetate

A suspension of 2,6-diisopropylphenol (5.32 g) in 35 ml of trifluoroacetic anhydride is treated with 1.75 ml of glacial acetic acid under a nitrogen atmosphere. Upon completion of the addition of acetic acid, the solids are in mixture. Solvent evaporation gives an oil which is taken up in 150 ml of ethyl acetate and washed twice with saturated aqueous sodium bicarbonate and once with saline. Drying of the organic layer with sodium sulfate followed by filtration and solvent evaporation gives 6.55 g of an oil which is chromatographed on 330 g of silica gel eluting with chloroform/hexane (9/1). The appropriate fractions are pooled and concentrated to give the title compound, NMR (CDCl$_3$, TMS) 7.2, 2.91, 2.36, 1.20.

EXAMPLE 63

3,5-Diisopropyl-4-hydroxyacetophenone 2,6-Diisopropylphenyl acetate (6.16 g, EXAMPLE 62) and aluminum chloride (4.0 g) are mixed with cooling in an ice bath. The suspension is warmed to 20°–25° and gradually heated in an oil bath at 120°. After 5 hours the reaction is cooled to 20°–25° and treated with 1M aqueous hydrochloric acid, followed by extraction of the aqueous layer with three portions of ether. The combined organic layers are washed with water until the aqueous layer is no longer acidic. A final washing of the organic layer with saline, followed by drying (sodium sulfate), filtration, and solvent evaporation gives 21.8 g of an oil which is chromatographed on 500 g of silica gel eluting with chloroform/hexane (9/1) initially and gradually changing to chloroform. The appropriate fractions are pooled and concentrated to give the title compound, NMR (CDCl$_3$, TMS) 7.72, 5.35, 3.17, 2.57, 1.30δ.

EXAMPLE 64

4-Bromoacetyl-2,6-bis(1-methylethyl)phenol (VI)

A mixture of 3,5-diisopropyl-4-hydroxyacetophenone (EXAMPLE 63, 0.52 g) in 10 ml of ether and 5 ml of chloroform is cooled in an ice bath. To this mixture is added 0.13 ml of bromine in 7 ml of chloroform over a period of 1 hr. The reaction is warmed to 20°–25° and diluted with additional chloroform. The mixture is transferred to a separatory funnel and washed with water and saline. Drying of the organic layer with sodium sulfate followed by filtration and solvent evaporation gives 0.877 g of a semi-solid which is chromatographed on 120 g of silica gel eluting with chloroform/hexane (8/2). An initial fraction of 200 ml is collected followed by 10 ml fractions. Fractions 34–59 containing the desired product are pooled and concentrated to give the title compound, NMR (CDCl$_3$, TMS) 7.75, 5.41, 4.42, 3.17, 1.30δ; MS (m/z) calc'd for C$_{14}$H$_{19}$BrO$_2$ M$^+$=298 and 300, found=298 and 300.

EXAMPLE 65

2,6-Bis(1-methylethyl)-4-(7-methyl-2,4-di-1-pyrrolidinyl-7H-pyrrolo[2,3-d]pyrinidin-6-yl)phenol (VII)

Following the general procedure of EXAMPLE 6 and making non-critical variations but starting with 4-methylamino-2,6-di-1-pyrrolidino-pyrimidine (V, EXAMPLE 3, 0.874 g) and 4-bromoacetyl-2,6-bis(1-methylethyl)phenol (VI, EXAMPLE 64), the title compound is obtained, NMR (CDCl$_3$, TMS) 7.14, 6.33, 4.85, 3.8, 3.64, 3.19, 1.95, 1.30δ; MS (m/z) calc'd for C$_{27}$H$_{37}$N$_5$O M$^+$=447, found=447.

EXAMPLE 66

2,6-Bis(1-methylethyl)-4-(7-methyl-2,4-di-1-pyrrolidinyl-7H-pyrrolo[2,3-d]pyrimidin-6-yl)-phenol monomethanesulfonate (VII-salt)

Following the general procedure of EXAMPLE 36 and making non-critical variations but starting with 2,6-bis(1-methylethyl)-4-(7-methyl-2,4-di-1-pyrrolidinyl-7H-pyrrolo[2,3d]pyrinidin-6-yl)-phenol (VII, EXAMPLE 65, 0.603 g), the title compound is obtained, mp 221°–231°; NMR (CDCl$_3$, TMS) 7.04, 6.36, 3.88, 3.8, 3.2, 2.81, 2.1, 1.29δ; MS (m/z) calc'd for C$_{27}$H$_{37}$N$_5$O (free base) (M)$^+$=447.2998, found=447.2984; IR (mineral oil) 3253, 3200, 1632, 1592, 1539, 1443, 1426, 1354, 1339, 1230, 1204, 1171, 1147, 1046, 1042, 770, 754 cm$^{-1}$.

EXAMPLE 67

2,6-Dimethylphenyl acetate

Following the general procedure of EXAMPLE 62 and making non-critical variations but starting with 2,6-dimethylphenol, the title compound is obtained, NMR (CDCl$_3$) 7.05, 2.34, 21.6δ.

EXAMPLE 68

3,5-Dimethyl-4-hydroxyacetophenone

Following the general procedure of EXAMPLE 63 and making non-critical variations but starting with 2,6-dimthylphenyl acetate (EXAMPLE 67) the title compound is obtained, mp 152°–153°; NMR (CDCl$_3$) 7.64, 5.33, 2.55, 2.30δ.

EXAMPLE 69

2-Bromo-1-(4-hydroxy-3,5-dimethylphenyl)ethanone (VI)

Following the general procedure of EXAMPLE 64 and making non-critical variations but starting with 3,5-dimethyl-4-hydroxyacetophenone (EXAMPLE 68), the title compound is obtained, mp 128.5°–131°; NMR (CDCl$_3$, TMS) 7.67, 5.25, 4.40, 2.30δ; MS (m/z) calc'd for 242 and 244, found=242 and 244.

EXAMPLE 70

2,6-Dimethyl-4-(7-methyl-2,4-di-1-pyrolidinyl-7H-pyrrolo[2,3-d]pyrimidin-6-yl)phenol (VII)

Following the general procedure of EXAMPLE 6 and making non-critical variations but starting with 4-methylamino-2,6-di-1-pyrrolidino-pyrimidine (VII, EXAMPLE 3, 2.24 g,) and 2-bromo-1-(4-hydroxy-3,5-dimethylphenyl)ethanone (VI, EXAMPLE 69) the title compound is obtained, mp 184°–187°; NMR (CDCl$_3$, TMS) 7.08, 6.3, 4.7, 3.79, 3.6, 2.29 and 1.9δ; MS (m/z) 391, found 391; IR (mineral oil) 3134, 3032, 1572, 1563, 1526, 1483, 1399, 1359, 1347, 1321, 1311, 1297, 1286, 1221, 1168, 876, 760, 652 cm$^{-1}$.

EXAMPLE 71

2,6-Dimethyl-4-(7-methyl-2,4-di-1-pyrrolidinyl-7H-pyrrolo[2,3-d]pyrimidin-6-yl)phenol monomethansulfonate (VII-salt)

Following the general procedure of EXAMPLE 36 and making non-critical variations but starting with 2,6-dimethyl-4-(7-methyl-2,4-di-1-pyrolidinyl-7H-pyrrole[2,3-α]pyrimidin-6-yl)phenol (VII, EXAMPLE 70, 1.629 g), the title compound is obtained, mp 259°–264°; NMR (CDCl$_3$, TMS) 6.99, 6.33, 3.85, 2.81, 2.28 and 2.1δ; MS (m/z) calc'd=391.2372, found=391.2367; IR (mineral oil) 3251,

EXAMPLE 72

2-Bromo-1-(3,4,5-trimethoxyphenyl)ethanone (VI)

A mixture of 3.0 g of 3,4,5-trimethoxyacetophenone in 70 ml of dimethyl ether and 30 ml of chloroform is cooled to 0° and then treated with a mixture containing 0.73 ml of bromine in 15 ml of chloroform in a dropwise manner. The reaction mixture is allowed to warm to 20°–25° and stirred for 1 hr. The reaction mixture is partitioned between chloroform and water. The organic layer is separated, washed with dilute sodium bicarbonate, washed with saline, dried over anhydrous sodium sulfate, and concentrated under reduced pressure. The crude product (4.31 g) is recrystallized from ethanol/water. The solid is isolated and dried (18 hours, 0.01 mm, 40°) to give the title compound, mp 61°–62°; IR (mineral oil) 3010, 2995, 2952, 2926, 2868, 2855, 1695, 1687, 1586, 1505, 1466, 1455, 1428, 1417, 1389, 1335, 1255, 1229, 1190, 1151, 1128, 1004, 820, 636, and 602 cm$^{-1}$; NMR (CDCl$_3$, TMS) 7.24, 4.43 and 3.93δ; CMR (CDCl$_3$) 190.2, 153.1, 149.9, 143.3, 128.9, 106.5, 60.9, 56.3 and 30.4δ; MS (m/z) M$^+$=288, other ions at m/z 259, 228, 195, 181, 167, 152, 137, 122, 109, 77, 66 and 53.

EXAMPLE 73

5-(7-Methyl-2,4-di-1-pyrrolidinyl-7H-pyrrolo[2,3-d]pyrimidin-6-yl)-1,2,3-trimethoxybenzene (VII)

Following the general procedure of EXAMPLE 40 and making non-critical variations but starting with 4-methylamino-2,6-di-1-pyrrolidinopyrimidine (V, EXAMPLE 3) and 2-bromo-1-(3,4,5-trimethoxyphenyl)ethanone (VI, EXAMPLE 72), the title compound is obtained, mp 204°–206°; IR (mineral oil) 2954, 2925, 2869, 2855, 1581, 1573, 1540, 1514, 1499, 1473, 1457, 1411, 1396, 1377, 1359, 1346, 1335, 1302, 1243, 1189, 1125, 1017, 841,761 and 602 cm$^{-1}$; NMR (CDCl$_3$, TMS) 6.66, 6.39, 3.90, 3.85–3.60 and 2.05–1.90δ; CMR 158.0, 155.5, 153.2, 137.3, 133.2, 128.9, 105.7, 100.7, 96.3, 60.9, 56.2, 47.5, 46.6, 29.9, 25.7 and 25.3δ; MS (m/z) M$^+$ (found)=437, other ions at m/z 422, 409, 394, 382, 366, 351,308, 218, 197, 182, 168 and 153.

EXAMPLE 74

5-(7-Methyl-2,4-di-1-pyrrolidinyl-7H-pyrrolo[2,3-d]pyrimidin-6-yl)-1,2,3-benzenetriol monohydrobromide (VII)

Following the general procedure of EXAMPLE 55 and making non-critical variations but starting with 5-(7-methyl-2,4-di-1-pyrrolidinyl-7H-pyrrolo[2,3-d]pyrimidin-6-yl)-1,2, 3-trimethoxybenzene (VII, EXAMPLE 73) and hydrobromic acid (48%, 40 ml), the title compound is obtained, mp 270°–272°; IR (mineral oil) 3457, 3359, 3222, 3150, 2954, 2925, 2870, 2855, 1630, 1559, 1521, 1462, 1406, 1400, 1377, 1358, 1343, 1328, 1234, 1205, 1192, 1037, 1023, 747 and 653 cm$^{-1}$; NMR (DMSO-d$_6$) 6.57, 6.46, 4.00–3.60 and 2.15–1.80δ; CMR (DMSO-d$_6$, TMS) 154.2, 148.8, 146.4, 140.5, 135.7, 133.8, 120.9, 108.1, 101.3, 96.3, 48.7, 47.8, 32.8 and 25.0δ; MS (m/z) calc'd=395.1957, found= 395.1952, other ions at m/z 367, 353, 340, 326, 312, 297, 270, 255, 197, 176, 82 and 70.

EXAMPLE 75

1-Bromo-4-(4-methoxyphenyl)butan-2-one (VI)

Dry tetrahydrofuran (45 ml) is cooled in a dry ice-acetone bath under a nitrogen atmosphere and treated with 16.5 ml of 2.0M lithium diisopropylamide in heptanes/tetrahydrofuran/ethyl benzene (Aldrich Chemical Co.). To this cold mixture is added 5 g (0.028 mol) of 4-(4-methoxyphenyl)-2-butanone dissolved in 10 ml of dry tetrahydrofuran. The addition is carried out over 5 minutes. The reaction is stirred with cooling in the dry ice-acetone bath for 45 minutes. In a separate flask triethylamine (2.35 ml) in 30 ml of dry tetrahydrofuran is treated with 13.2 ml (0.104 mol) of trimethylsilyl chloride. A suspension formed which is filtered using a plug of glass wool. The remaining mixture is added to the above prepared lithio salt. The entire reaction mixture is stirred with cooling in a dry ice-acetone bath for 2 hours.

The above reaction is treated with 1.8 g of solid sodium bicarbonate and 70 ml of saturated aqueous sodium bicarbonate. The mixture is warmed to 0° and diluted with ether. The reaction contents are poured into a separatory funnel and the layers are separated. The aqueous layer is extracted with additional portions of ether (2×). The combined organic layers are washed with saline followed by drying (sodium sulfate), filtration, and solvent evaporation, which gives 7.21 g of an intermediate trimethylsilyl enol ether.

The silyl enol ether is dissolved in 175 ml of dry tetrahydrofuran and treated with 2.84 g of solid vacuum dried, sodium bicarbonate. The suspension is cooled in a dry ice-acetone bath and treated with solid N-bromosuccinimide (5.05 g). The suspension is stirred with cooling in the dry ice-acetone bath for 2 hours. The reaction is warmed slowly to 0° and poured into a separatory funnel containing saturated sodium bicarbonate, saline, and ether. The layers are separated. The aqueous layer is extracted an additional time with ether. The combined organic layers are washed with saline, followed by drying sodium salt, filtration, and solvent evaporation. Drying gives the title compound, NMR (CDCl$_3$, TMS) 7.10, 6.82, 3.84, 3.79 and 2.91δ.

EXAMPLE 76

6-[2-(4-Methoxyphenyl)ethyl]-7-methyl-2,4-di-1-pyrrolidinyl-7H-pyrrolo[2,3-d]pyrimidine (VII)

Following the general procedure of EXAMPLE 40 and making non-critical variations but starting with 4-methylamino-2,6-di-1-pyrrolidinopyrimidine (V, EXAMPLE 3, 5 g) and 1-bromo-4-(4-methoxyphenyl)butan-2-one (VI, EXAMPLE 75, 5.36 g), the title compound is obtained, NMR (CDCl$_3$, TMS) 7.11, 6.83, 6.08, 3.79, 3.75, 3.60, 3.54, 2.89 and 1.93δ; IR (mineral oil) 1611, 1578, 1563, 1547, 1524, 1513, 1485, 1437, 1400, 1355, 1346, 1314, 1302, 1251, 1238, 827, 808, 786 cm$^{-1}$; MS (m/z) found=405.

EXAMPLE 77

6-[2-(4-Methoxyphenyl)ethyl]-7-methyl-2,4-di-1-pyrrolidinyl-7H-pyrrolo[2,3-d]pyrimidine monomethanesulfonate (VII-salt)

Following the general procedure of EXAMPLE 36 and making non-critical variations but starting with 6-[2-(4-methoxyphenyl)ethyl]-7-methyl-2,4-di-1-pyrrolidinyl-7H-pyrrolo[2,3]pyrimidine (VII, EXAMPLE 76, 2.469 g), the title compound is obtained, mp 178.5°–181°; NMR (CDCl$_3$, TMS) 7.09, 6.84, 6.13, 3.87, 3.80, 3.75, 2.86 and 2.05δ; MS (m/z) calc'd =405.2528, found=405.2527; IR (mineral oil) 1626, 1597, 1565, 1543, 1515, 1446, 1359, 1336, 1306, 1259, 1244, 1232, 1220, 1177, 1166, 1040, 825, 772, 742 cm$^{-1}$.

EXAMPLE 78

5,6-Bis(4-chlorophenyl)-7-methyl-2,4-di-1-pyrrolidinyl-7H-pyrrolo[2,3-d]pyrimindine (VII)

A stirred mixture of 4-methylamino-2,6-di-1-pyrrolidinopyrimidine (V, EXAMPLE 3, 718 mg) and 0.65 ml diisopropylethylamine in 15 ml of acetonitrile is treated with 2-bromo-1,2-bis(4-chlorophenyl)ethanone (VI, Chem. Pharm. Bull, 39, 651 (1991), 1.0 g) and the resulting mixture is stirred at 25° for 18 hours under a nitrogen atmosphere in a foil-wrapped flask. After 18 hr, the resulting solid is filtered, washed with acetonitrile and dried (18 hours, 0.05 mm, 25°). This material (1.53 g) is dissolved in 100 ml of toluene and heated at reflux for 4 hours. The mixture is cooled to 20°–25° and the toluene is removed in the rotary evaporator. The resulting crude solid product is recrystallized from 100 ml of ethyl acetate. The solids are isolated by filtration, washed with 3×10 ml of −20° ethyl acetate, and dried (16 hours, 40°, 0.05 mm), m give the title compound, mp 231°–232°; IR (CDCl$_3$, TMS) 72.9–7.00, 3.66–3.61, 3.52, 3.15–3.11, 1.98–1.94 and 1.64–1.59δ; HRMS (m/z) M$^+$ observed at 491.1647, calc'd=491.1643, other ions observed at m/z 463, 436, 421, 393, 246, 228, 214.

EXAMPLE 79

5,6-Bis(4-methoxyphenyl)-7-methyl-2,4-di-1-pyrrolidinyl-7H-pyrrolo[2,3-d]pyrimidine (VII)

Following the general procedure of EXAMPLE 78 and making non-critical variations but starting with 2-bromo-1,2-bis(4-methoxyphenyl)ethanone (VI, Chem. Pharm. Bull, 39, 651 (1991)), the title compound is obtained, mp 190°–192° and 229°–231°; NMR (CDCl$_3$, TMS) 7.1–7.0, 6.83–6.70, 3.78, 3.77, 3.63, 3.52, 3.14, 2.0–1.93 and 1.65–1.55δ; HRMS (m/z) M$^+$ observed at 483.2638, other ions observed at (m/z) 455, 427, 413, 241.5.

EXAMPLE 80

4,4'-(7-Methyl-2,4-di-1-pyrrolidinyl-7H-pyrrolo[2,3-d]pyrimidine-5,6-diyl)bis-phenol, monohydrobromide (VII)

Following the general procedure of EXAMPLE 55 and making non-critical variations but starting with 5,6-bis(4-methoxyphenyl)-7-methyl-2,4-di-1-pyrrolidinyl-7H-pyrrolo[2,3-d]-pyrimidine (VII, EXAMPLE 79, 0.504 g), the title compound is obtained, mp 245° (decomp.); NMR (methanol-d$_6$, TMS) 6.94, 6.73, 6.67, 3.72, 3.57, 2.10 and 1.7δ; MS (m/z) calc'd=455.2321, found=455.2329; IR (mineral oil) 3201, 3025, 1625, 1571, 1521, 1495, 1345, 1338, 1268, 1218, 1170 cm$^{-1}$.

EXAMPLE 81

N-(4'-Methoxyphenyl)-2,6-di-1-pyrrolidinyl-4-pyrimidinamine (V)

A mixture of 2.44 g of p-anisidine is heated to 135° (oil bath). The molten mixture is treated with 4-chloro-2,6-di-1-pyrrolidinylpyrimidine [V, J. Med. Chem., 33,1145 (1990), 500 mg] and the reaction is stirred at 135° for 18 hr. The reaction mixture is allowed to cool and is then partitioned between chloroform and water. The organic layer is separated, washed with saline, dried over anhydrous sodium sulfate, and concentrated under reduced pressure. The crude product (1.93 g) is chromatographed on 180 g of mesh silica gel. The column is packed and eluted with dichloromethane/ethyl acetate (9/1). An initial fraction of 2000 ml is collected. The solvent system is then changed to ethyl acetate/dichloromethane (9/1) and 10 ml fractions are then collected. Based on their TLC homogeneity, fractions 5–25 are combined to give the title compound, which is recrystallized from ethanol/water and dried (18 hours, 0.01 mm, 40°), mp 162°–163°; IR (mineral oil) 3273, 2953, 2925, 2865, 2854, 1609, 1586, 1571, 1549, 1505, 1478, 1453, 1427, 1409, 1377, 1343, 1313, 1303, 1294, 1236, 1219, 1171, 1043, 821 and 788 cm$^{-1}$; NMR (CDCl$_3$, TMS) 7.30–7.20, 6.90–6.80, 6.19, 4.99, 4.03, 3.60–3.30 and 2.00–1.80δ; CMR (CDCl$_3$, TMS) 161.9, 160.3, 155.6, 133.1, 123.9, 114.1, 72.6, 55.3, 46.1, 45.8, 25.4 and 25.1δ; MS M$^+$ found=339, other ions 324, 311, 297, 283, 270, 242, 169, 148, 121, 70 and 55.

EXAMPLE 82

6,7-Bis(4-methoxyphenyl)-2,4-di-1-pyrrolidinyl-7H-pyrrolo[2,3-d]pyrimidine (VII)

Following the general procedure of EXAMPLE 40 and making non-critical variations but starting with N-(4'-methoxyphenyl)-2,6-di-1-pyrrolidinyl-4-pyrimidinamine (V, EXAMPLE 81), the product is obtained, recrystallized from chloroform/hexane, and dried (20 hours, 0.03 mm, 40°) to give the title compound, mp 203°–205°; IR (mineral oil) 2954, 2925, 2856, 1574, 1517, 1510, 1499, 1489, 1466, 1452, 1446, 1421, 1393, 1377, 1362, 1343, 1299, 1288, 1250, 1244, 1175, 1032, 833 and 769 cm$^{-1}$; NMR (CDCl$_3$, TMS) 7.23, 7.10, 6.85, 6.74, 6.53, 3.95–3.75, 3.65–3.45 and 2.10–1.80δ; CMR(CDCl$_3$, TMS) 158.1, 157.6, 155.7, 133.0, 130.6, 129.2, 129.0, 125.9, 113.5, 113.45, 101.8, 96.4, 55.3, 55.2, 47.6, 46.5, 25.5 and 25.4δ; MS (M+H)$^+$ (found) 470, other ions at m/z 454, 440, 428, 412, 399, 330, 240, 229, 197, 167, 141 and 103.

EXAMPLE 83

6,7-Bis(4-methoxyphenyl)-2,4-di-1-pyrrolidinyl-7H-pyrrolo[2,3-d]pyrimidine monomethanesulfonate (VII-salt)

Following the general procedure of EXAMPLE 36 and making non-critical variations but starting with 6,7-bis(4-methoxyphenyl)-2,4-di-1-pyrrolidinyl-7H-pyrrolo[2,3-d]pyrimidine (VII, EXAMPLE 82, 0.604 g), to give the title compound, mp 209°–210°; NMR (CDCl$_3$, TMS) 7.0, 6.75, 6.54, 3.84, 3.77 and 2.62δ; MS (m/z) calc'd=469.2478, found 469.2486; IR (mineral oil) 3113, 3004, 1634, 1625, 1552, 1511, 1500, 1488, 1446, 1426, 1417, 1410, 1356, 1350, 1296, 1253, 1224, 1216, 1180, 1042, 835, 769, 762, 668 cm$^{-1}$.

EXAMPLE 84

4,4'-(2,4-Di-1-pyrrolidinyl-7H-pyrrolo[2,3-d]pyrimidine-6,7-diyl)bis-phenol (VII)

A mixture of 6,7-bis(4-methoxyphenyl)-2,4-di-1-pyrrolidinyl-7H-pyrrolo[2,3d]pyrimidine (VII, EXAMPLE 82, 200 mg) in 10 ml of 48% hydrobromic acid is refluxed for 30 minutes. The reaction mixture is concentrated under reduced pressure. The resulting residue is partitioned between chloroform and saturated sodium bicarbonate. The organic layer is separated, washed with saline, dried over anhydrous sodium sulfate, and concentrated under reduced pressure. The crude product (132 mg) is recrystallized from 2-propanol/water. The solid is isolated and dried (18 hours, 0.01 mm, 40°) to give the title compound, mp 254°–256°; IR (mineral oil) 3307, 2953, 2923, 2869, 2855, 1614, 1567, 1569, 1515, 1486, 1468, 1455, 1410, 1376, 1356, 1346, 1318, 1266, 1226, 1172, 1106, 835, 768, 638 and 615 cm$^{-1}$; NMR (DMSO-d$_6$, TMS) 9.53, 9.41, 7.05–6.85, 6.74, 6.70–6.50, 3.85–3.60, 3.50–3.20 and 2.05–1.75δ; CMR (DMSO-d$_6$, TMS) 156.1, 155.9, 155.1, 154.9, 132.3, 129.2, 129.1, 128.8, 123.7, 115.1, 100.9, 95.9, 47.5, 47.4, 47.2, 46.2, 46.1, 25.1 and 24.9δ; MS (m/z) calc'd=442.2165, found=442.2284, other ions at m/z 413, 217, 193, 173, 137, 109, 92. 79, 69 and 55.

EXAMPLE 85

4,4'-(2,4-Di-1-pyrrolidinyl-7H-pyrrolo[2,3-d]pyrimidine-6,7-diyl)bis-phenol, hydrobromide salt (VII-salt)

Following the general procedure of EXAMPLE 55 and making non-critical variations but starting with 6,7-bis(4-methoxyphenyl)-2,4-di-1-pyrrolidinyl-7H-pyrrolo[2,3-d]pyrimidine (VII, EXAMPLE 84, 500 mg), the title compound is obtained, mp 298°–300°; NMR (DMSO-d$_6$, TMS) 7.10–666, 4.10–3.40 and 2.15–1.85δ; MS (m/z) M$^+$ observed at 441.2163, other ions observed at m/z 413, 399, 384, 371, 358, 343, 302, 265 and 220.

EXAMPLE 86

5,6-Bis(4-methoxyphenyl)-7-methyl-2,4-di-1-piperazinyl-7H-pyrrolo[2,3-d]pyrimidine (VII)

A suspension of the N-methyl-2,6-di-(4'-t-butoxycarbonyl-1'-piperazinyl)-4-pyrimidinamine (V, EXAMPLE, 42, 4.05 g) in 85 ml of acetonitrile is treated with 1.85 ml of diisopropylethylamine and 2-bromo-1,2-bis(4-methoxyphenyl)ethanone (VI, 2.84 g). The suspension is stirred at 20°–25° for 10 minutes and then heated at reflux for 6.5 hr. The reaction is cooled to 20°–25°. During cooling a solid comes out of the mixture. Filtration of the suspension provides a solid still containing the BOC protecting groups on the piperazine rings, mp 200°–202°. This BOC protected intermediate is dissolved in 90 ml of freshly prepared saturated hydrogen chloride/ethyl acetate. The suspension is stirred for 1 hour at 20°–25°. Hexane/ethyl acetate (90 ml 1/1) is added to the suspension and stirring is continued for 45 minutes. Filtration of the suspension, followed by washing of the solid with hexane/ethyl acetate (1/1) gives 2.45 g of a solid which is chromatographed on silica gel, eluting with chloroform/3.7M ammonia in methanol (92/8). Collection of the desired fractions followed by solvent evaporation and drying gives the title compound, mp 214°–218°; NMR (CDCl$_3$, TMS) 7.07, 6.84, 6.76, 3.81, 3.78, 3.53, 3.15, 1.50, 1.41, 7.08, 6.84, 6.76, 3.80, 3.52, 3.17, 2.97 and 2.58δ; MS (m/z) calc'd=513.2852, found=513.2839; IR (mineral oil) 3300, 1615, 1585, 1573, 1559, 1541, 1516, 1495, 1447, 1438, 1431, 1414, 1409, 1292, 1268, 1258, 1255, 1241, 1177, 1026, 834, 825, 791 cm$^{-1}$.

EXAMPLE 87

5,6-Bis(4-methoxyphenyl)-7-methyl-2,4-di-1-pyrrolidinyl-7H-pyrrolo[2,3-d]pyrimidine dimethanesulfonate (VII-salt)

Following the general procedure of EXAMPLE 36 and making non-critical variations but starting with 5,6-bis(-methoxyphenyl)-7-methyl-2,4-di-1-piperazinyl-7H-pyrrolo[2,3d]pyrimidine (VII, EXAMPLE 86, 0.305 g), the title compound is obtained, mp 202°–205°; NMR (methanol-d$_4$, TMS) 7.11, 6.88, 4.11, 3.79, 3.77, 3.53, 3.39, 2.91 and 2.69δ; IR (mineral oil) 3472, 3013, 1612, 1590, 1584, 1575, 1555, 1544, 1518, 1494, 1443, 1421, 1290, 1273, 1250, 1221, 1211, 1179, 1151, 1041, 772 cm$^{-1}$; MS (m/z) calc'd= 513.2852, found=513.2847.

EXAMPLE 88

5,7-Dihydro-7-methyl-2,4-di-1-pyrrolidinyl-6H-pyrrolo[2,3-d]pyrimidin-6-one (VII)

A stirred mixture of 4-methylamino-2,6-di-1-pyrrolidinopyrimidine (V, EXAMPLE 3, 1.235 g) in 20 ml of oxygen-free ethanol (degassed with argon for 15 minutes) is treated with 600 mg of 2,3-dihydroxy-1,4-dioxane, added in one portion. The resulting mixture is stirred at 25° in a foil-wrapped flask under nitrogen for 22 hours, then cooled to 0°. The solids are isolated by filtration, washed with 2×3 ml of cold ethanol, and dried (2 hours, 0.05 mm, 40°), to give the title compound, mp 172°–174°; IR (mineral oil) 2958, 2925, 2865, 1725, 1605, 1574, 1533, 1489, 1478, 1469, 1456, 1451, 1394, 1388, 1366, 1345, 1333, 1325, 1269, 1261, 1096, 1082, 778 and 636 cm$^{-1}$; NMR (CDCl$_3$, TMS) 3.60–3.52, 3.17 and 1.94–1.89δ; CMR (CDCl$_3$, TMS) 176.3, 164.9, 159.7, 156.2, 82.2, 46.8, 46.4, 35.3, 25.5 and 25.2δ; MS (m/z)=288; other ions at m/z 287, 272, 259, 246, 230, 216, 190, 70 and 55.

EXAMPLE 89

7-Methyl-2,4-di-1-pyrrolidinyl-7H-pyrrolo[2,3-d]pyrimidine (VII)

Diisobutylaluminum hydride (7.3 ml, 1M in toluene) is added to the 5,7-dihydro-7-methyl-2,4-di-1-pyrrolidinyl-6H-pyrrolo[2,3-d]pyrimidin-6-one (VII, EXAMPLE 88, 2.0 g) in methylene chloride (100 ml) at −78° over a 15 minute period. After 4 hours the reaction is quenched by the addition of 5% sulfuric acid (30 ml). The organic layer is removed and extracted with sulfuric acid (5%, 30 ml). The aqueous layer is extracted with methylene chloride (4×30 ml). The organic layers are combined, dried (sodium sulfate), filtered and concentrated under reduced pressure. The residue is chromatographed on silica gel. The column is eluted with ethyl acetate/methylene chloride/hexane (1/4/5). The appropriate fractions are combined and concentrated under reduced pressure to give the title compound, NMR (CDCl$_3$, TMS) 6.51, 6.34, 3.78–3.73, 3.63 and 3.62–3.57δ; MS (m/z)=271.1792.

EXAMPLE 90

2,6-Dichloro-4-[N-methyl—N-(2-oxo-2-phenylethyl)]pyrimidine (CHART B)

A mixture of 2,6-dichloro-4-methylaminopyrimidine (III, EXAMPLE 1) in 250 ml of dimethylformamide is cooled to 0° and treated with 1.12 g of 60% oil dispersion sodium hydride, and the reaction mixture is allowed to warm to 20°–25° over a period of 2 hr. The mixture is then treated with 5.59 g of 2'-bromoacetophenone (VI), and the reaction mixture is allowed to stir at 20°–25° for 5 days. The reaction mixture is concentrated under reduced pressure. The resulting residue is partitioned between chloroform and water. The organic layer is separated, washed with saline, dried over anhydrous sodium sulfate, and concentrated under reduced pressure. The crude product (13.2 g) is chromatographed on 730 g of silica gel. The column is packed and eluted with chloroform/acetone (99/1). An initial fraction of 1500 ml is collected, followed by 10 ml fractions. Based on their TLC homogeneity, fractions 611–680 are combined and concentrated to give the title compound; .NMR (CDCl$_3$, TMS) 7.99, 7.60, 7.53, 6.51, 5.15 and 3.13δ; MS (m/z)=296; other ions at m/z 295, 283, 190, 176, 120, 105, 86, 77 and 42.

EXAMPLE 91

7-Methyl-5-phenyl-2,4-di-1-pyrrolidinyl-7H-pyrrolo[2,3-d]pyrimidine (VII)

A mixture of 2,6-dichloro-4-(N-methyl-N-[2-oxo-2-phenylethyl]pyrimidine (EXAMPLE 90, 560 mg) in pyrrolidine (IV, 4.8 ml) is refluxed for 18 hours. The reaction mixture is concentrated under reduced pressure. Standard workup provided the crude product (1.28 g) which is chromatographed on 180 g silica gel. The column is packed and eluted with chloroform/acetone (95/5). An initial fraction of 225 ml is collected, followed by 7 ml fractions. Based on their TLC homogeneity, fractions 30–50 are combined giveing solid which is recrystallized from ethanol/water, isolated and dried (18 hours, 0.01 mm, 40°) to give the title compound, mp 141°–143°; IR (mineral oil) 2954, 2925, 2867, 2855, 1605, 1582, 1552, 1540, 1517, 1486, 1445, 1438, 1403, 1376, 1366, 1344, 1337, 1244, 788, 761,753, 709, 698, 629 and 607 cm$^{-1}$; NMR (CDCl$_3$, TMS) 7.45–7.20, 6.52, 3.75–3.55, 3.35–3.20, 2.05–1.90 and 1.70–1.50δ; MS (m/z) calc'd=347.2110, found=347.2113, other ions at m/z 319, 305, 290, 277, 264, 249, 222, 207, 173, 152 and 138.

EXAMPLE 92

2,4-Dihydroxypyrrolo[2,3-d]pyrimidine

A stirred suspension of 3-amino-2,6-dihydroxypyrimidine (12.5 g) in 600 ml of water is treated with 10 g of sodium acetate and 12.5 ml of 50% by weight aqueous chloroacetaldehyde. The suspension is heated at reflux for 3.5 hours then cooled to 25°, after which 2N aqueous hydrochloric acid (65 ml) is added. The suspension is filtered and provided 13.65 g of solid.

The above solid is taken up as a suspension in 1.8 L of water and heated to boiling and concentrated to 1.1 liters, then cooled to 20°–25°. After having been at 20°–25° overnight, the suspension is filtered. Drying of the collected solids under high vacuum to give the title compound, NMR (DMSO-d$_6$, TMS) 11.46, 11.11, 10.49, 6.57 and 6.22δ.

EXAMPLE 93

2,4-Dichloro-7H-pyrrolo[2,3-d]pyrimidine

The pyrophosphoryl chloride used in the reaction is prepared in the following manner. A stirred mixture (30 ml) of phosphorus oxychloride is cooled in a cold water bath and treated slowly with 3 ml of water. After the addition is completed, the mixture is heated to reflux. One hour later the mixture is cooled to 25°. An opaque gel settled to the bottom of the flask. The mixture above the gel is the desired reagent.

A mixture of 2,4-dihydroxypyrrolo[2,3-d]pyrimidine (EXAMPLE 92, 1.66 g) and freshly prepared pyrophosphoryl chloride (13.3 ml) are heated together overnight in a stainless steel bomb at 165°. After cooling the bomb to 25°, the black syrup is poured into a 50 ml round bottomed flask. Any volatiles are evaporated under reduced pressure. The remaining black residue is gradually added to 65 g of crushed ice with stirring. After the ice has melted, the resulting suspension is filtered. The filtrate from above is extracted twice with ether. The combined ether extracts are washed with water and dried (sodium sulfate), filtered, and concentrated, followed by drying which gives 41.3 mg of solid. To obtain additional product from the reaction, the filter cake from the first filtration is washed with more ether. The ether filtrate is washed with water and saline followed by drying (sodium sulfate), filtration, and solvent evaporation. This is repeated twice, to give the title compound, mp 245°–248°; NMR (DMSO-d6, TMS) 12.8, 7.74 and 6.67δ; MS (m/z) calc'd=186.9704, found=186.9698.

EXAMPLE 94

2,4-Di-1H-imidazol-1-yl-7H-pyrrolo[2,3-d]pyrimidine (VII)

A stirred suspension of 2,4-dichloro-7H-pyrrolo[2,3-d] pyrimidine (EXAMPLE 93, 0.310 g) and imidazole (1.1 g) in 15 ml of ortho-xylene is slowly heated to reflux. During heating the reagents go into mixture. After 3 hours, the reaction is cooled to 20°–25°, followed by solvent evaporation under high vacuum. This gives a semi-solid which is taken up in chloroform and washed with aqueous sodium bicarbonate (2×) and saline. A solid is suspended at the interface between the aqueous and organic layer. This solid is collected with the organic layer, solvent evaporation gives 2.38 g of a solid which is chromatographed using 150 g of silica gel and eluting with chloroform/3.7M ammonia in methanol (93/7). The solid is loaded on the column as a suspension. Initial fractions of 400 and 150 ml are collected, followed by 10 ml fractions. Fractions 19–45 contained the desired product. Solvent evaporation and drying gives the title compound, mp 276°–280°; NMR (DMSO-d$_6$, TMS) 1265, 8.99, 8.78, 8.36, 8.1, 7.71, 7.28 and 7.16δ; MS (m/z) calc'd=251.0919, found=251.0927; IR (mineral oil) 3149, 3140, 1615, 1584, 1491, 1439, 1421, 1336, 1313, 1268, 1246, 1102, 1059, 1011, 832, 739, 647 cm$^{-1}$.

EXAMPLE 95

2,4-Di-1-pyrrolidinyl-7H-pyrrolo[2,3-d]pyrimidine (VII)

A stirred mixture of 2,4-dichloro-7H-pyrrolo[2,3-d]pyrimidine (EXAMPLE 93, 0.303 g) in 18 ml of pyrrolidine is heated at reflux overnight. Solvent evaporation gives oil which is taken up in chloroform and washed with water and saline. The organic layer is dried (sodium sulfate), filtered, and concentrated, thereby giveing 1.0 g of a solid which is chromatographed on 125 g of silica gel eluting with chloroform/methanol (95/5). An initial fraction of 150 ml is collected, followed by 10 ml fractions. Fractions 19–54 contained the desired product (0.69 g). The above solid is chromatographed two additional times on silica gel eluting with the same solvent system. The final chromatography gives, after drying under high vacuum, the title compound, mp 247°–250°; NMR (CDCl$_3$, TMS) 9.9, 6.66, 6.39, 3.85–3.75, 3.7–3.5 and 2.05–1.9δ; MS (m/z) calc'd=257, found=257.

EXAMPLE 96

2,4-Di-1-pyrrolidinyl-7H-pyrrolo[2,3-d]pyrimidine, monomethanesulfonate (VII-salt)

Following the general procedure of EXAMPLE 36 and making non-critical variations but starting with 2,4-di-1-pyrrolidinyl-7H-pyrrolo[2,3-d]pyrimidine (VII, EXAMPLE 95, 0.223 g), the title compound is obtained, mp 217°–221°; NMR (CDCl$_3$, TMS) 12.55, 12.45, 6.78, 6.38, 3.87, 3.76, 3.63, 2.90 and 2.2–1.95δ; MS (m/z) calc'd=257.1640, found=257.1647.

EXAMPLE 97

2-(2,6-Dichloropyrimidin-4-ylamino)-ethanesulfonic acid (III)

A stirred mixture of 2,4,6-trichloropyrimidine (6.9 g) in 75 ml of tetrahydrofuran is treated with diisopropylethylamine (15 ml) and solid taurine (4.7 g). The resulting suspension is heated at reflux for 48 hours. The reaction mixture is cooled to 20°–25° followed by solvent evaporation which gives 26 g of an oil which is chromatographed on 170 g of silica gel and eluting with chloroform/5.0M ammonia in methanol (7/3). An initial fraction of 250 mL is collected followed by 20 ml fractions. Fractions 23–57 contained the desired product. Solvent evaporation gives a semi-solid which is taken up in chloroform/methanol (10/1) and stirred at 20°–25° for 30 minutes. Filtration provided 3.71 g of a solid.

The oil from the filtrate is rechromatographed on 550 g of 230–400 mesh silica gel using a flash column and the same solvent system as above. Collection of the product fractions followed by solvent evaporation gives a solid which is taken up as a suspension in chloroform and stirred for 1 hour. Filtration of the suspension and drying under high vacuum overnight gives the title compound, mp 206°–211°; NMR (methanol, TMS) 3.77 and 3.07δ.

EXAMPLE 98

2-(2,6-Di-1-pyrrolidinylpyrimidin-4-ylamino)ethanesulfonic acid (V)

The 2-(2,6-dichloropyrimidin-4-ylamino)ethanesulfonic acid (III, EXAMPLE 97, 3.0 g) is dissolved in pyrrolidine (IV, 125 ml) and heated to reflux. Solvent evaporation gives a semisolid which is chromatographed on 155 g of silica gel eluting with chloroform/3.9M ammonia in methanol (7/3). An initial fraction of 150 ml is collected followed by 15 ml fractions. Fractions 8–18 contained the desired product. Solvent evaporation and drying under high vacuum gives a solid (a portion of which) is rechromatographed on 155 g silica gel and eluting with the same solvent system as described above. The appropriate fractions are pooled and concentrated to give the title compound, which is used in subsequent reactions without further purification.

EXAMPLE 99

2-(6-Phenyl-2,4-di-1-pyrrolidinyl-7H-pyrrolo[2,3-d]pyrimidin-7-yl)ethanesulfonic acid (VII)

To a stirred suspension of 2-(2,6-di-1-pyrrolidinylpyrimidin-4-ylamino)ethanesulfonic acid (V, EXAMPLE 98, 1.00 g) in 20 ml of acetonitrile is added 1.0 ml of diisopropylethylamine and phenacyl bromide (VI, 0.583 g). The suspension is heated at reflux overnight, cooled, followed by solvent evaporation, which gives a oil. The oil is chromatographed on 100 g silica gel eluting with chloroform/3.9M ammonia in methanol (75/25). An initial fraction of 100 ml is collected followed by 8 ml fractions. Fractions 31–43 contained the desired product along with starting material and a less polar impurity. Solvent evaporation provided 0.48 g of a semi-solid which is treated with an ether/hexane mixture. After stirring the suspension for 30 minutes the product is filtered. The collected solid is washed with several portions of ether. Drying of the product under high vacuum gives the title compound, a portion of the product is recrystallized from water/absolute ethanol (85/15), mp >300°; NMR (CDCl$_3$, TMS) 7.46–7.35, 6.44, 4.35, 3.88–3.65, 3.32 and 2.12–1.90δ; IR (mineral oil) 3466, 1635, 1598, 1542, 1421, 1396, 1353, 1311, 1239, 1226, 1188, 1155, 1036 and 747 cm$_{-1}$; MS (m/z) calc'd=441.1834, found=441.1841.

EXAMPLE 100

2-Bromo-3',4'-dimethoxyacetophenone (VI)

Following the general procedure of EXAMPLE 59 and making non-critical variations but starting with 3',4'-dimethoxyacetophenone, the title compound is obtained, mp 79.5°–81.0°; NMR (CDCl$_3$, TMS) 7.61, 6.92, 4.42, 3.97, 3.95δ.

EXAMPLE 101

6-(3,4-Dimethoxyphenyl)-7-methyl-2,4-di-1-pyrrolidinyl-7H-pyrrolo [2,3-d]pyrimidine (VII)

Following the general procedure of EXAMPLE 40 and making non-critical variations but starting with 4-methylamino-2,6-di-1-pyrrolidinopyrimidine (V, EXAMPLE 1, 3.81 g) and 2-bromo-3',4'-dimethoxyacetophenone (VI, EXAMPLE 100, 3.99 g), the title compound is obtained, mp 175°–178°; NMR (CDCl$_3$ TMS) 6.95, 6.36, 3.92, 3.80, 3.66, 1.96δ.

EXAMPLE 102

6-(3,4-Dimethoxyphenyl)-7-methyl-2,4-di-1-pyrrolidinyl-7H-pyrrolo[2,3-d]pyrimidine monomethanesulfonate (VII-salt)

Following the general procedure of EXAMPLE 36 and making non-critical variations but starting with 6-(3,4-dimethoxyphenyl)-7-methyl-2,4-di-1-pyrrolidinyl-7H-pyrrolo[2,3d]pyrimidine (VII, EXAMPLE 101, 0.96 g), the title compound is obtained, mp 182°–185°; NMR (DMSO-d6) 7.05, 6.71, 3.81–3.62, 2.28, 1.96; HRMS (m/z) M$^+$ observed=407.2337, calculated for C$_{23}$H$_{29}$N$_5$O$_2$=407.232 1, other ions observed at m/z 392, 379, 352, 203, 182.

EXAMPLE 103

4-(7-Methyl-2,4-di-1-pyrrolidinyl-7H-pyrrolo[2,3-d]pyrimidin-6-yl)-1,2-benzenediol monohydrobromide (VII-salt)

Following the general procedure of EXAMPLE 55 and making non-critical variations but starting with 6-(3,4-dimethoxyphenyl)-7-methyl-2,4-di-1-pyrrolidinyl-7H-pyrrolo[2,3-d]pyrimidine (VII, EXAMPLE 101, 1.0699 g), the title compound is obtained, mp 232°–235°; a small sample is recrystallized from 95% ethanol to obtain an analytical sample, NMR (CD$_3$OD) 6.88–6.79, 6.56, 3.88, 3.69, 2.05δ; HRMS (EI, m/z) M$^+$ observed=379.2013, calculated for C$_{21}$H$_{25}$N$_5$O$_2$=379.2008, other ions observed at m/z 351,322, 40; IR (mineral oil) 3520, 3162, 1684, 1280, 1114 cm$^{-1}$.

EXAMPLE 104

6-(2,5-Dimethoxyphenyl)-7-methyl-2,4-di-1-pyrrolidinyl-7H-pyrrolo[2,3-d]pyrimidine (VII)

Following the general procedure of EXAMPLE 40 and making non-critical variations but starting with 4-methylamino-2,6-di-1-pyrrolidinopyrimidine (V, EXAMPLE 3, 2.8 g) and 2-bromo-2,'5'-dimethoxyacetophenone (VI, Aldrich Chemical Co., 2.92 g), the title compound is obtained, mp 140°–142°; NMR (CDCl$_3$, TMS) 6.58, 6.37, 3.79–3.74, 3.62, 3.50, 2.04–1.94δ.

EXAMPLE 105

2-(7-Methyl-2,4-di-1-pyrrolidinyl-7H-pyrrolo[2,3-d]pyrimidin-6-yl)-1,4-benzenediol, monohydrobromide (VII-salt)

Following the general procedure of EXAMPLE 103 and making non-critical variations but starting with 6-(2,5-dimethoxyphenyl)-7-methyl-2,4-di-1-pyrrolidinyl-7H-pyrrolo[2,3d]pyrimidine (VII, EXAMPLE 104), the title compound is obtained, mp 295°–299°; NMR (CD$_3$OD) 6.68–6.60, 6.48, 3.79, 3.61, 3.52, 1.96δ; HRMS (EI, m/z) M$^+$ observed=379.2004, calculated for C$_{21}$H$_{25}$N$_5$O$_2$, =379.2008, other ions observed at m/z 351, 324, 70; IR (mineral oil) 3167, 1688, 1496, 1275, 1195 cm$^{-1}$.

EXAMPLE 106

2-Bromo-2'-fluoro-4'-methoxyacetophenone (VI)

Following the general procedure of EXAMPLE 100 and making non-critical variations but starting with 2'fluoro-4'-methoxyacetophenone (Aldrich Chemical Co.), the title compound is obtained, mp 67°–69°; NMR (CDCl$_3$, TMS) 7.95, 6.79, 6.64, 4.48δ; HRMS (EI, m/z) calculated for C$_9$H$_8$BrFO$_2$ M$^+$ found=246 and 248.

EXAMPLE 107

6-(2-Fluoro-4-methoxyphenyl)-7-methyl-2,4-di-1-pyrrolidinyl-7H-pyrrolo[2,3-d]pyrimidine (VII)

Following the general procedure of EXAMPLE 104 and making non-critical variations but starting with 4-methylamino-2,6-di-1-pyrrolidinopyrimidine (V, EXAMPLE 3) and 2-bromo-2'-fluoro-4'-methoxyacetophenone (VI, EXAMPLE 106), the title compound is obtained, mp 168.5°–169.5°; NMR (CDCl$_3$, TMS) 7.28, 6.37, 3.84, 3.78, 3.62, 3.54, 1.95δ; HRMS (EI, m/z) Calculated for C$_{22}$H$_{26}$FN$_5$O=395, found=395; IR (mineral oil): 3063, 1626, 1577, 1562, 1523, 1492, 1485, 1480, 1444, 1403, 1357, 1347, 1296, 1251, 1158, 1123, 1042, 873, 815, 774 cm$^{-1}$.

EXAMPLE 108

6-(2-Fluoro-4-methoxyphenyl)-7-methyl-2,4-di-1-pyrrolidinyl-7H-pyrrolo[2,3-d]pyrimidine monomethanesulfonate (VII-salt)

Following the general procedure of EXAMPLE 36 and making non-critical variations but starting with 6-(2-fluoro-4-methoxyphenyl)-7-methyl-2,4-di-1-pyrrolidinyl-7H-pyrrolo[2,3-d]pyrimidine (VII, EXAMPLE 107), the title compound is obtained, mp 165.5°–167.5°; NMR (CDCl$_3$ TMS) 7.24, 6.75, 6.43, 3.8, 2.78, 2.05δ; HRMS (EI, m/z) Calculated for C$_{22}$H$_{26}$FN$_5$O (M)+ free base=395.2121, found= 395.2119; IR (mineral oil): 3447, 1628, 1596, 1579, 1556, 1542, 1495, 1416, 1360, 1339, 1323, 1307, 1254, 1231, 1171, 1104, 1041, 947, 833, 768, 756 cm$^{-1}$.

EXAMPLE 109

6-(2-Methoxyphenyl)-7-methyl-2,4-di-1-pyrrolidinyl-7H-pyrrolo[2,3-d]pyrimidine (VII)

Following the general procedure of EXAMPLE 104 and making non-critical variations but starting with 4-methylamino-2,6-di-1-pyrrolidinopyrimidine (V, EXAMPLE 3) and 2-bromo-2'-methoxyacetophenone (VI, Aldrich Chemical Co.), the title compound is obtained, NMR (CDCl$_3$ TMS) 7.26, 6.91, 6.28, 3.72, 3.56, 3.42, 1.87δ.

EXAMPLE 110

2-(7-Methyl-2,4-di-1-pyrrolidinyl-7H-pyrrolo [2,3-d]pyrimidin-6-yl)phenol, monohydrobromide (VII-salt)

Following the general procedure of EXAMPLE 103 and making non-critical variations but starting with 6-(2-methoxyphenyl)-7-methyl-2,4-di-1-pyrrolidinyl-7H-pyrrolo[2, 3d]pyrimidine (VII, EXAMPLE 109), the title compound is obtained, mp 203°–206°; NMR (CDCl$_3$, TMS) 7.25, 1196.93, 6.58, 3.88, 3.70, 3.60, 2.08δ; HRMS (EI, m/z) M+ observed=363.2062, calculated for C$_{21}$H$_{25}$N$_5$O=363.2059, other ions observed at m/z 335, 308, 181, 160, 82; IR (mineral oil) 3433, 3367, 3059, 1631, 1540, 1285, 756 cm$^{-1}$.

EXAMPLE 111

2-Bromocyclohexanone (VI)

A mixture of cyclohexanone (3.25 ml) in 30 ml ethyl acetate/chloroform (1/1) is prepared in a 100 ml flask. To this stirring mixture, copper bromide (13.96 g) is added as a solid in one portion. The contents of the flask were brought to reflux for 1.25 hours. The reaction is then cooled to 20°–25° followed by filtration. The filtrate is washed with 3×20 ml portions of saturated sodium bicarbonate mixture. The organic layer is dried over sodium sulfate, filtered, and the solvent is removed under reduced pressure. An oil (4.29 g) is obtained which is chromatographed on 455 g of silica gel. The eluent (3.5 l) is ethyl acetate/hexane (19/1) followed by (9/1, 1.5 l). Like fractions were combined based on TLC homogeneity and concentrated to give the title compound, NMR (CDCl$_3$, TMS) 4.45, 3.04–2.94, 2.39–2.19, 2.05–1.94, 1.87–1.71δ.

EXAMPLE 112

5,6,7,8-Tetrahydro-9-methyl-2,4-di-1-pyrrolidinyl-5H-pyrimido[4,5-b]indole (VII)

A mixture of 4-methylamino-2,6-di-1-pyrrolidinopyrimidine (V, EXAMPLE 3, 1.54 g), diisopropylethylamine (1.15 ml) and 80 ml acetonitrile is prepared in a 200 ml flask. 2-Bromocyclohexanone (VI, EXAMPLE 111, 1.11 g) is added to the stirring mixture at 20°–25°. The reaction is heated at reflux for 29 hr. The contents of the flask were cooled to 0°. A solid precipitated, is collected by filtration and dried to give the title compound, mp 196°–200°; NMR (CDCl$_3$, TMS) 3.68, 3.59, 3.51, 2.72, 2.61, 1.94–1.77δ.

EXAMPLE 113

5,6,7,8,Tetrahydro-9-methyl-2,4-di-1-pyrrolidinyl-5H-pyrimido[4,5-b]indole, monomethanesulfonate (VII-salt)

Following the general procedure of EXAMPLE 36 and making non-critical variations but starting with 5,6,7,8-tetrahydro-9-methyl-2,4-di-1-pyrrolidinyl-5H-pyrimido[4, 5-b]indole (VII, EXAMPLE 112), the title compound is obtained, mp 178°–182°; NMR (CDCl$_3$, TMS) 3.81–3.73, 2.78, 2.67, 2.57, 2.01–1.76δ; HRMS (EI, m/z) M+ observed=325.2273, calc'd for C$_{19}$H$_{27}$N$_5$=325.2266, other ions observed at m/z 297, 270, 256, 162, 141. IR (mineral oil) 2269, 1625, 1569, 1442, 1247, 1164, 1036, 766 cm$^{-1}$.

EXAMPLE 114

2-Bromo-1-pyridin-2-ylethanone hydrobromide (VI)

A mixture of bromine (4.28 ml) in 30 ml of carbon tetrachloride is added dropwise via addition funnel to a boiling mixture of 2-acetylpyridine (9.25 ml, Aldrich Chemical Co.) and carbon tetrachloride (65 ml). Addition is completed in 2 hr and within 15 minutes a solid began forming. Reflux continued for another 40 minutes before the reaction vessel is cooled to 0°. The solid precipitate is collected by filtration and dried (400°, 0.03 mm) for 3 hours to give the title compound, mp 212°–213°; NMR (CD$_3$OD) 8.83–8.15, 3.86δ.

EXAMPLE 115

6-(2-Pyridinyl)-7-methyl-2,4-di-1-pyrrolidinyl-7H-pyrrolo [2,3-d]pyrimidine (VII)

Following the general procedure of EXAMPLE 104 and making non-critical variations but starting with 4-methylamino-2,6-di-1-pyrrolidinopyrimidine (V, EXAMPLE 3) and 2-bromo-1-pyridin-2-yl-ethanone hydrobromide (VI, EXAMPLE 114), the title compound is obtained, mp 243°–247°; NMR (CDCl$_3$, TMS) 8.58, 7.64–7.54, 7.08, 6.80, 3.97, 3.81, 3.63, 1.95δ; HRMS (EI, m/z) M+ observed= 348; calculated for C$_{20}$H$_{24}$N$_6$=348.2062, other ions observed at m/z 320, 306, 293, 279, 174, 153; IR (mineral oil): 2956, 1570, 1537, 1478, 1360, 765 cm$^{-1}$.

EXAMPLE 116

5-Acetyl-2-methoxybenzoic acid methyl ester

A mixture of 5-acetyl salicylic acid (1.46 g), DMF (10 ml), and potassium carbonate (1.1281 g) is stirred at 20°–25° while adding iodomethane (1.55 ml) via pipette. The reaction mixture is placed under a nitrogen atmosphere and stirred at 20°–25° for 65 hr. Additional iodomethane (0.76 ml) and potassium carbonate (1.14 g) were added, and the reaction is permitted to stir for another 24 hr. The reaction mixture is poured onto 35 ml of 1N hydrochloric acid and extracted with 3.35 ml portions of ether. The organic layers were combined and washed with cold water and cold sodium bicarbonate before being dried with sodium sulfate. Solvent is removed under reduced pressure giveing a solid which is placed in the oven (40°, 0.05 mm) for 24 hours to give the title compound, mp 72°–74°; NMR (CDCl$_3$, TMS) 8.41, 8.12, 7.03, 3.98, 3.92, 2.59δ.

EXAMPLE 117

5-Bromoacetyl-2-methoxy-benzoic acid methyl ester (VI)

Following the general procedure of EXAMPLE 100 and making non-critical variations but starting with 5-acetyl-2-methoxybenzoic acid methyl ester (EXAMPLE 116, the title compound is obtained, NMR (CDCl$_3$, TMS) 8.44, 8.15, 7.07, 4.23, 4.00, 3.93δ.

EXAMPLE 118

2-Methoxy-5-(7-methyl-2,4-di-pyrrolidin-1-yl-7H-pyrrolo[2,3-d]pyrimidin-6-yl)benzoic acid methyl ester (VII)

Following the general procedure of EXAMPLE 104 and making non-critical variations but starting with 4-methylamino-2,6-di-1-pyrrolidinopyrimidine (V, EXAMPLE 3) and 5-bromoacetyl-2-methoxy-benzoic acid methyl ester (VI, EXAMPLE 117), the title compound is obtained, mp 168°–170°; NMR (CDCl$_3$, TMS): δ7.90, 7.55, 7.05, 6.39, 3.95, 3.911, 3.79, 3.63, 1.95.

EXAMPLE 119

2—Hydroxy-5-(7-methyl-2,4-di-pyrrolidin-1-yl-7H-pyrrolo[2,3-d]pyrimidin-6-yl)-benzoic acid monohydrobromide (VII-salt)

Following the general procedure of EXAMPLE 103 and making non-critical variations but starting with 2-methoxy-5-(7-methyl-2,4-di-pyrrolidin-1-yl-7H-pyrrolo[2,3-d]pyrimidin-6-yl)benzoic acid methyl ester (VII, EXAMPLE 118), the title compound is obtained, mp 258°–267°; NMR (CD$_3$OD, TMS) 7.86, 7.51, 6.96, 6.58, 3.80, 3.61, 2.01δ; HRMS (EI, m/z) M$^+$ observed =407, calculated for C$_{22}$H$_{26}$BrN$_5$O$_3$=407, other ions observed at m/z 389, 361, 333, 70, 44; IR (mineral oil) 3650, 3611, 3476, 1676, 1627, 1591, 1537, 1402, 1365, 1355, 1299, 1181, 839, 805, 787, 754 cm$^{-1}$.

EXAMPLE 120

4,4'-(7-methyl-2,4-di-1-pyrrolidinyl-7H-pyrrolo[2,3-d]pyrimidin-5,6-diyl)-bis-phenol trihydrobromide (VII-salt)

Following the general procedure of EXAMPLE 103 and making non-critical variations but starting with 5,6-bis(4-methoxyphenyl)-7-methyl-2,4-di-1-piperazinyl-7H-pyrrolo[2,3d]pyrimidine (VII, EXAMPLE 86), the title compound is obtained, mp >300°; NMR(methanol-d$_1$, TMS) 7.01, 6.76, 4.15, 3.57, 3.40, 2.99δ; CMR (CDCl$_3$, TMS) 160.7, 159.2, 158.0, 152.3, 146.6, 136.7, 133.6, 132.7, 126.6, 121.7, 116.6, 116.5, 116.1, 99.5, 47.0, 44.4, 44.1, 41.7, 32.0; MS (EI, m/z) Calculated for C$_{27}$H$_{31}$N$_7$O$_2$ M$^+$ free base= 485.2539, found 485.2537.

EXAMPLE 121

6-(4-Methoxyphenyl)-7-methyl-2,4-bis-piperazin-1-yl-7H-pyrrolo[2,3-d]pyrimidine (VII)

Following the general procedure of EXAMPLE 86 and making non-critical variations but starting with p-methoxyphenacyl bromide (VI), the title compound is obtained, mp 168°–170.5°; NMR (CDCl$_3$, TMS) 7.39, 6.96, 6.29, 3.85, 3.77, 3.64, 2.97δ; MS (EI, m/z) calculated for C$_{22}$H$_{29}$N$_7$O M$^+$=407, found=407; IR (mineral oil) 1578, 1570, 1554, 1542, 1498, 1492, 1446, 1438, 1429, 1399, 1364, 1304, 1257, 1245, 1181, 1006, 809, 771 cm$^{-1}$.

EXAMPLE 122

6-(4-Methoxyphenyl)-7-methyl-2,4-bis-piperazin-1-yl-7H-pyrrolo[2,3-d]pyrimidine dimethanesulfonate (VII)

A mixture of 6-(4-methoxyphenyl)-7-methyl-2,4-bis-piperazin-1-yl-7H-pyrrolo[2,3-d]pyrimidine (VII, EXAMPLE 121, 1.480 g) in 150 ml of isopropanol water (95/5) is treated with 0.705 g of methanesulfonic acid. The mixture is stirred at 20°–25° under nitrogen for 2.5 hr. Solvent evaporation and drying under high vacuum gives a foam which is treated with chloroform and then hexane/ethyl acetate (1/1). In each case the solvent is evaporated. The solid is suspended in hexane/ethyl acetate (1/1) and stirred for 1 hr. Filtration and drying under high vacuum overnight gives the title compound, mp 273°–282°; NMR (D$_{20}$) 7.35, 6.97, 6.41, 4.11, 4.02, 3.82, 3.53, 3.35, 2.78δ; CMR (methanol-d$_1$, TMS) 161.2, 157.6, 157.1, 137.9, 131.3, 125.5, 115.2, 98.7, 55.9, 44.6, 44.5, 44.0, 43.0, 39.6, 30.5δ.

EXAMPLE 123

4-(7-Methyl-2,4-di-piperazinyl-7H-pyrrolo[2,3-d]pyrimidin-6-yl)phenol trihydrobromide (VII-salt)

Following the general procedure of EXAMPLE 103 and making non-critical variations but starting with 6-(4-methoxyphenyl)-7-methyl-2,4-bis-piperazin-1-yl-7H-pyrrolo[2, 3d]pyrimidine (VII, EXAMPLE 121), the title compound is obtained, mp >300°; NMR (D$_2$O) 7.12, 6.71, 6.31, 3.99, 3.85, 3.38, 3.18δ; CMR(D$_2$O; TSP) 155.7, 155.6, 151.4, 145.3, 136.6, 129.9, 122.0, 115.1, 97.1, 42.9, 42.8, 42.6, 31.5δ; MS (EI, m/z) calculated for C$_{21}$H$_{27}$N$_7$O M$^+$ free base=393.2277, found=393.2290; IR (mineral oil) 3345, 2791, 1634, 1597, 1587, 1502, 1330, 1289, 1181, 1143, 847, 760 cm$^{-1}$.

EXAMPLE 124

2,4-Bis[3-(1,1-dimethylethoxycarbonyl)amino-1-pyrrolidinyl]-6-methylaminopyrimidine (V)

The 2,6-dichloro-4-methylaminopyrimidine (III, EXAMPLE 1, 3.8375 g) is suspended in 200 ml of o-xylene. Diisopropylethylamine (9.4 ml) is added, followed by 3-(t-BOC amino)pyrrolidine (IV, 10.044 g). The reaction contents were placed under a nitrogen atmosphere and heated at reflux. Within 30 minutes, the mixture is homogeneous. The reaction mixture is cooled to 20°–25°. The solvent is removed under reduced pressure, and the residue is dissolved in chloroform. The organic phase is washed with saturated sodium bicarbonate, and saline and dried over sodium sulfate. Removal of the solvent left an oil. Hexane (50 ml) is added and then evaporated yielding a semi-solid. The semi-solid is chromatographed on 800 g of silica gel eluting with chloroform/acetone (9/1) followed by (8/2) and (6/4). A final portion of chloroform/methanol (95/5) is used to finish eluting the second product. Common fractions were combined based on TLC homogeneity and concentrated to give the title compound, mp 90°–95° (decomp); NMR (CDCl$_3$, TMS) 4.70, 4.27, 3.75–3.30, 2.83, 1.89, 1.44δ; MS (EI, mz/) M$^+$ observed=477, calculated for C$_{23}$H$_{39}$N$_7$O$_4$= 477, other ions observed at m/z 360, 305, 243, 217, 57, 40.

EXAMPLE 125

6-(4-Methoxyphenyl)-7-methyl-2,4-bis[3-(1,1-dimethylethoxycarbonyl)-amino-1-pyrrolidinyl]-7H-pyrrolo[2,3-d]pyrimidine (VII)

Following the general procedure of EXAMPLE 104 and making non-critical variations but starting with 2,4-bis[3-(1,1-dimethylethoxycarbonyl)amino-1-pyrrolidinyl]-6-methylaminopyrimidine (V, EXAMPLE 124) and p-methoxyphenacyl bromide (VI), the title compound is obtained, mp 178°–185°; NMR (CDCl$_3$, TMS) 7.37, 6.95, 6.32, 4.71, 3.86–3.63δ.

EXAMPLE 126

2,4-Bis(3-amino-1-pyrrolidinyl)-6-(4-methoxyphenyl)-7-methyl-7-H-pyrrolo[2,3-d]pyrimidine trihydrochloride (VII-salt)

A 250 ml flask is charged with 125 ml of ethyl acetate and chilled to 0°. With stirring, hydrogen chloride gas is bubbled into the ethyl acetate until saturated. At that time, 6-(4-methoxyphenyl)-7-methyl-2,4-bis[3-(1,1-dimethylethoxycarbonyl)- amino-1-pyrrolidinyl]-7H-pyrrolo[2,3-d]pyrimidine (VII, EXAMPLE 125, 1.23 g) is added with stirring at 0°. Soon after the mixture becomes homogeneous, a solid begins precipitating. The reaction is warmed to 20°–25° and stirred for 3.75 hr. The solid material is collected by filtration and rinsed with several portions of ice cold ethyl acetate. Subsequent drying (0.05 mm, 40°) for 24 hours gives the title compound, mp 259° (decomp); NMR (CD$_3$OD, TMS) 7.44, 7.06, 6.60, 4.23–3.91, 3.86, 3.76, 2.56, 2.31δ; MS (EI, m/z) M$^+$ observed=407, calculated for C$_{22}$H$_{29}$N$_7$O=407.

EXAMPLE 127

4-[2,4-Bis-(3-amino-1-pyrrolidinyl)-7-methyl-7H-pyrrolo[2,3-d]pyrimidin-6-yl]phenol trihydrobromide (VII-salt)

Following the general procedure of EXAMPLE 103 and making non-critical variations but starting with 6-(4-methoxyphenyl)-7-methyl-2,4-bis[3-(1,1-dimethylethoxycarbonyl)-amino-1-pyrrolidinyl]-7H-pyrrolo[2,3-d]pyrimidine (VII, EXAMPLE 125), the title compound is obtained, mp 267° decomp; NMR (CD$_3$OD, TMS) 7.34, 6.91, 6.65, 4.19–3.91, 2.58, 2.32δ; MS (EI, m/z) M$^+$ observed=393, calculated for C$_{21}$H$_{27}$N$_7$O=393.

EXAMPLE 128

6-(4-Methoxyphenyl)-7-methyl-2,4-di-1-pyrrolidinyl-7H-pyrrolo[2,3-d]pyrimidine-5-carbaldehyde (VII)

Vilsmeier reagent is prepared by addition of phosphorous oxychloride (3.68 ml) to ice cold DMF (3.1 ml) and the mixture is stirred at ice bath temperature for 10 min. The reagent (ca. 6.5 ml) is slowly added to a stirred mixture of 6-(4-methoxyphenyl)-7-methyl-2,4-di-1-pyrrolidinyl-7H-pyrrolo[2,3-d]pyrimidine (VII, EXAMPLE 50, 4.5 g), DMF (4.5 ml), and THF (40 ml) at 20°–25°. The resultant mixture is stirred for 30 min and then the concentrated under reduced pressure. The residue is chilled in an ice bath, ice (100 g) is added, and the pH is adjusted to 12 with potassium hydroxide pellets. The mixture is diluted with dichloromethane (200 ml) and the phases were separated. The organic phase is dried (sodium sulfate) and concentrated under reduced pressure to give a solid which is recrystallized twice from chloroform/ethyl acetate mixtures to give the title compound, mp 206°–209°; NMR (CDCl$_3$) 9.46, 7.38, 7.02, 3.88, 3.80, 3.60, 3.50, 1.94, 1.85; MS (EI, m/z) 405 (M)$^+$, 377, 349, 307; IR (mineral oil) 1652 cm$^{-1}$.

EXAMPLE 129

6-(4-Methoxyphenyl)-7-methyl-2,4-di-1-pyrrolidinyl-7H-pyrrolo[2,3-d]pyrimidin-5-yl]methanol (VII)

Sodium borohydride (0.04 g) is added to a stirred mixture of the 6-(4-methoxyphenyl)-7-methyl-2,4-di-1-pyrrolidinyl-7H-pyrrolo[2,3-d]pyrimidine-5-carbaldehyde (VII, EXAMPLE 128, 100 mg) in methanol (5 ml) under an argon blanket at 20°–25°. After 1 hr additional sodium borohydride (40 mg) is added and the reaction mixture is stirred for 16 hr at 20°–25°. After 1 hour additional sodium borohydride (0.12 g) were added over an additional 8 hours. The mixture is diluted with an aqueous 8% mixture of sodium hydroxide and dichloromethane. The phases were separated. The aqueous phase is extracted twice again and dichloromethane. The combined dichloromethane extracts were dried (sodium sulfate) and concentrated under reduced pressure to a foam which is crystallized from ethyl acetate to give 0.067 g of the title compound, mp 169°–170°; NMR (CDCl$_3$) 7.27, 6.98, 3.87, 3.81, 3.61, 3.47, 1.95δ; IR (mineral oil) 3274 cm$^{-1}$.

EXAMPLE 130

6-(4-Methoxyphenyl)-7-methyl-2,4-di-1-pyrrolidinyl-7H-pyrrolo[2,3-d]pyrimidine-5-carbaldehyde oxime (VII)

A mixture of 6-(4-methoxyphenyl)-7-methyl-2,4-di-1-pyrrolidinyl-7H-pyrrolo[2,3d]pyrimidine-5-carbaldehyde (VII, EXAMPLE 128, 1.0 g), hydroxylamine hydrochloride (0.307 g), and sodium acetate (0.63 g) in ethanol (18 ml) and water (2 ml) is refluxed for 8 hours. The mixture is cooled and concentrated under reduced pressure to a solid residue which is diluted with water (7 ml), swirled for a couple of minutes, filtered, and the solid is washed with cold water (3×5 ml). The product is air dried on the filter for 15 min, and then in a vacuum oven at 50° for 2 hours to give the title compound, mp 226°–227°; NMR (CDCl$_3$) 9.46, 7.38, 7.02, 3.88, 3.80, 3.60, 3.50, 1.94, 1.85δ; MS (EI, m/z) 420, 403, 404, 402, 386.

EXAMPLE 131

6-(4-Methoxyphenyl)-7-methyl-2,4-di-1-pyrrolidinyl-7H-pyrrolo[2,3-d]pyrimidine-5-carbonitrile (VII)

A mixture of the 6-(4-methoxyphenyl)-7-methyl-2,4-di-1-pyrrolidinyl-7H-pyrrolo[2,3d]pyrimidine-5-carbaldehyde oxime (VII, EXAMPLE 130, 0.74 g) and dimethylformamide (20 ml) is refluxed under nitrogen for 20 hours. The mixture is cooled to 20°–25° and concentrated under reduced pressure to a residue which is triturated with ether to give 0.47 g of solids. The solids were diluted with a chloroform/dichloromethane (1/1) mixture and dilute aqueous sodium bicarbonate mixture. The phases were separated and concentrated to a residue which is flash chromatographed (silica gel, methanolchloroform 1/99). The appropriate fractions are pooled and concentrated to give a solid which is recrystallized from a hot acetone and hexane mixture to give the title compound, mp 230°–231°; NMR (CDCl$_3$) 7.45, 7.03, 3.88, 3.58, 1.97δ.

EXAMPLE 132

4-(7-Methyl-2,4-di-1-pyrrolidinyl-7H-pyrrolo[2,3-d]Pyrimidin-6-yl)phenol (VII)

4-(7-Methyl-2,4-di-1-pyrrolidinyl-7H-pyrrolo[2,3-d]pyrimidin-6-yl)phenol hydrobromide salt (VII, EXAMPLE 55, 8.29 g) is suspended with stirring in 500 ml absolute ethanol. Propylene oxide (16 ml) is added via pipette at 20°–25°. The reaction is heated at reflux for 1.5 hours, then cooled to 0°. The solids that had formed were filtered and dried (0.05 mm, 40°) overnight gives the title compound, mp 268°–272°; NMR (DMSO-$d_6$) 9.57, 7.34, 6.83, 6.37, 3.68, 3.55, 3.50, 1.96–1.85$\delta$.

EXAMPLE 133

2,6-Bis(1-pyrrolidinylmethyl)-4-(7-methyl-2,4-di-1-pyrrolidinyl-7H-pyrrolo[2,3-d]pyrimidin-6- yl)phenol (VII)

A 50 ml flask is charged with the 4-(7-methyl-2,4-di-1-pyrrolidinyl-7H-pyrrolo[2,3d]pyrimidin-6-yl)-phenol (VII, EXAMPLE 132, 510.1 mg) and 11 ml of absolute ethanol. To the resulting suspension is added 37% aqueous formaldehyde (1.15 ml) followed by pyrrolidine (0.85 ml) all at 20°–25°. The reaction mixture is placed under a nitrogen atmosphere and heated at reflux. After 3 hours of reflux and the addition of 4 ml absolute ethanol, all of the solid went into mixture. After a total of 5.5 hours of reflux, the reaction is cooled to 0°. The reaction mixture is concentrated under reduced pressure resulting in a solid which is chromatographed on 170 g of silica gel eluting with 4.5M ammonia in methanol/chloroform (5/95). An initial fraction of 250 ml is collected followed by 14 ml fractions. Fractions 21–61 were combined and concentrated to give the title compound, mp 167°–169°; NMR (CDCl$_3$, TMS) 7.16, 6.34, 3.81, 3.62, 1.94, 1.84$\delta$; MS (EI, m/z) M$^+$ observed=529, calculated for $C_{31}H_{43}N_7O$=other ions observed at 458, 389, 70, 42, 27.

EXAMPLE 134

6,7-Dimethyl-2,4-di-1-pyrrolidinyl-7H-pyrrolo[2,3-d]pyrimidine monohydrochloride (VII-salt)

Ethyl acetate (50 ml) is cooled to 0°. With Stirring, hydrogen chloride gas is bubbled into the ethyl acetate until saturated. 6,7-Dimethyl-2,4-di-1-pyrrolidinyl-7H-pyrrolo[2,3d]pyrimidine (VII, EXAMPLE 52, 238.8 mg) is added in one portion at 0°. After 20 minutes of stirring the mixture becomes homogenous. The mixture is warmed to 20°–25°, and stirred for 1.5 hr. The solvent is removed and a solid is obtained. The solid is triturated with ethyl acetate (30 ml), collected and dried (0.05 mm, 40°) to give a crude product. The product is collected and dried (0.02 mm, 40°) overnight to give the title compound, mp 241°–245° (decomp).

EXAMPLE 135

2,6-Di-1-pyrrolidinyl-4-ethylaminopyrimidine (V)

Following the general procedure of EXAMPLE 1 and making non-critical variations but using ethylamine hydrochloride instead of methylamine hydrochloride, and subsequently following the general procedure of EXAMPLE 3 and making non-critical variations, the title compound is obtained, NMR (CDCl$_3$) 6.27, 3.6–3.2, 1.27; CMR (CDCl$_3$) 204.65, 164.07, 159.60, 36.80 and 14.26.

EXAMPLE 136

7-Ethyl-6-isopropyl-2,4-di-1-pyrrolidinyl-7H-pyrrolo[2,3-d]pyrimidine (VII)

Following the general procedure of EXAMPLE 6 and making non-critical variations but starting with 2,6-dichloro-4-ethylaminopyrimidine (V, EXAMPLE 135) and 1-bromo-3-methyl-2-butanone (*Org. Synth.*, Vol 55, p 24), the title compound is obtained.

EXAMPLE 137

7-Ethyl-6-isopropyl-2,4-di-1-pyrrolidinyl-7H-pyrrolo[2,3-d]pyrimidine sulfate (VII) 7-Ethyl-6-isopropyl-2,4-di-1-pyrrolidinyl-7H-pyrrolo[2,3-d]pyrimidine (VII, EXAMPLE 136) and exactly one equivalent of sulfuric acid followed by recrystallization from ethyl acetate, ethanol and hexane gives the title compound, mp 208°–210°; IR (mineral oil) 3046, 1626, 1595, 1557, 1476, 1351, 1241, 1155, 1063 and 1165 cm$^{-1}$ cm.

EXAMPLE 138

9-Methyl-2,4-di-1-pyrrolidinyl-9H-pyrimido[4,5-b]indole

A suspension of 5,6,7,8-tetrahydro-9-methyl-2,4-di-1-pyrrolidinyl-5H-pyrimido[4,5b]indole (VII, EXAMPLE 112, 1.86 g) and palladium-on-carbon (10%, 1.52 g) in decalin (225 ml) is heated at reflux for 45 min. After cooling chromatographic purification [silica gel, hexane, then acetone/methylene chloride (2/98)] followed by recrystallization (methylene chloride/hexane) gives the title compound, mp 153°–154°; NMR (CDCl$_3$) 7.88, 7.23, 7.10, 3.92, 3.75, 3.65 and 1.95; HRMS (EI) M$^+$ observed at m/z 321.1957, calc'd for $C_{19}H_{23}N_5$=321.1953.

Following the general procedure outlined in EXAMPLES 12–13, 25–27 and 30–34 and making noncritical variations but using 2-[(2,6-di-(1-pyrrolidinyl)pyrimidin-4-yl)amino] ethanol (V, EXAMPLE 11) and an appropriate α-haloketone (VI), the compounds listed below were prepared:

EXAMPLE 139

6-Phenyl-7-[2-(1-(3,4,5-trimethyl)piperazinyl)ethyl]-2,4-di-1-pyrrolidinyl-7H-pyrrolo[2,3-d]pyrimidine maleate (VII-salt)

mp 89°; NMR of free base (CDCl$_3$) 7.2–7.5, 6.38, 4.27, 3.78, 3.60, 2.70, 2.56, 2.28, 1.8–2.05 and 1.04$\delta$.

EXAMPLE 140

7-[2-(1-(3,5-Dimethyl)piperazinyl)ethyl]-6-phenyl-2,4-di-1-pyrrolidinyl-7H-pyrrolo[2,3-d]pyrimidine maleate (VII-salt)

mp 125°; NMR of free base (CDCl$_3$) 7.2–7.5, 6.37, 4.29, 3.78, 3.60, 3.46, 2.75–2.9, 2.69, 2.57, 1.85–2.05, 1.75 and 1.08$\delta$.

EXAMPLE 141

7-[2-(1-(3,5-Dimethyl)piperazinyl)ethyl]-6-(4-fluorophenyl)-2,4-di-1-pyrrolidinyl-7H-pyrrolo[2,3-d]pyrimidine hydrochloride (VII-salt) mp 179°; NMR of free base (CDCl$_3$) 7.42, 7.09, 6.33, 4.23, 3.78, 3.60, 2.7–2.9, 2.71, 2.56, 1.85–2.1, 1.55–1.8 and 1.05$\delta$.

EXAMPLE 142

6-(4-Fluorophenyl)-7-[2-(1-(3,4,5-trimethyl)piperazinyl)ethyl]-2,4-di-1-pyrrolidinyl-7H-pyrrolo[2,3-d]pyrimidine hydrochloride (VII-salt)

mp 180°; NMR of free base (CDCl$_3$) 7.43, 7.09, 6.33, 4.22, 3.77, 3.60, 2.70, 2.53, 2.05– 2.4, 1.75–2.05, 1.03$\delta$.

EXAMPLE 143

2-[6-(4-Methylphenyl)-2,4-di-1-pyrrolidinyl-7H-pyrrolo[2,3-d]pyrimidin-7-yl]ethanol mp 187°–188°; NMR (CDCl$_3$) 7.87, 7.15–7.35, 6.37, 4.1–4.2, 4.0–4.1, 3.79, 3.58, 2.39, 1.8–2.1$\delta$.

EXAMPLE 144

6-(4-Methylphenyl)-7-[2-(1-(3,4,5-trimethyl)piperazinyl)ethyl]-2,4-di-1-pyrrolidinyl-7H-pyrrolo[2,3-d]pyrimidine hydrochloride (VII-salt)

mp 201°–204°; NMR of free base (CDCl$_3$) 7.35, 7.20, 6.34, 4.25, 3.78, 3.60, 2.71, 2.54, 2.39, 2.0–2.3, 1.7–2.0, 1.03$\delta$.

EXAMPLE 145

6-(4-Methylphenyl)-7-[2-(1-piperazinyl)ethyl]-2,4-di-1-pyrrolidinyl-7H-pyrrolo[2,3-dipyrimidine (VII)

mp 164°; NMR (CDCl$_3$) 7.35, 7.21, 6.34, 4.27, 3.78, 3.59, 2.84, 2.59, 2.45, 2.39, 1.85–2.1$\delta$.

EXAMPLE 146

7-[2-(1-(3,5-Dimethyl)piperazinyl)ethyl]-6-(4-methylphenyl)-2,4-di-1-pyrrolidinyl-7H-pyrrolo[2,3-d]pyrimidine hydrochloride (VII-salt)

mp 238°–240°; NMR of free base (CDCl$_3$) 7.34, 7.20, 6.33, 4.26, 3.78, 3.59, 2.7–2.9, 2.72, 2.58, 2.38, 1.8–2.1, 1.6–1.8, 1.04$\delta$.

EXAMPLE 147

6-(4-Fluorophenyl)-7-[2-(1-piperazinyl)ethyl]-2,4-di-1-pyrrolidinyl-7H-pyrrolo[2,3-d]pyrimidine (VII)

mp 159°–161°; NMR (CDCl$_3$) 7.43, 7.10, 6.34, 4.24, 3.78, 3.59, 2.81, 2.57, 2.40, 1.8–2.1 $\delta$.

EXAMPLE 148

5-Methyl-6-(4-methylphenyl)-7-[2-(1-piperazinyl)ethyl]-2,4-di-1-pyrrolidinyl-7H-pyrrolo[2,3-d]pyrimidine (VII)

mp 126°; NMR of free base (CDCl$_3$) 7.22, 4.09, 3.73, 3.59, 2.81, 2.48, 2.40, 2.3–2.5, 2.20, 1.8–2.2$\delta$.

EXAMPLE 149

7-[2-(1-(3,5-Dimethyl)piperazinyl)ethyl]-5-methyl-6-(4-methylphenyl)-2,4-di-1-pyrrolidinyl-7H-pyrrolo[2,3-d]pyrimidine hydrochloride (VII-salt)

mp 227°–228°; NMR of free base (CDCl$_3$) 7.1–7.3, 4.09, 3.65–3.9, 3.5–3.65, 2.75–2.95, 2.67, 2.48, 2.40, 2.20, 1.8–2.0 and 0.9–1.2$\delta$.

EXAMPLE 150

6-(4-Fluorophenyl)-5-methyl-7-[2-(1-piperazinyl)ethyl]-2,4-di-1-pyrrolidinyl-7H-pyrrolo[2,3-d]pyrimidine (VII)

mp 266°; NMR of free base (CDCl$_3$) 7.05–7.4, 4.07, 3.65–3.8, 3.5–3.65, 2.8–2.95, 2.35–2.55, 2.18 and 1.8–2.0$\delta$.

EXAMPLE 151

7-[2-(1-(3,5-Dimethyl)piperazinyl)ethyl]-6-(4-fluorophenyl)-5-methyl-2,4-di-1-pyrrolidinyl-7H-pyrrolo[2,3-d]pyrimidine hydrochloride (VII-salt)

mp 247°; NMR of free base (CDCl$_3$) 7.2–7.35, 7.13, 4.07, 3.65–3.8, 3.55–3.65, 2.8–3.0, 2.68, 2.46, 2.18, 1.8–2.0, 1.6–1.8 and 1.08$\delta$.

EXAMPLE 152

6-Methyl-2,4-di-1-pyrrolidinyl-7H-pyrrolo[2,3-d]pyrimidine trifluoroacetate (VII)

Following the general procedure outlined in EXAMPLES 18–19 and making noncritical variations but starting with 4-tert-butylamino-2,6-di-(1-pyrrolidinyl)pyrimidine (V, EXAMPLE 17) and 2-chloroacetone (VI) the title compound is obtained, mp 140.5°; NMR (CDCl$_3$) 13.0–13.2, 6.04, 3.7–3.9, 3.62, 2.34 and 1.85–2.2$\delta$.

EXAMPLE 153

6-(4-Methoxyphenyl)-7-methyl-2,4-bis-(4-methylpiperazin-1-yl)-7H-pyrrolo[2,3-d]pyrimidine (VII)

A mixture of 6-(4-methoxyphenyl)-7-methyl-2,4-bis-piperazin-1-yl-7H-pyrrolo[2,3d]pyrimidine (VII, EXAMPLE 121, 789 mg) in dioxane (10 ml) is treated with monosodium salt of phosphorous acid, NaH$_2$PO$_3$, (1M, 19.8 ml) and aqueous formaldehyde (37%, 1.55 ml). The resulting mixture is heated in an inert atmosphere at 60° for 1 hr. The mixture is then poured into aqueous base and the product is isolated by extraction with methylene chloride. Chromatography on silica gel (5% of 4M ammonia-methanol in chloroform), pooling and concentrating the appropriate fractions gives the title compound, NMR (CDCl$_3$; TMS) 7.38, 6.97, 6.29, 3.92, 3.86, 3.64, 2.51, 2.35, 2.34$\delta$.

The free base is converted to the dihydrochloride salt with excess methanolic hydrochloric acid. Recrystallization from methanol/ethyl acetate gives the salt of the title compound, mp 270°–281° (decomp).

EXAMPLE 154

4-[7-Methyl-2,4-bis-(4-methylpiperazin-1-yl)-7H-pyrrolo[2,3-d]pyrimidin-6-yl]-phenol trihydrobromide (VII)

Following the general procedure of EXAMPLE 55 and making non-critical variations, but starting with 6-(4-methoxyphenyl)-7-methyl-2,4-bis-(4-methylpiperazin-1-yl)-7H-pyrrolo[2,3-d]pyrimidine (VII, EXAMPLE 153), the title compound is obtained, NMR (D$_2$O; TSP) 7.26, 6.87, 6.35, 3.58–3.01, 2.91, 2.90$\delta$.

EXAMPLE 155

7-Methyl-2,4-bis-(4-methylpiperazin-1-yl)-6-phenyl-7H-pyrrolo[2,3-d]pyrimidine (VII)

Following the general procedure of EXAMPLE 153 and making non-critical variations but starting with 7-methyl-6-phenyl-2,4-di-1-piperazinyl-7H-pyrrolo[2,3-d]pyrimidine (VII, EXAMPLE 44), the title compound is prepared.

The hydrochloride salt is prepared with excess methanolic hydrochloric acid and triturated with ethyl acetate/hexane (1/1), to give the title compound, NMR (D$_2$O; TSP) 7.36, 6.46, 3.55–2.96, 2.76$\delta$; MS (for free base) calc'd. for C$_{23}$H$_{31}$N$_7$=405.2641, found=405.2642.

EXAMPLE 156

5,6-(Bis-(4-methoxyphenyl)-7-methyl-2,4-bis(4-methylpiperazin-1-yl)-7H-pyrrolo[2,3-d]pyrimidine dihydrochloride (VII)

Following the general procedure of EXAMPLE 153 and making non-critical variations, but starting with 5,6-bis(4.methoxyphenyl)-7-methyl-2,4-di-1-piperazinyl-7H-pyrrolo[2,3d]pyrimidine (VII, EXAMPLE 86), the title compound is obtained, mp 302°–305° (decomp).

EXAMPLE 157

7-Ethyl-6-methyl-2,4-dipyrrolidin-1-yl-7H-pyrrolo[2,3-d]pyrimidine (VII)

Following the general procedure of EXAMPLE 49 and making non-critical variations, but starting with 2,6-di-1-pyrrolidinyl-4-ethylaminopyrimidine (V, EXAMPLE 135), the title compound is obtained.

The corresponding sulfate salt is obtained following the general procedure of EXAMPLE 137, making non-critical variations, mp 227°–228°; NMR (CDCl$_3$, TMS) 6.15, 4.34, 3.77, 2.29, 2.02, 1.34δ; MS calcd for C$_{17}$H$_{25}$N$_6$+H= 300.2188 (free base), found=300.2170.

EXAMPLE 158

7-Ethyl-2,4-dipyrrolidin-1-yl-7H-pyrrolo[2,3-d]pyrimidine (VII)

Following the general procedures of EXAMPLEs 88 and 89 and making non-critical variations, but starting with 2,6-di-1-pyrrolidinyl-4-ethylaminopyrimidine (V, EXAMPLE 135), the title compound is obtained.

The corresponding sulfate salt is obtained following the general procedure of EXAMPLE 137, making non-critical variations, mp 200°–201°; NMR (CDCl$_3$) 6.64, 6.41, 4.40, 3.77, 2.02, 1.45δ; MS (free base) calc'd for C$_{16}$H$_{23}$N$_5$+H= 286.2032, found=286.2038.

EXAMPLE 159

7-Tert-butyl-2,4-di-1-pyrrolidinyl-7H-pyrrolo[2,3-d]pyrimidine (VII)

Following the general procedures of EXAMPLEs 80 and 89 and making non-critical variations, but starting with 4-tert-butylamino-2,6-di-(1-pyrrolidinyl)pyrimidine (V, EXAMPLE 17), the title compound is obtained, mp 187°–190°; MS (free base) calc'd for C$_{14}$H$_{19}$N$_5$=257.1640, found=257.1648.

EXAMPLE 160

5,6,7-Trimethyl-2,4-dipyrrolidin-1-yl-7H-pyrrolo[2,3-d]pyrimidine (VII)

Following the general procedure of EXAMPLE 49, but starting with 3-bromo-2-butanone instead of 2-bromo-propiophenone, the title compound is obtained.

The hydrochloride salt is prepared with excess methanolic hydrochloric acid. Recrystallization from methanol/ethyl acetate mixtures gives the salt of the title compound, mp 234°–2370; NMR (CDCl$_3$; TMS) 4.00–3.74, 3.73, 2.21, 2.19, 1.97δ.

EXAMPLE 161

5,6,7,8-Tetrahydro-2,4-di-1-pyrrolidinyl-1H-pyrimido[4,5-b]indole (VII)

Following the general procedure of EXAMPLE 112 but starting with 4-tert-butylamino-2,6-di-(1-pyrrolidinyl)pyrimidine (V, EXAMPLE 17) instead of the EXAMPLE 3 product, the 9-t-butyl derivative of the title compound is obtained. Removal of the t-butyl group is done according to the procedure of EXAMPLE 19.

Following the general procedure of EXAMPLE 36, the methanesulfonate salt of the title compound is obtained, mp 253°–254°; NMR (CDCl$_3$; TMS) 12.47, 11.99, 3.74, 3.60, 2.89, 2.67, 1.93, 1.78δ; MS (free base) calc'd for C$_{18}$H$_{25}$N$_5$= 311.2110, found=311.2109.

EXAMPLE 162

7-Tert-butyl-6-isopropyl-2,4-di-1-pyrrolidinyl-7H-pyrrolo[2,3-d]pyrimidine, sulfate (VII)

Following the general procedure of EXAMPLEs 49 and 137, but using 1-bromo-3-methyl-2-butanone [VI, Org. Syn. 55, p 24] as the α-bromoketone component (VI), the title compound is obtained, mp 243°–244°, MS (free base) calc'd for C$_{21}$H$_{33}$N$_5$=355.2727, found=355.2736.

EXAMPLE 163

6-Isopropyl-2,4-di-1-pyrrolidinyl-7H-pyrrolo[2,3-d]pyrimidine (VII)

Following the general procedure of EXAMPLE 19, but starting with 7-tert-butyl-6-isopropyl-2,4-di-1-pyrrolidinyl-7H-pyrrolo[2,3-d]pyrimidine (EXAMPLE 162) the title compound is obtained.

Addition of one equivalent of aqueous sulfuric acid (1M), followed by recrystallization from ethyl acetate/methanol mixtures gives the salt of the title compound, mp 223°–225°; MS (low resolution; free base) M$^+$ observed at m/z 299.

EXAMPLE 164

7-Ethyl-6-isopropyl-2,4-di-1-pyrrolidinyl-7H-pyrrolo[2,3-d]pyrimidine, sulfate (VII)

Following the general procedures of EXAMPLEs 49 and 137, but starting with 2,6-di-1-pyrrolidinyl-4-ethylaminopyrimidine (V, EXAMPLE 135) and 1-bromo-3-methyl-2-butanone (VI), the title compound is obtained, mp 208°–210°; MS (low resolution, free base) M$^+$ observed at m/z 327.

EXAMPLE 165

6-Cyclopropyl-7-ethyl-2,4-di-1-pyrrolidinyl-7H-pyrrolo[2,3-d]pyrimidine sulfate (VII)

Following the general procedures of EXAMPLEs 49 and 137, but starting with 2,6-di-1-pyrrolidinyl-4-ethylaminopyrimidine (V, EXAMPLE 135) and bromoacetylcyclopropane (VI), the title compound is obtained, mp 219°–220°; NMR (CDCl$_3$; TMS) 6.01, 4.57–4.50, 3.79–3.77, 2.05–2.01, 1.75–1.70, 1.43, 0.97–0.91, 0.67–0.61δ; MS (free base) calc'd for C$_{19}$H$_{27}$N$_5$+H=326.2345, found=326.2340.

EXAMPLE 166

6-Benzylamino-2,4-di-1-pyrrolidinylpyrimidine (V)

Following the alternative procedure in EXAMPLE 3, but starting with benzylamine instead of methylamine, the title compound is obtained, mp 70°–72°; NMR (CDCl$_3$; TMS) 7.37–7.21, 4.72, 4.43–4.42, 3.53–3.49, 3.37, 1.91–1.87δ.

EXAMPLE 167

6–Cyclopropyl-2,4-di-1-pyrrolidinyl-7H-pyrrolo[2,3-d]pyrimidine (VII)

Following the general procedure of EXAMPLE 49, but starting with 6-benzylamino-2,4-di-1-pyrrolidinylpyrimidine (V, EXAMPLE 166) and bromoacetylcyclopropane (VI), the N-7 benzyl derivative of the title compound is obtained, mp 147°–148°; NMR (CDCl$_3$; TMS) 7.27–7.16, 5.98, 5.41, 3.77–3.73, 3.59–3.55, 1.99–1.88, 1.61–1.52, 0.75–0.69, 0.54–0.49δ.

A mixture of the benzyl derivative (2.64 g) in 125 ml of tetrahydrofuran and 150 ml of liquid ammonia is treated with 850 mg of sodium metal. After 1 hr, solid ammonium chloride is added until the blue color dissipated, the ammonia is removed in a stream of nitrogen, and the product is isolated by extracting the mixture (diluted with water) with chloroform. Concentration gives the title compound, NMR (CDCl$_3$) 8.93, 5.99, 3.77–3.72, 3.61–3.57, 1.96δ1.75, 1.00–0.78, 0.65–0.59δ.

Treatment of the free base with one equivalent of sulfuric acid, followed by recrystallization from methanol/ethyl acetate gives the salt of the title compound, mp 240°–242°; MS (free base) calc'd for C$_{17}$H$_{23}$N$_5$+H=298.2032, found=298.2031.

EXAMPLE 168

5,6,7,8-Tetrahydro-9-[2-(1-piperazinyl)ethyl]-2,4-di-1-pyrrolidinyl-5H-pyrimido[4,5-b]indole maleate (VII)

Following the general procedure of EXAMPLE 112 and making non-critical variations, but starting with 2-[(2,6-di-(1-pyrrolidinyl)pyrimidin-4-yl)amino]ethanol (V, EXAMPLE 11), the N-9 hydroxyethyl intermediate corresponding to the title compound is obtained. Conversion of this intermediate to the title compound is accomplished using the general procedures of EXAMPLEs 13 and 34, making non-critical variations, mp 155°–157°; MS (free base) calc'd for C$_{24}$H$_{37}$N$_7$=423.3110, found=423.3113.

EXAMPLE 169

7-Methyl-6-pyridin-3-yl-2,4-di-1-pyrrolidinyl-7H-pyrrolo[2,3-d]pyrimidine (VII)

Following the general procedure of EXAMPLE 49 and making non-critical variations, but starting with 2-bromo-1-pyridin-3-yl-ethanone (VI) and with 4-methylamino-2,6-di-1pyrrolidinopyrimidine (V, EXAMPLE 3), the title compound is obtained, mp 176°–179°; NMR (CDCl$_3$; TMS) 8.76, 8.52, 7.76, 7.34, 6.49, 3.79, 3.69, 3.62, 1.96δ; MS: calc'd for C$_{20}$H$_{24}$N$_6$=348.2062, found=348.2057.

EXAMPLE 170

6-Phenyl-7-[2-(1-glucosyl)ethyl]-2,4-di-1-pyrrolidinyl-7H-pyrrolo[2,3-d]pyrimidine (VII)

A mixture of 2-[6-phenyl-2,4-di-1-pyrrolidinyl-7H-pyrrolo[2,3-d]pyrimidin-7-yl]ethanol (VII, EXAMPLE 12, 600 mg) in chloroform (20 ml) is cooled to 0° and treated with α-D-glucopyranosyl bromide tetrabenzoate (1.58 g) and silver triflate (614 mg). After 5 minutes at 0° and 3 hours at 25°, the tetrabenzoate product is isolated by chromotography on silica gel eluting with ethyl acetate/chloroform/hexane (20/20/60). The appropriate fractions are pooled and concentrated. The tetrabenzoate is treated with ammonia/methanol (4M, 200 ml, 18 hours, 25°). Concentration followed by chromatography of the residue gives the title compound, (recrystallized from ethyl acetate), mp 197°–199°; MS: calc'd for C$_{28}$H$_{37}$N$_5$O$_6$+H=540.2822, found=540.2837.

EXAMPLE 171

[4-(7-Methyl-2,4-di-1-pyrrolidinyl-7H-pyrrolo[2,3-d]pyrimidin-6-yl)phenoxy]acetic acetic acid methyl ester (VII)

A mixture of 4-(7-methyl-2,4-di-1-pyrrolidinyl-7H-pyrrolo[2,3-d]pyrimidin-6-yl)phenol (VII, EXAMPLE 54, 1.69 g) and methyl bromoacetate (1.3 ml) in DMF (150 ml) is cooled to 0° and treated with sodium hydride (315 mg). After 1 hr at 0° and 16 hrs at 25°, the produce is isolated by pouring the reaction mixture into water and extraction with ethyl acetate. Chromatographic purification eluting with acetone/chloroform (8/92), pooling and concentrating the appropriate fractions followed by recrystallization (ethanol/ethyl acetate) gives the title compound, mp 190°–192°; NMR (CDCl$_3$;TMS) 7.38, 6.95, 6.35, 4.68, 3.83, 3.64, 1.94δ.

EXAMPLE 172

[4-(7-Methyl-2,4-di-1-pyrrolidinyl-7H-pyrrolo[2,3-d]pyrimidin-6-yl)phenoxy]acetic acid, monohydrochloride (VII)

A mixture of [4-(7-methyl-2,4-di-1-pyrrolidinyl-7H-pyrrolo[2,3-d]pyrimidin-6yl)phenoxy]acetic acid methyl ester (EXAMPLE 171, 504 mg) in hydrochloric acid (6M, 45 ml) is heated at reflux for 3 hrs. After cooling the mixture, the title compound is isolated by filtration, mp 186°–191°; NMR (CDCl$_3$; TMS) 7.32, 6.98, 6.38, 4.65, 3.87, 2.03δ.

EXAMPLE 173

N-Hydroxy-N-methyl-4-(7-methyl-2,4-di-1-pyrrolidinyl-7H-pyrrolo[2,3-d]pyrimidin-6-yl)-phenoxyacetamide (VII)

A suspension of [4-(7-methyl-2,4-di-1-pyrrolidinyl-7H-pyrrolo[2,3-d]pyrimidin-6-yl)phenoxy]acetic acid (VII, EXAMPLE 172, 458 mg) in methylene chloride (7 ml) is treated with DMF (85 µl), then cooled to 0° and treated with oxalyl chloride (195 µl). After 20 min at 0°, a mixture of N-methylhydroxylamine hydrochloride (516 mg) and triethylamine (1.1 ml) in THF (6 ml) is added. After 7 hrs at 25° the mixture is concentrated, and the residue is partitioned between methylene chloride and an aqueous pH 4 buffer. Chromatographic purification of the crude product eluting with chloroform/methanol/acetic acid (90/9/1), followed by recrystallization (methylene chloride/hexane) gives the title compound, mp 208°–209°; NMR (CDCl$_3$; TMS) 7.45–7.21, 6.72, 6.29, 4.69, 3.76, 3.63–3.56, 3.18, 1.96δ; MS calc'd for C$_{24}$H$_{30}$N$_6$O$_3$=450.2379, found=450.2376.

EXAMPLE 174

4-(7-Methyl-2,4-di-1-pyrrolidinyl-7H-pyrrolo[2,3-d]pyrimidin-6-yl)phenol sulfate potassium salt (VII)

A suspension of 4-(7-methyl-2,4-di-1-pyrrolidinyl-7H-pyrrolo[2,3-d]pyrimidin-6-yl)phenol (VII, EXAMPLE 54, 517 mg) and dicyclohexylcarbodiimide (3.28 g) in pyridine (9.5 ml) is treated with a mixture of tetrabutylammonium hydrogen sulfate (1.0 g) in pyridine (2.0 ml). The mixture is stirred for 1 hr at 25° and 1 hr at reflux. Addition of methanol (35 ml) and saturated methanolic potassium carbonate (20 ml) led to the separation of a solid. The product is isolated by filtration and purified further by chromatography on C$_{18}$-reversed phase silica gel methanol/water (60/40) to give the title compound, mp 275° (decomp); MS (M+H) observed at 482, M+K observed at 520.

EXAMPLE 175

Diethyl-[2-[4-(7-methyl-2,4-di-1-pyrrolidinyl-7H-pyrrolo[2,3-d]pyrimidin-6-yl)-phenoxy]-ethyl]amine (VII)

A mixture of 4-(7-methyl-2,4-di-1-pyrrolidinyl-7H-pyrrolo[2,3-d]pyrimidin-6-yl)phenol (VII, EXAMPLE 54, 364 mg), aqueous potassium hydroxide (50%, 7 ml), THF (5 ml), tetrabutylammonium bisulfate (170 mg) and 2-diethylaminoethyl chloride hydrochloride (521 mg) is stirred vigorously at 25° for 4.5 hrs and at reflux for 16 hrs. The product free base is then isolated by extraction with chloroform and purification by chromatography eluting with methanol/chloroform (5/95). The appropriate fractions are pooled and concentrated to give the title compound, MS (free base) calc'd for C$_{27}$H$_{38}$N$_6$O+H=463.3185, found=463.3158; NMR (CDCl$_3$; TMS) 7.40, 6.96, 6.37, 4.53, 3.87–3.50, 3.42, 3.21, 1.95, 1.44δ.

EXAMPLE 176

4-(7-Methyl-2,4-di-1-pyrrolidinyl-7H-pyrrolo[2,3-d]pyrimidin-6-yl)phenol N,N-dimethylsulfamoyl derivative (VII)

A mixture of 4-(7-methyl-2,4-di-1-pyrrolidinyl-7H-pyrrolo[2,3-d]pyrimidin-6-yl)phenol (VII, EXAMPLE 54, 325 mg), 144 mg of N,N-dimethylsulfamoyl chloride, 32 µl of 7N aqueous sodium hydroxide, and 3 mg of tetrabutylammonium bromide in 4 ml of benzene is stirred at 25° for 5 min, then heated at reflux for 2 hrs. After cooling, the mixture is partitioned between benzene and water (pH 8–9), and the organic phase is evaporated. Recrystallization of the residual solid from acetone/hexane gives the title compound, mp 186°–188°; NMR (CDCl$_3$; TMS): 7.47, 7.32, 6.42, 3.79, 3.64, 3.01, 1.95δ.

EXAMPLE 177

4-(7-Methyl-2,4-di-1-pyrrolidinyl-7H-pyrrolo[2,3-d]pyrimidin-6-yl)phenol 2-{2-[2-(2-methoxy)ethoxy]ethoxy}ethyl ether (VII)

A mixture of sodium hydride dispersion (60%, 1.06) and 4-(7-methyl-2,4-di-1-pyrrolidinyl-7H-pyrrolo[2,3-d]pyrimidin-6-yl)phenol (VII, EXAMPLE 54, 910 mg) in DMF (5 ml) is stirred at 25° for 45 min and 60° for 15 min. The mixture is cooled to 25° and treated with a mixture of triethyleneglycol monomethyl ether monotoluenesulfonate (1.01 g) in DMF (3 ml). The resulting mixture is stirred for 1 hr at 25° and 3 hrs at 60°. After cooling, most of the DMF is removed, and the product is isolated by extraction with ethyl acetate/water. The organic layer is dried and concentrated. Chromatographic purification on silica eluting with acetone/chloroform (10/90), followed by recrystallization (ethyl acetate/hexane) gives the title compound, mp 88°–89°.

EXAMPLE 178

4-(7-Methyl-2,4-di-1-pyrrolidinyl-7H-pyrrolo[2,3-d]pyrimidin-6-yl)phenol 1-(2-imidazol-1-yl)ethyl ether (VII)

A vigorously stirred mixture of 4-(7-methyl-2,4-di-1-pyrrolidinyl-7H-pyrrolo[2,3-d]pyrimidin-6-yl)phenol (VII, EXAMPLE 54, 3.17 g), 1,2-dibromoethane (26.3 g), aqueous sodium hydroxide (50%, 20 g) and tetrabutylammonium bisulfate (100 mg) in THF (25 ml) is heated at 50° for 1.5 hrs. Cooling and extraction of the reaction mixture with methylene chloride gives the 2-bromo-1-ethyl ether of the EXAMPLE 54 product. A mixture of 330 mg of this intermediate bromoethyl ether, 960 mg of imidazole, and 50 mg of sodium iodide in 10 ml of toluene is heated at reflux for 48 hrs. Extraction of the cooled reaction mixture with methylene chloride/water and concentration gives the title compound, MS (free base) calc'd for $C_{26}H_{31}N_7O$= 457.2590, found=457.2597.

Treatment of this material with one equivalent of methanolic hydrochloric acid gives the salt of the title compound, mp 132–140.

EXAMPLE 179

4-(7-Methyl-2,4-di-1-pyrrolidinyl-7H-pyrrolo[2,3-d]pyrimidin-6-yl)phenyl-N,N-dimethyl carbamate (VII)

A mixture of sodium hydride (60%, 1.13 g) in anhydrous dimethylformamide (40 ml) is cooled in an ice bath and treated with 4.(7-methyl-2,4-di-1-pyrrolidinyl-7H-pyrrolo[2,3-d]pyrimidin-6-yl)phenol (VII, EXAMPLE 54, 2.00 g). After 2 hrs at 25° and 20 min at 60°, the mixture is cooled to 25° and treated with 1.27 ml of dimethylcarbamyl chloride. After 3.5 hrs at 25°, the product is isolated by extraction with ethyl acetate. Chromatography on silica eluting with methanol/chloroform (2/98) followed by recrystallization of the product from ethyl acetate gives the title compound, mp 194°–195°; NMR 7.45–7.43, 7.17–7.14, 6.39, 3.90–3.71, 3.67, 3.55–3.21, 3.12, 3.03, 2.04–1.92δ; MS calc'd for $C_{24}H_{30}N_6O_2$=434.2430, found=434.2440.

EXAMPLES 180–182

Following the general procedure of EXAMPLE 49 and making non-critical variations, but starting in each case with 4-methylamino-2,6-di-1-pyrrolidinopyrimidine (V, EXAMPLE 3) and the appropriate α-bromoketone (VI), the title compounds of EXAMPLEs 180–182 were synthesized:

EXAMPLE 180

4-(7-Methyl-2,4-bis-pyrrolidin-1-yl-7H-pyrrolo[2,3-d]pyrimidin-6-yl)benzoic acid ethyl ester (VII)

mp 195°–200°; NMR 8.08–8.05, 7.55–7.52, 6.54, 4.43–4.36, 3.91–3.75, 3.72, 3.69–3.52, 2.00–1.92, 1.43–1.39δ.

EXAMPLE 181

6-(4-Bromophenyl)-7-methyl-2,4-di-1-pyrrolidinyl-7H-pyrrolo[2,3-d]pyrimidine (VII) and the methanesulfonate salt Free base: mp 238°–239°; NMR 7.55–7.48, 7.36–7.31, 6.42, 3.75–3.82, 3.66, 3.66–3.58, 2.02–1.90.

Methanesulfonate salt, mp 244°–246°.

EXAMPLE 182

4-(7-Methyl-2,4-bis-pyrrolidin-1-yl-7H-pyrrolo[2,3-d]pyrimidin-6-yl)benzonitrile (VII)

mp 265°–266°; NMR 7.68–7.63, 7.58–7.52, 6.55, 3.83–3.75, 3.72, 3.66–3.58, 2.06–1.90δ.

EXAMPLE 183

7-Methyl-2,4-bispyrrolidin-1-yl-6-[4-(1H-tetrazol-5-yl)-phenyl]-7H-pyrrolo[2,3-d]pyrimidine (VII)

A mixture of 4-(7-methyl-2,4-bis-pyrrolidin-1-yl-7H-pyrrolo[2,3-d]pyrimidin-6-yl)benzonitrile (EXAMPLE 182, 219 mg), 166 mg of triethylamine hydrochloride and 153 mg of sodium azide in 9 ml of N-methylpyrrolidine is heated at 150° for 4 hrs and then stirred at 20°–25° overnight. The mixture is distilled (0.9 mm Hg, 50°) to remove the solvent. The resulting solid is dissolved in 150 ml of saline and 200 ml of chloroform. The phases are separated and the aqueous extracted with 5 portions of chloroform. The combined organic extracts are dried over sodium sulfate and concentrated. The concentrate is chromatographed over silica gel, eluting with 15–20% methanol saturated with ammonia-dichloromethane. The appropriate fractions are pooled and concentrated to give the title compound, mp 289°–291°; NMR 7.96–7.93, 7.64–7.61, 6.56, 3.70–3.45, 3.45–3.23, 1.92–1.62δ; MS calc'd for $C_{22}H_{25}N_9$+H=416.2311, found=416.2322.

EXAMPLE 184

4-(7-Methyl-2,4-bis-pyrrolidin-1-yl-7H-pyrrolo(2,3-d)pyrimidine-6-yl)benzamide (VII)

A suspended mixture of 6-(4-bromophenyl)-7-methyl-2,4-di-1-pyrrolidinyl-7H-pyrrolo[2,3-d]pyrimidine (EXAMPLE 181, 205 mg), in 4.0 ml of anhydrous tetrahydrofuran is cooled in a dry ice-acetone bath and treated with 0.55 ml of a 1.38M mixture of t-butyllithium in pentane followed by 0.12 ml of trimethylsilyl isocyanate. The mixture is stirred for 10 min, warmed to 20°–25° and then stirred for 30 min. The mixture is poured onto water, diluted with saline and extracted with ethyl acetate. The combined organic extracts are dried and concentrated to give a solid which is chromatographed over silica gel (elution with 3% methanol saturated with ammonia-dichloromethane) to give the title compound, mp 175°–180°.

Treatment of the free base with excess hydrochloric acid gives the salt of the title compound, mp 275°–278°; NMR 8.03, 7.92–7.89, 7.60–7.58, 7.38, 6.83, 3.72–3.34, 2.10–1.80; MS calc'd for $C_{22}H_{26}N_6O$=390.2168, found=390.2172.

EXAMPLE 185

4-(7-Methyl-2,4-bis-pyrrolidin-1-yl-7H-pyrrolo[2,3-d]pyrimidin-6-yl)benzoic acid (VII)

A suspension of 4-(7-methyl-2,4-bis-pyrrolidin-1-yl-7H-pyrrolo[2,3-d]pyrimidin-6-yl)benzoic acid ethyl ester (EXAMPLE 180, 2.04 g) in ethanol (95%, 80 ml) is treated with 240 ml of a 0.1N aqueous mixture of potassium hydroxide. The mixture is heated at reflux for two days and then partially concentrated under reduced pressure. The resulting mixture is poured onto 300 ml of 5% aqueous hydrochloric acid and extracted with 5 portions of chloroform. The combined organics are dried and concentrated, the concentrate is chromatographed over silica gel, eluting with methanol/chloroform/acetic acid (5/94/1) to give the title compound, mp 290°–295°.

A suspension of 150 mg of the above free acid in 4 ml of tetrahydrofuran is treated with 3.8 ml of a 0.1N mixture of potassium hydroxide followed by 1 ml of methanol. The mixture is heated for 1 hr at 50° and then an additional 3.8 ml (0.38 mmol) of 0.1N mixture of potassium hydroxide is added. The mixture is concentrated under reduced pressure and then chromatographed over reverse phase silica gel eluting with methanol/water (75/25). The appropriate fractions are pooled and concentrated. The concentrate is taken up in water and lyophilized to give the potassium salt of the title compound, mp >320°; NMR (DMSO) 7.95–7.92, 7.54–7.51, 6.61, 4.20–3.44, 2.10–1.82δ; MS calc'd for $C_{22}H_{24}N_5O_2K$=430.1645, found=430.1668.

EXAMPLE 186

2-[4-(7-Methyl-2,4-bis-pyrrolidin-1-yl-7H-pyrrolo[2,3-d]pyrimidin-6-yl)benzoylamino]ethanesulfonic acid ammonium salt (VII)

A suspension of 4-(7-methyl-2,4-bis-pyrrolidin-1-yl-7H-pyrrolo[2,3-d]pyrimidin-6-yl)benzoic acid (EXAMPLE 185, 253 mg) in 5 ml of DMF is treated with 83 mg of N-hydroxysuccinimide, 0.11 ml of diisopropylcarbodiimide and 10 mg of dimethylaminopyridine. After 18 hrs at 20°–25° filtration gives 300 mg of an intermediate N-hydroxysuccinimide ester.

A suspension of 249 mg of this intermediate N-hydroxysuccinimide ester in 50 ml of THF is warmed slightly until the solid goes into mixture and then treated with 662 mg of taurine in 5.2 ml of 1.0N aqueous sodium hydroxide followed by 5 ml of water. The mixture is stirred for 2 hrs and then concentrated under reduced pressure. The resulting residue is dissolved in water and treated with 5% aqueous hydrochloric acid. The pH of the mixture is adjusted to pH 4. The layers were separated and finally the aqueous layer is extracted with chloroform. The combined organics are dried and concentrated to give 621 mg of a solid which is chromatographed over silica gel (elution with 15–20% methanol saturated with ammonia-dichloromethane) to give the title compound, mp 185°–190°; NMR (DMSO) 8.63–8.51, 7.86–7.84, 7.68–7.65, 7.36, 7.19, 7.02, 6.74, 3.88–3.26, 2.79–2.64, 2.13–1.80δ; MS calc'd for $C_{24}H_{30}N_6O_4S$+H=499.2127, found: 499.2143.

EXAMPLE 187

4-(7-Methyl-2,4-bis-pyrrolidin-1-yl-7H-pyrrolo[2,3-d]pyrimidin-6-yl)-N-(1H-tetrazol-5-yl)-benzamide (VII)

A mixture of 247 mg of the N-hydroxysuccinimide ester from EXAMPLE 186 in 50 ml of dimethylformamide is treated with 110 mg of 5-aminotetrazole followed by 71 mg of dimethylaminopyridine. The mixture is stirred for 3 hrs and then heated at reflux for 1 hr. The dimethylformamide is removed at reduced pressure to give a solid which is dissolved in chloroform with the aid of a small amount of methanol. The resulting mixture is washed with saline. The aqueous layer is extracted with six portions of chloroform. The combined organics are dried and filtered. The solids are washed with dimethylformamide. The filtrate is concentrated to give an orange solid which is chromatographed over silica gel (elution with 15–20% methanol saturated with ammonia-dichloromethane) to give the title compound, mp >310°; NMR (DMSO) 8.15–8.12, 7.76–7.73, 7.24, 6.77, 3.89–3.60, 3.60–3.46, 2.07–1.80δ; MS calc'd for $C_{23}H_{26}N_{10}O$=459.2369, found=459.2374.

EXAMPLE 188

4- (7-Methyl-2,4-di-1-pyrrolidinyl-7H-pyrrolo-[2,3-d]pyrimidin-6-yl)phenylamine (VII)

Following the general procedure of EXAMPLE 49 and making non-critical variations, but utilizing 4-benzyloxycarbonylamino phenacyl bromide (VI), the benzyloxycarbonyl derivative of the title compound is obtained. A mixture of 253 mg of this derivative and 67.8 mg of 10% palladium on carbon in 5 ml of dimethylformamide is hydrogenated at 50 psi for 2 hrs. The mixture is filtered through a pad of celite and washed thoroughly with dimethylformamide, methanol, chloroform and dichloromethane. The filtrate is partially concentrated, poured onto water and extracted with three portions of ethyl acetate/hexane (1/1). The combined organic extracts are dried and concentrated to give a solid which is chromatographed over silica gel eluting with methanol/chloroform (3/97). The appropriate fractions are pooled and concentrated to give the title compound, mp 235°–237°; NMR 7.26–7.24, 6.74–6.70, 6.31, 3.90–3.50, 1.88–2.07δ; MS calc'd for $C_{21}H_{26}N_6$=362.2219, found=362.2213.

The free base is converted to the dihydrochloride salt with excess methanolic hydrochloric acid. Recrystallization from methanol/ethyl acetate gives the salt of the title compound, mp 205°–207°; NMR 7.51–7.49, 7.31–7.29, 6.42, 4.28–3.35, 2.28–1.80δ; MS calc'd for $C_{21}H_{26}N_6$=362.2219, found=362.2223.

EXAMPLE 189

N-[4-(7-Methyl-2,4-bis-pyrrolidin-1-yl-7H-pyrrolo[2,3-d]pyrimidin-6-yl)phenyl]methanesulfonamide (VII)

A mixture of 4-(7-methyl-2,4-di-1-pyrrolidinyl-7H-pyrrolo-[2,3-d]pyrimidin-6yl)phenylamine (EXAMPLE 188, 103 mg), in 30 ml of pyridine is cooled in an ice-water bath and treated with 24 µl of methanesulfonyl chloride. The mixture is warmed to 20°–25° and stirred for 2 days. An additional 24 µl of methanesulfonyl chloride is added and the mixture stirred for an additional 3 hrs. The mixture is poured onto water and extracted with three portions of dichloromethane. The combined organics are dried and concentrated to give a solid which is chromatographed over silica gel, eluting with methanol/chloroform (4/96) to give the desired material which is recrystallized from hot acetonitrile give the title compound, mp 248°–250°; NMR 7.46–7.43, 7.27–7.24, 6.72, 6.40, 3.88, 3.67, 3.67–3.55, 3.05, 2.01–1.92δ.

EXAMPLE 190

4-(7-Methyl-2,4-di-1-pyrrolidinyl-7H-pyrrolo[2,3-d]pyrimidin-6-yl)phenylamine bis(methanesulfonamide) (VII)

A mixture of 4-(7-methyl-2,4-di-1-pyrrolidinyl-7H-pyrrolo-[2,3-d]pyrimidin-6-yl)phenylamine (EXAMPLE 188, 206 mg) in 40 ml of dichloromethane is cooled in an ice-water bath and treated with 0.15 ml of triethylamine followed by 0.05 ml of methanesulfonyl chloride. Three additional portions of methanesulfonyl chloride, 0.02 ml, 0.01 ml and 0.01 ml, are added in sequence over the next hour. The mixture is poured onto water, treated with aqueous saturated sodium bicarbonate and extracted with three portions of dichloromethane. The combined organic extracts are dried and concentrated to give a solid which is combined with previously isolated material (from a 50 mg run) and chromatographed over silica eluting with methanol/chloroform (3/97) to give the desired material which is recrystallized from hot acetonitrile to give the title compound, mp 245–248; NMR 7.49–7.47, 7.31–7.28, 6.42, 3.78–3.69, 3.64, 3.58–3.52, 3.36, 1.97–1.85δ.

EXAMPLE 191

[4-(7-Methyl-2,4-bis-pyrrolidin-1-yl-7H-pyrrolo[2,3-d]pyrimidin-6-yl)phenyl]guanidine (VII)

A mixture of 4-(7-methyl-2,4-di-1-pyrrolidinyl-7H-pyrrolo-[2,3-d]pyrimidin-6-yl)phenylamine (EXAMPLE 188, 247 mg) in 50 ml of dichloromethane is treated with 245 mg of di-2-pyridyl thioncarbonate. The mixture is stirred 1 hr, poured onto water and extracted with three portions of dichloromethane. The combined organic extracts are dried and concentrated to give a solid which is dissolved in 50 ml of dichloromethane. Ammonia is then bubbled into the mixture for about 5 min. The mixture is allowed to stand for 1 day and then placed in the freezer and allowed to stand for 2 days. The mixture is faltered to give a thiourea intermediate corresponding to the starting amine, mp 220°–225°; NMR 9.73, 7.43, 6.44, 3.73–3.59, 3.54, 3.50–3.39, 1.93–1.75δ; MS M+obvserved at 421.

A suspension of 1.01 g of the thiourea intermediate from above in 200 ml of acetonitrile is warmed to 400 and treated with 0.16 ml of methyl iodide. The mixture is stirred for 2 hrs and then the temperature is increased to 50°. The mixture is stirred overnight. The temperature is increased to 70° and an additional 0.08 ml of methyl iodide is added. The mixture is stirred 1.5 hrs and treated with 0.04 ml of methyl iodide. Finally after stirring 2 hrs, 0.02 ml (0.32 mmol) of methyl iodide is added. The mixture is stirred 1 hr, cooled and faltered to give 183 mg of unreacted starting material. The filtrate is concentrated and chromatographed over silica gel, eluting with methanol/chloroform (5/95) to give the desired material which still contained some impurity. The material is rechromatographed over silica gel eluting with methanol/chloroform (2/98) to give the corresponding methyl isothiourea, mp 95°–98°, NMR 7.43–7.40, 6.99–6.97, 6.39, 3.81–3.77, 3.67, 3.65–3.60, 1.98–1.92δ.

A mixture of 313 mg of the above isothiourea in 32 ml of t-butanol is treated with ammonia for 25 min. The mixture is heated in a sealed tube at reflux overnight. The mixture is then treated with ammonia a second time for 15 min and heated at reflux for an additional 7 hrs. Ammonia is bubbled in for a third time for 10 min and then heated at reflux for 24 hrs. The mixture is concentrated under reduced pressure, diluted with chloroform and water. The mixture is treated with aqueous sodium hydroxide (5%) until the pH is approximately 11. The layers were separated and the aqueous is back-extracted with two portions of chloroform. The combined organics are dried and concentrated to give a solid which is chromatographed over silica gel (elution with 30% methanol saturated with ammonia/dichloromethane) to give the title compound, NMR (DMSO) 7.27–7.25, 6.81–6.79, 6.27, 3.72–3.51, 3.46, 3.43–3.29, 1.90–1.67δ; MS calc'd for $C_{22}H_{28}N_8$+H=405.2515, found=405.2511.

EXAMPLE 192

5,6,7,8-Tetrahydro-9-(2-hydroxyethyl)-2,4-di-1-pyrrolidinyl-5H-pyrimido[4,5-b]indole (VII)

Following the general procedure of EXAMPLE 112, and making non-critical variations, but starting with the EXAMPLE 11 product and 2-bromocyclohexanone, the title compound is obtained, NMR (CDCl$_3$; TMS) 7.64, 4.05, 3.91, 3.67, 3.55, 2.72, 2.56, 1.70–2.0δ; HRMS: calcd. for $C_{20}H_{29}N_5O$=355.2372, found 355.2368.

EXAMPLE 193

5,6,7,8-Tetrahydro-9-[2-(1-piperidinyl)ethyl]-2,4-di-1-pyrrolidinyl-5H-pyrimido[4,5-b]indole dihydrochloride (VII)

Following the general procedures of EXAMPLEs 13 and 34, but starting with 5,6,7,8-tetrahydro-9-(2-hydroxyethyl)-2,4-di-1-pyrrolidinyl-5H-pyrimido[4,5-b]indole, (VII, EXAMPLE 192) and using piperidine in the second step (in place of piperazine), the free base of the title compound is prepared. Addition of excess anhydrous hydrochloric acid to an ether solution of the free base, followed by filtration and recrystallization from acetone/ether mixtures, gives the title compound, mp 178°–180°; HRMS (FAB): Calcd. for $C_{25}H_{38}N_6$+H=423.3236, found 423.3240.

EXAMPLE 194

5,6,7,8-Tetrahydro-9-[2-(4-morpholinyl)ethyl]-2,4-di-1-pyrrolidinyl-5H-pyrrimido[4,5-b]indole dihydrochloride (VII)

Following the general procedures of EXAMPLEs 13 and 34, but starting with 5,6,7,8-tetrahydro-9-(2-hydroxyethyl)-2,4-di-1-pyrrolidinyl-5H-pyrimido[4,5-b]indole, (VII, EXAMPLE 192), the free base of the title compound is obtained, mp 132°–133°. Treatment of an ether solution of the free base with excess anhydrous hydrochloric acid, followed by recrystallization from acetone gives the title compound, mp 205°–2080; low resolution MS-ions observed at 424 (M+), 311, 312, 283, 100.

EXAMPLE 195

2,6-Di-1-pyrrolidinyl-4-[2-(4-morpholinyl)ethylamino]-pyrimidine (V)

A solution of 4-chloro-2,6-di-1-pyrrolidinylpyrimidine (30 g) and 4-(2-aminoethyl)morpholine (100 g) is heated at 155° for 20 hours. The mixture is then cooled to 25°, diluted with water and extracted with ethyl acetate/hexane (1/1). The combined organic phases are washed with a saturated aqueous sodium chloride solution, dried and concentrated. Crystallization of the residue from hexane gives the title compound, mp 86°–89°; MS 346 (M+), 246, 234, 233, 205 and 100.

EXAMPLE 196

Improved preparation of EXAMPLE 194 product (VII)

A mixture of 2,6-di-1-pyrrolidinyl-4-[2-(4-morpholinyl)ethylamino]-pyrimidine (V, EXAMPLE 195, 30 g), N,N-diisopropylethylamine (19.2 ml) and 2-bromocyclohexanone (18.4 g) in acetonitrile (330 ml) is heated at reflux for 5 days. The reaction mixture is cooled to 0° and the free base of the title compound is isolated by filtration. Conversion to the dihydrochloride as in EXAMPLE 194 gives the title compound, mp 205°–208°.

EXAMPLE 197

6-(4-Fluorophenyl)-7-(2-hydroxyethyl)-2,4-di-1-pyrrolidinyl-7H-pyrrolo[2,3-d]pyrimidine (VII)

Following the general procedure of EXAMPLE 12 and making non-critical variations, but starting with 4-fluorophenacyl bromide instead of 2-bromoacetophenone, the title compound is obtained, mp 180°–182°; NMR (CDCl$_3$; TMS) 7.82, 7.30, 7.10, 6.36, 4.11, 4.01, 3.78, 3.58 and 1.96δ; MS (m/z) 395 (M+), 364, 351 and 197.

EXAMPLE 198

6-(4-Fluorophenyl)-7-[2-(1-imidazolyl)ethyl]-2,4-di-1-pyrrolidinyl-7H-pyrrolo[2,3-d]pyrimidine sulfate (VII)

Following the general procedures of EXAMPLES 13 and 34, and making non-critical variations, but starting with 6-(4-fluorophenyl)-7-(2-hydroxyethyl)-2,4-di-1-pyrrolidinyl-7H-pyrrolo[2,3-d]pyrimidine (VII, EXAMPLE 197) and using imidazole in the second step instead of piperazine, the free base of the title compound is obtained. Addition of a molar equivalent of aqueous sulfuric acid to a methanol solution of the free base, followed by recrystallization gives the title compound, mp 153°–155°; NMR (CDCl$_3$; TMS) 7.08, 6.42, 6.33, 4.61, 4.46, 3.78, 3.64 and 1.96δ; MS (m/z) 445 (M+), 351, 323 and 222.

EXAMPLE 199

6-(4-Fluorophenyl)-7-[2-(4-morpholinyl)ethyl]-2,4-di-1-pyrrolidinyl-7H-pyrrolo[2,3-d]pyrimidine sulfate (VII)

Following the general procedures of EXAMPLES 13 and 34, and making non-critical changes, but starting with 6-(4-fluorophenyl)-7-(2-hydroxyethyl)-2,4-di-1-pyrrolidinyl-7H-pyrrolo[2,3-d]pyrimidine (VII, EXAMPLE 197) and utilizing morpholine instead of piperazine in the second step, the free base of the title compound is obtained. Conversion to the sulfuric acid salt, followed by recrystallization, gives the title compound, mp 250° (decomp); NMR (CDCl$_3$; TMS) 7.45–7.36, 7.28–7.14, 6.42, 4.97, 4.90–4.80, 3.91–3.70, 2.88–2.76, 2.76–2.61 2.15–1.94δ; IR 2953, 2924, 1573, 1449, 1227 and 1162 cm$^{-1}$.

EXAMPLE 200

6-(4-Fluorophenyl)-7-[2-(1-tetrazolyl)ethyl]-2,4-di-1-pyrrolidinyl-7-H-pyrrolo[2,3-d]pyrimidine (VII)

Following the general procedures of EXAMPLES 13 and 34, and making non-critical variations, but starting with 6-(4-fluorophenyl)-7-(2-hydroxyethyl)-2,4-di-1-pyrrolidinyl-7H-pyrrolo[2,3-d]pyrimidine (VII, EXAMPLE 197) and utilizing tetrazole in place of piperazine in the second step, the title compound is obtained, mp 165°–166°; NMR (CDCl$_3$; TMS) 8.29, 7.08, 6.29, 5.00, 4.67, 3.76, 3.60 and 1.95δ; MS (m/z) 447 (M+), 419, 364, 297, 271 and 188.

EXAMPLE 201

6-(4-Fluorophenyl)-7-[2-(1-(4-[4-fluorophenyl]piperazinyl)-ethyl)]-2,4-di-1-pyrrolidinyl-7H-pyrrolo[2,3-d]pyrimidine sulfate (VII)

Following the general procedures of EXAMPLES 13 and 34, and making non-critical changes, but starting with 6-(4-fluorophenyl)-7-(2-hydroxyethyl)-2,4-di-1-pyrrolidinyl-7H-pyrrolo[2,3-d]pyrimidine (VII, EXAMPLE 197) and utilizing 1-(4-fluorophenyl)piperazine in the second step, the free base of the title compound is obtained. Conversion to the sulfate salt (analogous to EXAMPLE 198) and recrystallization gives the title compound, mp 172°–174°; NMR (CDCl$_3$; TMS) 7.53, 7.26, 6.81, 6.72, 6.39, 5.13, 3.80, 3.30, 3.08, 2.16, 1.96δ.

EXAMPLE 202

6-(4-Fluorophenyl)-5-methyl-7-[2-(1-morpholinyl)ethyl]-2,4-di-1-pyrrolidinyl-7H-pyrrolo[2,3-d]pyrimidine (VII) hydrochloride (VII-salt)

Following the general procedure of EXAMPLEs 12–13, 25–27, and 30–34 and making non-critical variations but using 2-[(2,6-di-(1-pyrrolidinyl)pyrimidin-4-yl)amino]ethanol (V, EXAMPLE 11) and the appropriate α-haloketone (VI), the title compound is obtained, mp 147°–149°; NMR of free base (CDCl$_3$) 7.2–7.4, 7.13, 4.07, 3.5–3.8, 2.47, 2.3–2.45, 2.18 and 1.8–2.05 δ.

CHART A
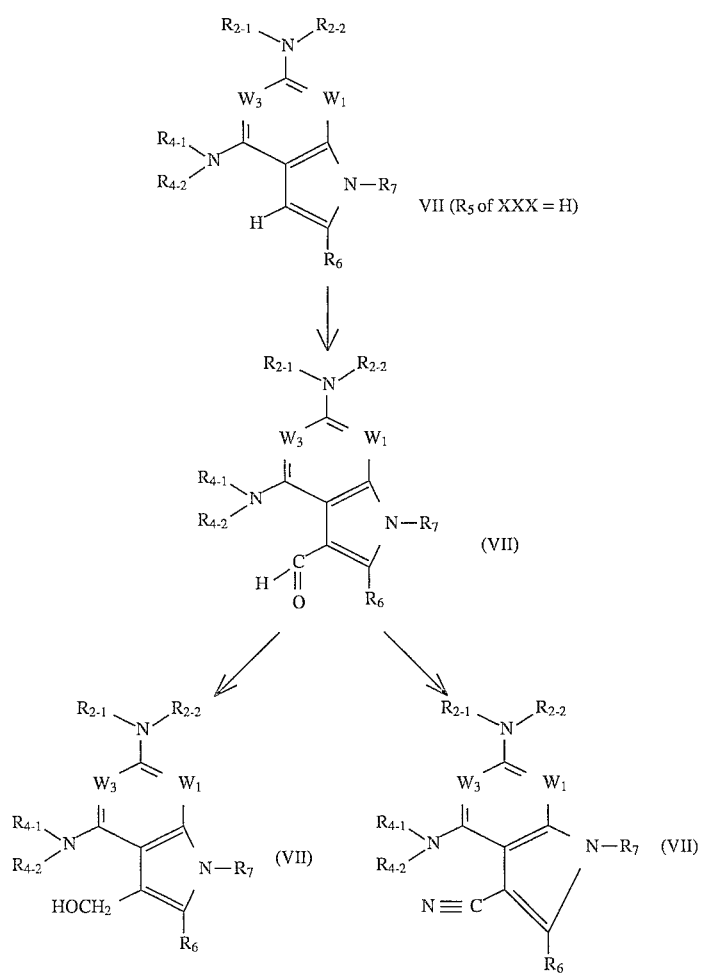
CHART B
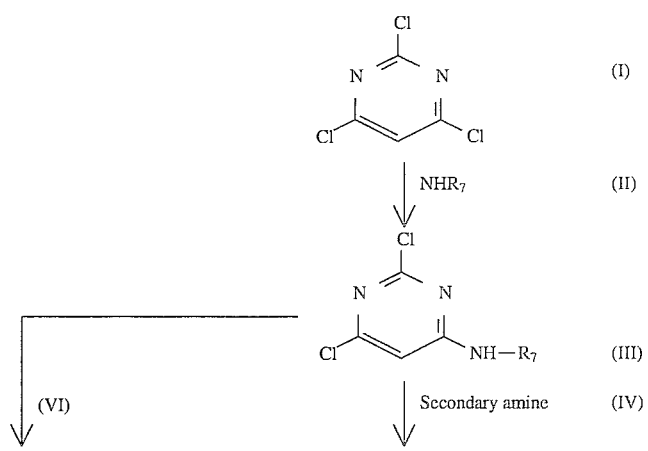

-continued
CHART B
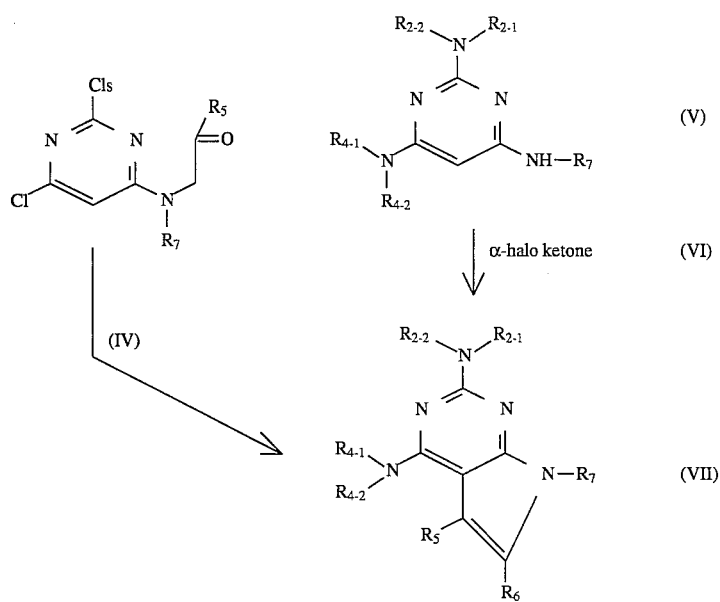
CHART C
(IX) ↓ See Chart D
(X)
↓
(XXIII)
↓
(XXIV)
↓
-continued
CHART C
(XXV)
CHART D
(VIII)
↓
(VIIIA)
↓

-continued
CHART D
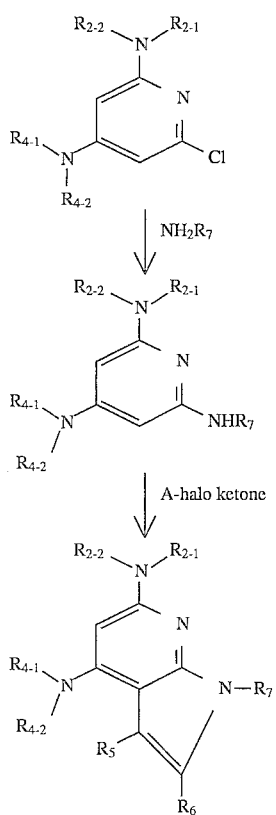
CHART E
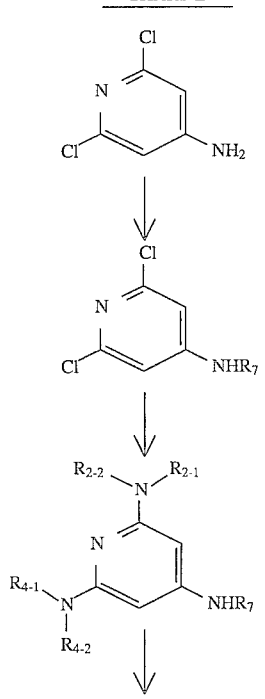
-continued
CHART E
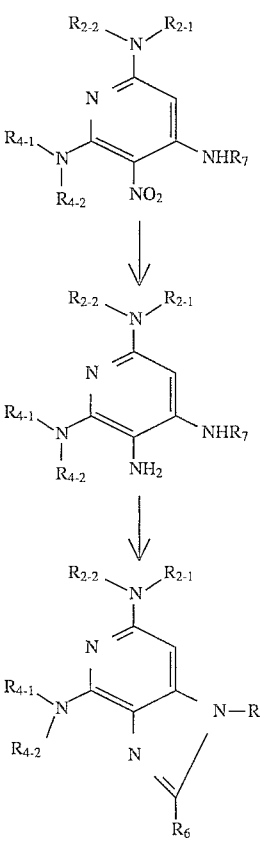
CHART F
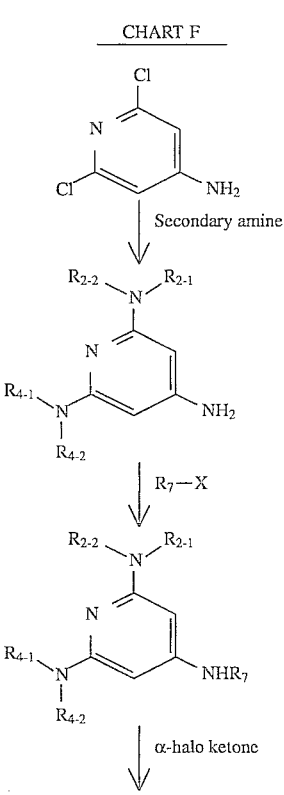

85
-continued
CHART F

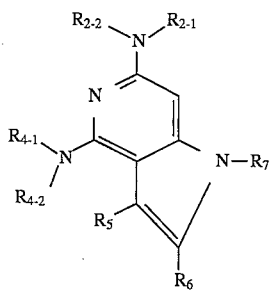
(XVI)

CHART G

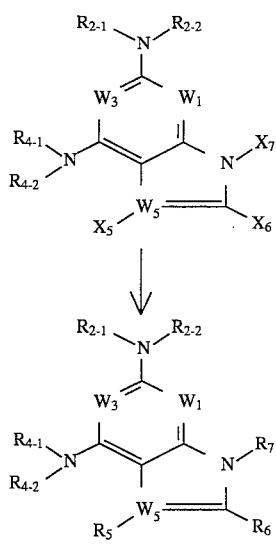

CHART H

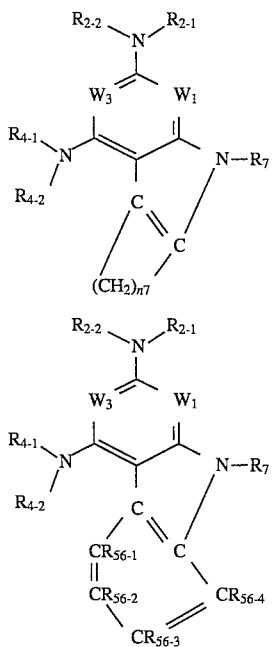
(R$_6$-2A)

(R$_6$-2B)

We claim:
1. A bicyclic heterocyclic amines of the formula (XXX)

86

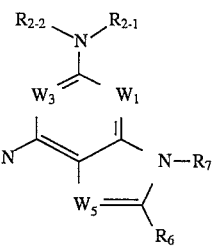
(XXX)

where
$W_1$ is —N= or —CH=;
$W_3$ is —N= or —CH=;
$W_5$ is —N= or —CR$_5$— with the proviso that $W_5$ is —CR$_5$— when both $W_1$ and $W_3$ are —N=;
where
$R_5$ is
($C_5$-1)
  (A) —H,
($C_5$-2)
  (B) $C_1$–$C_8$ alkyl optionally substituted with 1 thru 4 $R_{5-1}$ where $R_{5-1}$ is
    (1) —F, —Cl, —Br,
    (2) $C_1$–$C_4$ alkyl,
    (3) —CF$_3$,
    (4) -φ,
    (5) —OR$_{5-2}$ where $R_{5-2}$ is
      (a) —H,
      (b) $C_1$–$C_4$ alkyl,
      (c) phosphate,
      (d) sulfate,
      (e) —CO—R$_{5-8}$ where R$_{5-8}$ is $C_1$–$C_4$ alkyl or $C_6$–$C_9$ aralkyl,
      (f) —CO—NR$_{5-10}$R$_{5-11}$ where R$_{5-10}$ and R$_{5-11}$ are the same or different and are —H or $C_1$–$C_3$ alkyl,
      (g) sulfamate,
      (h) glucosyl,
      (i) galactosyl,
      (j) glucuronic acid,
      (k) maltosyl,
      (l) arabinosyl,
      (m) xylosyl,
      (n) —CO—CH(NH$_2$)—H,
      (o) —CO—CH(NH$_2$)—CH$_3$,
      (p) —CO—CH(NH$_2$)—CH(CH$_3$)$_2$,
      (q) —CO—CH(NH$_2$)—CH$_2$—CH(CH$_3$)$_2$,
      (r) —CO—CH(NH$_2$)—CH(CH$_3$)—CH$_2$—CH$_3$,
      (s) —CO—CH(NH$_2$)—CH$_2$—OH,
      (t) —CO—CH(NH$_2$)—CH(OH)—CH$_3$,
      (u) —CO—CH(NH$_2$)—CH$_2$-φ,
      (v) —CO—CH(NH$_2$)—CH$_2$-[p-phenyl]—OH,
      (w) —CO—CH(NH$_2$)—CH$_2$-[2-indolyl]
      (x) —CO—CH(NH$_2$)—CH$_2$—SH,
      (y) —CO—CH(NH$_2$)—CH$_2$—CH$_2$—S—CH$_3$,
      (z) —CO—C*H—NH—CH$_2$—CH$_2$—C*H$_2$ where the carbon atoms marked with an "*" are bonded together to form a heterocyclic ring,
      (aa) —CO—C*H—NH—CH$_2$—CH(OH)—C*H$_2$ where the carbon atoms marked with an "*" are bonded together to form a heterocyclic ring,
      (bb) —CO—CH(NH$_2$)—CH$_2$—COOH,
      (cc) —CO—CH(NH$_2$)—CH$_2$—CONH$_2$,
      (dd) —CO—CH(NH$_2$)—CH$_2$—CH$_2$—COOH,
      (ee) —CO—CH(NH$_2$)—CH$_2$—CH$_2$—CONH$_2$,
      (ff) —CO—CH(NH$_2$)—CH$_2$—C*—NH— CH=N—C*H= where the carbon atoms marked with an "*" are bonded together to form a heterocyclic ring,
  (gg) —CO—CH(NH$_2$)—CH$_2$—CH$_2$—CH$_2$—NH—C(=NH)—NH$_2$,
  (hh) —CO—CH(NH$_2$)—CH$_2$—CH$_2$—CH$_2$—CH$_2$—NH$_2$,
  (ii) —CO—CH(NH$_2$)—CH$_2$—CH$_2$—CH(OH)—CH$_2$—NH$_2$,
  (jj) —CO—CH$_2$—CH$_2$—NH$_2$,
  (kk) —CO—CH$_2$—CH$_2$—CH$_2$—NH$_2$,
  (ll) —CO—CH(NH$_2$)—CH$_2$—CH$_2$—CH$_2$—NH$_2$,
  (mm) —CO—CH(NH$_2$)—CH$_2$—CH$_2$—CH$_2$—NH—CO—NH$_2$,
  (nn) —CO—CH(NH$_2$)—CH$_2$—CH$_2$—OH,
(6) —SR$_{5-2}$ where R$_{5-2}$ is defined above,
(7) —NHR$_{5-3}$ where R$_{5-3}$ is —H or C$_1$-C$_4$ alkyl,
(8) —NR$_{5-4}$R$_{5-5}$ where R$_{5-4}$ and R$_{5-5}$ are the same or different and are C$_1$-C$_4$ alkyl or may taken together with the attached nitrogen atom to form the heterocyclic ring —N*—(CH$_2$)$_{n1}$—R$_{5-6}$—(CH$_2$)$_{n2}$—* where the atoms marked with an asterisk (*) are bonded together resulting in the formation of a ring, where n$_1$ is 1 thru 5, n$_2$ is 0 thru 3 and R$_{5-6}$ is
  (a) —CH$_2$—,
  (b) —O—,
  (c) —S—,
  (d) —NR$_{5-9}$ where R$_{5-9}$ is
    (i) C$_1$-C$_6$ alkyl optionally substituted with 1 thru 3 —OH or —OCH$_3$,
    (ii) C$_1$-C$_6$ alkylcarbonyl,
    (iii) C$_1$-C$_6$ alkoxycarbonyl,
    (iv) C$_6$-C$_{12}$ arylalkyl,
    (v) -ϕ,
    (vi) —SO$_2$—C$_1$-C$_8$ alkyl,
    (vii) CH$_3$—C*—O—CO—O—C*—CH$_2$— where the carbon atoms designated by * are attached by a double bond to form a five member ring,
(9) —(CH$_2$)$_{n3}$CO$_2$R$_{5-2}$, where n$_3$ is 0 thru 6 and R$_{5-2}$ is as defined above,
(10) —(CH$_2$)$_{n3}$CON(R$_{5-3}$)$_2$ where n$_3$ is as defined as above and where R$_{5-3}$ may be the same or different and is defined above,
(11) —(CH$_2$)$_{n3}$CONR$_{5-4}$R$_{5-5}$ where n$_3$, R$_{5-4}$, R$_{5-5}$ are as defined above,
(12) —(CH$_2$)$_{n1}$OR$_{5-2}$ where R$_{5-2}$ and n$_1$ are as defined above,
(13) —(CH$_2$)$_{n1}$OCOR$_{5-3}$ where R$_{5-3}$ and n$_1$ are as defined above,
(14) —(CH$_2$)$_{n1}$SR$_{5-2}$ where R$_{5-2}$ and n$_1$ are as defined above,
(15) —(CH$_2$)$_{n1}$NHR$_{5-3}$ where R$_{5-3}$ and n$_1$ are as defined above,
(16) —(CH$_2$)$_{n1}$NR$_{5-4}$R$_{5-5}$ where R$_{5-4}$, R$_{5-5}$, and n$_1$ are as defined above,
(C$_5$-3)
  (C) —(CH$_2$)$_{n3}$-ϕ optionally substituted with 1 thru 4 R$_{5-1}$ where R$_{5-1}$ and n$_3$ are as defined as above,
  (D) —(CH$_2$)$_{n3}$-pyridin-2-, 3- or 4-yl optionally substituted with 1 thru 4 R$_{5-1}$ where n$_3$ and R$_{5-1}$ are as defined above,
  (E) —(CH$_2$)$_{n3}$-naphthalin-1-, 2-yl optionally substituted with 1 thru 4 R$_{5-1}$ where n$_3$ and R$_{5-1}$ are as defined above,
(C$_5$-5)
  (F) —(CH$_2$)$_{n3}$CO$_2$R$_{5-2}$ where n$_3$ and R$_{5-2}$ are as defined above,
(C$_5$-6)
  (G) —(CH$_2$)$_{n3}$CON(R$_{5-3}$)$_2$ where n$_3$ is as defined as above and where R$_{5-3}$ may be the same or different and is as defined above,
(C$_5$-7)
  (H) —(CH$_2$)$_{n3}$CONR$_{5-4}$R$_{5-5}$ where n$_3$, R$_{5-4}$, R$_{5-5}$ are as defined above,
(C$_5$-8)
  (I) —(CH$_2$)$_{n3}$SO$_3$R$_{5-2}$ where n$_3$ and R$_{5-2}$ are as defined above,
(C$_5$-9)
  (J) —C$_3$-C$_7$ cycloalkyl;
where
R$_{2-1}$ is
  (A) —H,
  (B) C$_1$-C$_8$ alkyl optionally substituted with 1 thru 4
    (1) —F,
    (2) —Cl,
    (3) —OR$_{5-2}$ where R$_{5-2}$ is as defined above,
    (4) —N(R$_{5-9}$)$_2$ where R$_{5-9}$ may be the same or different and is as defined above;
where
R$_{2-2}$ is
  (A) —H,
  (B) C$_1$-C$_8$ alkyl optionally substituted with 1 thru 4
    (1) —F,
    (2) —Cl,
    (3) —OR$_{5-2}$ where R$_{5-2}$ is as defined above,
    (4) —N(R$_{5-9}$)$_2$ where R$_{5-9}$ may be the same or different and is as defined above, or R$_{2-1}$ and R$_{2-2}$ are taken together with the attached nitrogen atom to form a heterocyclic ring selected from the group consisting of
(A) 1-pyrrolidinyl optionally substituted on carbon with 1 thru 3 R$_{2-3}$ where R$_{2-3}$ is selected from the group of
  (1) C$_1$-C$_6$ alkyl optionally substituted with 1 thru 3 —OH or —OCH$_3$,
  (2) C$_1$-C$_6$ alkenyl optionally substituted with 1 thru 3 —OH or —OCH$_3$,
  (3) C$_1$-C$_6$ alkylcarbonyl,
  (4) C$_1$-C$_6$ alkoxycarbonyl,
  (5) C$_6$-C$_{12}$ arylalkyl,
  (6) =O,
  (7) —OH,
  (8) —C≡N,
  (9) —CO$_2$R$_{2-4}$ where R$_{2-4}$ is
    (a) —H,
    (b) C$_1$-C$_4$ alkyl,
    (c) C$_6$-C$_{12}$ aryl,
    (d) C$_6$-C$_{12}$ aralkyl,
  (10) —NH$_2$,
  (11) —Cl,
  (12) —F,
  (13) —Br,
  (14) -ϕ optionally substituted with 1 thru 3 —F, —Cl, —Br, —OH, —OCH$_3$, —OCH$_2$-ϕ, —NO$_2$, C$_1$-C$_3$ alkyl, —NH$_2$, —NHCH$_3$, N(CH$_3$)$_2$, —CO$_2$R$_{2-4}$ where R$_{2-4}$ is as defined above,
  (15) —(CH$_2$)$_{n4}$NR$_{2-6}$R$_{2-7}$ where R$_{2-6}$ and R$_{2-7}$ are the same or different and are C$_1$-C$_4$ alkyl or may taken together with the attached nitrogen atom to form the heterocyclic ring —N*—(CH$_2$)$_{n5}$—R$_{2-8}$—(CH$_2$)$_{n6}$—* where the atoms marked with an asterisk (*) are bonded together resulting in the formation of a ring, where n$_4$ is 0 thru 3, n$_5$ is 1 thru 5, n$_6$ is 0 thru 3 and R$_{2-8}$ is (a) —CH$_2$—,
(b) —O—,
(c) —S—,
(d) —NR$_{2-4}$ where R$_{2-4}$ is as defined above, (B) 1-piperdinyl optionally substituted on carbon with 1 thru 3 R$_{2-3}$ where R$_{2-3}$ is as defined above, (C) 1-morpholinyl optionally substituted on carbon with 1 thru 3 R$_{2-3}$ where R$_{2-3}$ is as defined above, (D) 1-piperazinyl optionally substituted on carbon with 1 thru 3 R$_{2-3}$ where R$_{2-3}$ is as defined above and optionally substituted in the 4-position with R$_{2-5}$ where R$_{2-5}$ is
  (1) C$_1$-C$_6$ alkyl optionally substituted with 1 thru 3 —OH or —OCH$_3$,
  (2) C$_1$-C$_6$ alkylcarbonyl,
  (3) C$_1$-C$_6$ alkoxycarbonyl,
  (4) C$_6$-C$_{12}$ arylalkyl,
  (5) -φ,
  (6) —SO$_2$-C$_1$-C$_8$ alkyl,
  (7) CH$_3$—C*—O—CO—O—C*—CH$_2$— where the carbon atoms designated by * are attached by a double bond to form a five member ring, (E) 1-aziridinyl optionally substituted on carbon with 1 thru 2 R$_{2-3}$ where R$_{2-3}$ is as defined above, (F) 1-azetidinyl optionally substituted on carbon with 1 thru 3 R$_{2-3}$ where R$_{2-3}$ is as defined above, (G) 1-hexamethyleneimino optionally substituted on carbon with 1 thru 3 R$_{2-3}$ where R$_{2-3}$ is as defined above, (H) 1-pyrrolyl optionally substituted on carbon with 1 thru 3 R$_{2-3}$ where R$_{2-3}$ is as defined above, (I) 1-imidazolyl optionally substituted on carbon with 1 thru 3 R$_{2,3}$ where R$_{2-3}$ is as defined above, (J) 1-pyrazoyl optionally substituted on carbon with 1 thru 3 R$_{2-3}$ where R$_{2-3}$ is as defined above, (K) 1-pyrazolidinyl optionally substituted on carbon with 1 thru 3 R$_{2-3}$ where R$_{2-3}$ is as defined above, (L) 1,2,3-triazolyl optionally substituted on carbon with 1 thru 3 R$_{2-3}$ where R$_{2-3}$ is as defined above, (M) 1,2,4-triazolyl optionally substituted on carbon with 1 thru 3 R$_{2-3}$ where R$_{2-3}$ is as defined above, (N) 1-tetrazolyl optionally substituted on carbon with 1 thru 3 R$_{2-3}$ where R$_{2-3}$ is as defined above, (O) 1-thiomorpholinyl optionally substituted on carbon with 1 thru 3 R$_{2-3}$ where R$_{2-3}$ is as defined above, (P) 1-thiazolidinyl, optionally substituted on carbon with 1 thru 3 R$_{2-3}$ where R$_{2-3}$ is as defined above,

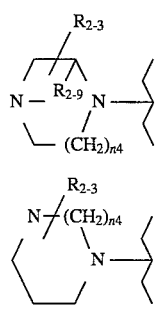
(Q)(R$_{2-1}$/R$_{2-2}$-1)

(R)(R$_{2-1}$/R$_{2-2}$-2)

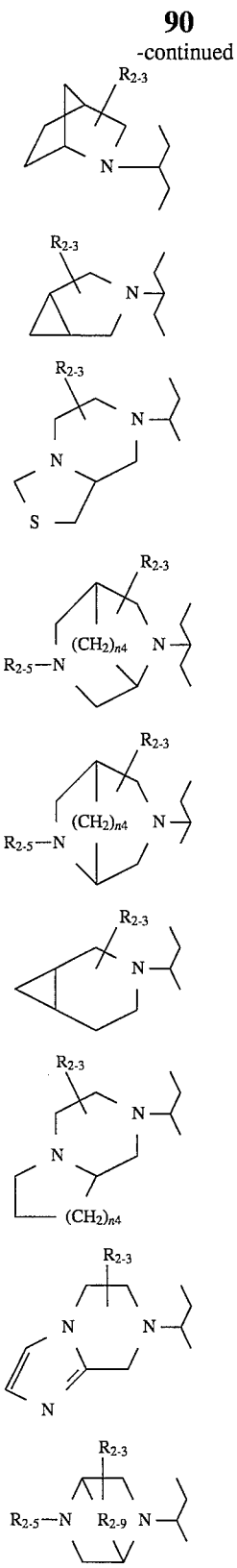
(S)(R$_{2-1}$/R$_{2-2}$-3)

(T)(R$_{2-1}$/R$_{2-2}$-4)

(U)(R$_{2-1}$/R$_{2-2}$-5)

(V)(R$_{2-1}$/R$_{2-2}$-6)

(W)(R$_{2-1}$/R$_{2-2}$-7)

(X)(R$_{2-1}$/R$_{2-2}$-8)

(Y)(R$_{2-1}$/R$_{2-2}$-9)

(Z)(R$_{2-1}$/R$_{2-2}$-10)

(AA)(R$_{2-1}$/R$_{2-2}$-11)

-continued

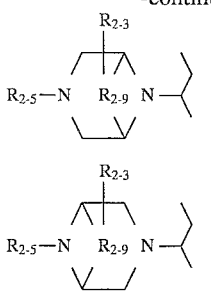

where
$R_{2-3}$ and $R_{2-5}$ are as defined above,
where
$R_{2-9}$ is
(A) $-(CH_2)_{n4}$ where $n_4$ is 1 thru 3,
(B) $-CH_2OCH_2$,
(C) $-CH_2SCH_2$,
(D) $-CH_2SO_2CH_2$,
(E) $-CH_2S$,
(F) $-CH_2SO_2$,
(G) $-CH_2N(R_{2-5})CH_2$ where $R_{2-5}$ is as defined above, with the proviso that $R_{2-1}$ and $R_{2-2}$ can not both be $-H$;

where $R_{4-1}$ is defined the same as $R_{2-1}$, but may be the same or different than $R_{2-1}$, where $R_{4-2}$ is defined the same as $R_{2-2}$, but may be the same or different than $R_{2-2}$, with the proviso that $R_{4-1}$ and $R_{4-2}$ can not both be $-H$;

where ($R_6$-1) $R_6$ is defined the same as $R_5$, but may be the same or different than $R_5$, with the proviso that;
(I) one of $R_5$, $R_6$ or $R_7$ must be selected from the group consisting of
($C_5$-3)
(C) $-(CH_2)_{n3}$-φ optionally substituted with 1 thru 4 $R_{5-1}$ where $R_{5-1}$ and $n_3$ as defined as above,
(D) $-(CH_2)_{n3}$-pyridin-2-, 3- or 4-yl optionally substituted with 1 thru 4 $R_{5-1}$ where $n_3$ and $R_{5-1}$ are as defined above,
(E) $-(CH_2)_{n3}$-naphthalin-1-, 2-yl optionally substituted with 1 thru 4 $R_{5-1}$ where $n_3$ and $R_{5-1}$ are as defined above, and
(II) for at least one of these three aromatic substituents, $n_3$ must be 0;

where $R_7$ is defined the same as $R_5$, but may be the same or different than $R_5$; with the proviso that $W_1$ and $W_3$ can not both be $-CH=$, and pharmaceutically acceptable salts thereof.

2. A bicyclic amine of formula (XXX) according to claim 1 where $W_1$ and $W_3$ are both $-N=$.

3. A bicyclic amine of formula (XXX) according to claim 1 where $W_5$ is $-CR_5=$.

4. A bicyclic amine of formula (XXX) according to claim 3 where $R_5$ is $-H$, $-CH_3$, -φ and 4-hydroxyphenyl.

5. A bicyclic amine of formula (XXX) according to claim 1 where $R_{2-1}$ and $R_{2-2}$ are taken together with the attached nitrogen atom to form 1-pyrrolidinyl, 1-piperazinyl, 1-thiomorpholinyl and 4-methylpiperazin-1-yl.

6. A bicyclic amine of formula (XXX) according to claim 5 where $R_{2-1}$ and $R_{2-2}$ are 1-pyrrolidinyl and 1-piperazinyl.

7. A bicyclic amine of formula (XXX) according to claim 1 where $R_{4-1}$ and $R_{4-2}$ are taken together with the attached nitrogen atom to form 1-pyrrolidinyl, 1-piperazinyl, 1-thiomorpholinyl and 4-methylpiperazin-1-yl.

8. A bicyclic amine of formula (XXX) according to claim 7 where $R_{4-1}$ and $R_{4-2}$ are 1-pyrrolidinyl and 1-piperazinyl.

9. A bicyclic amine of formula (XXX) according to claim 1 where $R_6$ is $-H$, $-CH_3$, -φ and 4-hydroxyphenyl.

10. A bicyclic amine of formula (XXX) according to claim 1 where $R_7$ is $-H$, $-CH_3$, -φ, 2-(1-morpholinyl)ethyl and 2-(1-piperazinyl)ethyl.

11. A bicyclic amine of formula (XXX) according to claim 1 where the pharmaceutically acceptable salts are salts of the following acids hydrochloric, hydrobromic, methanesulfonic, sulfuric, phosphoric, nitric, benzoic, citric, tartaric, fumaric, maleic, $CH_3-(CH_2)_n-COOH$ where n is 0 thru 4, $HOOC-(CH_2)_n-COOH$ where n is as defined above.

12. A bicyclic amine of formula (XXX) according to claim 1 where the bicyclic amine (XXX) is selected from the group consisting of
6-phenyl-2,4-di-(1-pyrrolidinyl)-7-methyl-7H-pyrrolo[2,3-d]pyrimidine,
6-phenyl-7-n-propyl-2,4-di-(1-pyrrolidinyl)-7H-pyrrolo[2,3-d]pyrimidine,
7-methyl-2,4-di-[N-methyl-N-(2-hydroxy)ethyl]-6-phenyl-7H-pyrrolo[2,3-d]pyrimidine,
2-[6-phenyl-2,4-di-1-pyrrolidinyl-7H-pyrrolo[2,3-d]pyrimidin-7-yl]ethanol,
2-[6-phenyl-2,4-di-1-pyrrolidinyl-7H-pyrrolo[2,3-d]pyrimidin-7-yl]ethyl,
2-[6-phenyl-2,4-di-1-pyrrolidinyl-7H-pyrrolo[2,3-d]pyrimidin-7-yl]-S-ethyl-1-thioacetate,
2-[6-phenyl-2,4-di-1-pyrrolidinyl-7H-pyrrolo[2,3-d]pyrimidin-7-yl]ethanethiol,
2-[6-phenyl-2,4-di-1-pyrrolidinyl-7H-pyrrolo[2,3-d]pyrimidin-7-yl]ethyl acetate,
7-tert-butyl-6-phenyl-2,4-di-1-pyrrolidinyl-7H-pyrrolo[2,3-d]pyrimidine,
6-phenyl-2,4-di-1-pyrrolidinyl-7H-pyrrolo[2,3-d]pyrimidine,
7-tert-butyl-6-(4-methoxyphenyl)-2,4-di-1-pyrrolidinyl-7H-pyrrolo[2,3-d]pyrimidine,
6-(4-hydroxyphenyl)-2,4-di-1-pyrrolidinyl-7H-pyrrolo[2,3-d]pyrimidine,
6-(4-methoxyphenyl)-2,4-di-1-pyrrolidinyl-7H-pyrrolo[2,3-d]pyrimidine,
7-methyl-6-phenyl-2,4-di-1-thiomorpholinyl-7H-pyrrolo[2,3-d]pyrimidine,
6-phenyl-7-[2-(1-piperazinyl)ethyl]-2,4-di-1-pyrrolidinyl-7H-pyrrolo[2,3-d]pyrimidine,
7-[2-(1-morpholinyl)ethyl]-6-phenyl-2,4-di-1-pyrrolidinyl-7H-pyrrolo[2,3-d]pyrimidine,
7-[2-(1-(4-methyl)piperazinyl)ethyl]-6-phenyl-2,4-di-1-pyrrolidinyl-7H-pyrrolo[2,3-d]pyrimidine,
2-[6-(4-methoxyphenyl)-2,4-di-1-pyrrolidinyl-7H-pyrrolo[2,3-d]pyrimidin-7-yl]ethanol,
2-[6-(4-hydroxyphenyl)-2,4-di-1-pyrrolidinyl-7H-pyrrolo[2,3-d]pyrimidin-7-yl]ethanol,
7-methyl-6-phenyl-2,4-di-1-pyrrolidinyl-7H-pyrrolo[2,3-d]pyrimidine,
6-phenyl-7-phenylmethyl-2,4-di-1-pyrrolidinyl-7H-pyrrolo[2,3-d]pyrimidine,
6,7-diphenyl-2,4-di-1-pyrrolidinyl-7H-pyrrolo[2,3-d]pyrimidine,
7-methyl-2,4-di-4-morpholinyl-6-phenyl-7H-pyrrolo[2,3-d]pyrimidine,
1,1'-(7-methyl-6-phenyl-7H-pyrrolo[2,3-d]pyrimidine-2,4-diyl)bis-3,4-pyrrolidinediol, 7-methyl-6-phenyl-2,4-di-1-piperazinyl-7H-pyrrolo[2,3-d]pyrimidine, 3,3'-[(7-methyl-6-phenyl-7H-pyrrolo[2,3-d]pyrimidine-2,4-diyl]bis-1,4-piperazinediyl]bis-1,2-propanediol, 4'-(7-methyl-6-phenyl-7H-pyrrolo[2,3-d]pyrimidine-2-4-diyl)bis-1-piperazineacetic acid diethyl ester, 4,4'-(7-methyl-6-phenyl-7H-pyrrolo[2,3-d]pyrimidine-2,4-diyl)bis-1-piperazineacetic acid, 5,7-dimethyl-6-phenyl-2,4-di-1-pyrrolidinyl-7H-pyrrolo[2,3-d]pyrimidine, 6-(4-methoxyphenyl)-7-methyl-2,4-di-1-pyrrolidinyl-7H-pyrrolo[2,3-d]pyrimidine, 4-(7-methyl-2,4-di-1-pyrrolidinyl-7H-pyrrolo[2,3-d]pyrimidin-6-yl)phenol, 7-methyl-6-(4-fluorophenyl)-2,4-di-1-pyrrolidinyl-7H-pyrrolo[2,3-d]pyrimidine, 2,6-bis(1,1-dimethylethyl)-4-(7-methyl-2,4-di-1-pyrrolidinyl-7H-pyrrolo[2,3-d]pyrimidine-6-yl)phenol, 2,6-bis(1-methylethyl)-4-(7-methyl-2, 4-di-1-pyrrolidinyl-7H-pyrrolo[2,3-d]pyrimidin-6-yl)phenol, 2,6-dimethyl-4-(7-methyl-2,4-di-1-pyrolidinyl-7H-pyrrolo[2,3-d]pyrimidin-6-yl)-phenol, 5-(7-methyl-2,4-di-1-pyrrolidinyl-7H-pyrrolo[2,3-d]pyrimidin-6-yl)-1,2,3-trimethoxybenzene, 6-[2-(4-methoxyphenyl)ethyl]-7-methyl-2,4-di-1-pyrrolidinyl-7H-pyrrolo[2,3d]pyrimidine, 5,6-bis(4-chlorophenyl)-7-methyl-2,4-di-1-pyrrolidinyl-7H-pyrrolo[2,3-d]pyrimidine, 5,6-bis(4-methoxyphenyl)-7-methyl-2, 4-di-1-pyrrolidinyl-7H-pyrrolo[2,3-d]pyrimidine, 4,4'-(7-methyl-2,4-di-1-pyrrolidinyl-7H-pyrrolo[2,3-d]pyrimidine-5,6-diyl)bisphenol, 6,7-bis(4-methoxyphenyl)-2,4-di-1-pyrrolidinyl-7H-pyrrolo[2,3-d]pyrimidine, 4,4'-(2,4-di-1-pyrrolidinyl-7H-pyrrolo[2,3-d]pyrimidine-6,7-diyl)bis-phenol, 5,6-bis(4-methoxyphenyl)-7-methyl-2,4-di-1-piperazinyl-7H-pyrrolo[2,3-d]pyrimidine, 7-methyl-5-phenyl-2,4-di-1-pyrrolidinyl-7H-pyrrolo[2,3-d]pyrimidine, 2,4-di-1H-imidazol-1-yl-7H-pyrrolo[2,3-d]pyrimidine, 2-(6-phenyl-2,4-di-1-pyrrolidinyl-7H-pyrrolo[2,3-d]pyrimidin-7-yl)ethanesulfonic acid, 6-(3,4-dimethoxyphenyl)-7-methyl-2,4-di-1-pyrrolidinyl-7H-pyrrolo[2,3-d]pyrimidine, 4-(7-methyl-2,4-di-1-pyrrolidinyl-7H-pyrrolo[2,3-d]pyrimidin-6-yl)-1,2-benzenediol, 6-(2,5-dimethoxyphenyl)-7-methyl-2,4-di-1-pyrrolidinyl-7H-pyrrolo[2,3-d]pyrimidine, 2-(7-methyl-2, 4-di-1-pyrrolidinyl-7H-pyrrolo[2,3-d]pyrimidin-6-yl)-1,4-benzenediol, 6-(2-fluoro-4-methoxyphenyl)-7-methyl-2,4-di-1-pyrrolidinyl-7H-pyrrolo[2,3d]pyrimidine, 6-(2-methoxyphenyl)-7-methyl-2,4-di-1-pyrrolidinyl-7H-pyrrolo[2,3-d]pyrimidine, 2-(7-methyl-2,4-di-1-pyrrolidinyl-7H-pyrrolo[2,3-d]pyrimidin-6-yl)-phenol, 6-(2-pyridinyl)-7-methyl-2,4-di-1-pyrrolidinyl-7H-pyrrolo[2,3-d]pyrimidine, 2-methoxy-5-(7-methyl-2,4-di-pyrrolidin-1-yl-7H-pyrrolo[2,3-d]pyrimidin-6-yl)benzoic acid methyl ester, 2-hydroxy-5-(7-methyl-2,4-di-pyrrolidin-1-yl-7H-pyrrolo[2,3-d]pyrimidin-6-yl)-benzoic acid, 4,4'-(7-methyl-2,4-di-1-pyrrolidinyl-7H-pyrrolo[2,3-d]pyrimidin-5,6-diyl)-bis-phenol, 6-(4-methoxyphenyl)-7-methyl-2,4-bis-piperazin-1-yl-7H-pyrrolo[2,3-d]pyrimidine, 6-(4-methoxyphenyl)-7-methyl-2,4-bis-piperazin-1-yl-7H-pyrrolo[2,3-d]pyrimidine dimethanesulfonate, 4- (7-methyl-2,4-di-piperazinyl-7H-pyrrolo[2,3- d]pyrimidin-6- yl)phenol, 2,4-bis(3-amino-1-pyrrolidinyl)-6-(4-methoxyphenyl)-7-methyl-7H-pyrrolo[2,3-d]pyrimidine, 4-[2,4-bis(3-amino-1-pyrrolidinyl)-7-methyl-7H-pyrrolo[2,3-d]pyrimidin-6-yl]phenol, 6-(4-methoxyphenyl)-7-methyl-2,4-di-1-pyrrolidinyl-7H-pyrrolo[2,3-d]pyrimidine-5-carbaldehyde, 6-(4-methoxyphenyl)-7-methyl-2,4-di-1-pyrrolidinyl-7H-pyrrolo[2,3-d]pyrimidin-5-yl]methanol, 6-(4-methoxyphenyl)-7-methyl-2, 4-di-1-pyrrolidinyl-7H-pyrrolo[2,3-d]pyrimidine-5-carbaldehyde oxime, 6-(4-methoxyphenyl)-7-methyl-2,4-di-1-pyrrolidinyl-7H-pyrrolo[2,3-d]pyrimidine-5-carbonitrile, 4-(7-methyl-2,4-di-1-pyrrolidinyl-7H-pyrrolo[2,3-d]pyrimidin-6-yl)phenol, 2,6-bis(1-pyrrolidinylmethyl)-4-(7-methyl-2,4-di-1-pyrrolidinyl-7H-pyrrolo[2,3d]pyrimidin-6-yl)phenol, 6-phenyl-7-[2-(1-(3,4,5-trimethyl)piperazinyl)ethyl]-2,4-di-1-pyrrolidinyl-7H-pyrrolo[2,3-d]pyrimidine, 7-[2-(1-(3,5-dimethyl)piperazin yl)ethyl]-6-phenyl-2,4-di-1-pyrrolidinyl-7H-pyrrolo[2,3-d]pyrimidine, 7-[2-(1-(3,5-dimethyl)piperazinyl)ethyl]-6-(4-fluorophenyl)-2,4-di-1-pyrrolidinyl-7H-pyrrolo[2,3-d]pyrimidine, 6-(4-fluorophenyl)-7-[2-(1-(3,4,5-trimethyl)piperazinyl)ethyl]-2,4-di-1-pyrrolidinyl-7H-pyrrolo[2,3-d]pyrimidine, 2-[6-(4-methylphenyl)-2,4-di-1-pyrrolidinyl-7H-pyrrolo[2,3-d]pyrimidin-7-yl]ethanol, 6-(4-methylphenyl)-7-[2-(1-(3,4,5-trimethyl)piperazinyl)ethyl]-2,4-di-1-pyrrolidinyl-7H-pyrrolo[2,3-d]pyrimidine, 6-(4-methylphenyl)-7-[2-(1-piperazinyl)ethyl]-2,4-di-1-pyrrolidinyl-7H-pyrrolo[2,3-d]pyrimidine, 7-[2-(1-(3,5-dimethyl)piperazinyl)ethyl]-6-(4-methylphenyl) -2,4-di-1-pyrrolidinyl-7H-pyrrolo[2,3-d]pyrimidine, 6-(4-fluorophenyl)-7-[2-(1-piperazinyl)ethyl]-2,4-di-1-pyrrolidinyl-7H-pyrrolo[2,3-d]pyrimidine, 5-methyl-6-(4-methylphenyl)-7-[2-(1-piperazinyl)ethyl]-2,4-di-1-pyrrolidinyl-7H-pyrrolo[2,3-d]pyrimidine, 7-[2-(1-(3,5-dimethyl)piperazinyl)ethyl]-5-methyl-6-(4-methylphenyl)-2,4-di-1-pyrrolidinyl-7H-pyrrolo[2,3-d]pyrimidine, 6-(4-fluorophenyl)-5-methyl-7-[2-(1-piperazinyl)ethyl]-2,4-di-1-pyrrolidinyl-7H-pyrrolo[2,3-d]pyrimidine, 7-[2-(1-(3,5-dimethyl)piperazinyl)ethyl]-6-(4-fluorophenyl)-5-methyl-2,4-di-1-pyrrolidinyl-7H-pyrrolo[2,3-d]pyrimidine, 6-(4-methoxyphenyl)-7-methyl-2,4-bis-(4-methylpiperazin-1-yl)-7H-pyrrolo[2,3d]pyrimidine, 4-[7-methyl-2,4-bis-(4-methylpiperazin-1-yl)-7H-pyrrolo[2,3-d]pyrimidin-6-yl]-phenol, 4-methyl-2,4-bis-(4-methylpiperazin-1-yl)-6-phenyl-7H-pyrrolo[2,3-d]pyrimidine,

95

5,6-(bis-(4-methoxyphenyl)-7-methyl-2,4-bis(4-methylpiperazin-1-yl)-7H-pyrrolo[2,3-d]pyrimidine, 7-methyl-6-pyridin-3-yl-2,4-di-1-pyrrolidinyl-7H-pyrrolo[2,3-d]pyrimidine, 6-phenyl-7-[2-(1-glucosyl)ethyl]-2,4-di-1-pyrrolidinyl-7H-pyrrolo[2,3-d]pyrimidine,

[4-(7-methyl-2,4-di-1-pyrrolidinyl-7H-pyrrolo[2,3-d]pyrimidin-6-yl)phenoxy]acetic acid methyl ester,

[4-(7-methyl-2,4-di-1-pyrrolidinyl-7H-pyrrolo[2,3-d]pyrimidin-6-yl)-phenoxy]acetic acid N-hydroxy-N-methyl-4-(7-methyl-2,4-di-1-pyrrolidinyl-7H-pyrrolo[2,3-d]pyrimidin-6-yl)phenoxyacetamide, 4-(7-methyl-2,4-di-1-pyrrolidinyl-7H-pyrrolo[2,3-d]pyrimidin-6-yl)phenol, sulfate, diethyl-[2-[4-(7-methyl-2,4-di-1-pyrrolidinyl-7H-pyrrolo[2,3-d]pyrimidin-6-yl)-phenoxy]ethyl]amine, 4-(7-methyl-2,4-di-1-pyrrolidinyl-7H-pyrrolo[2,3-d]pyrimidin-6-yl)-phenol, N,N-dimethylsulfamoyl, 4-(7-methyl-2,4-di-1-pyrrolidinyl-7H-pyrrolo[2,3-d]pyrimidin-6-yl)-phenol,2-{2[2-(2-methoxy)ethoxy]ethoxy}ethyl ether, 4-(7-methyl-2,4-di-1-pyrrolidinyl-7H-pyrrolo[2,3-d]pyrimidin-6-yl)-phenol,1-(2-imidazol-1-yl)ethyl ether, 4-(7-methyl-2,4-di-1-pyrrolidinyl-7H-pyrrolo[2,3-d]pyrimidin-6-yl)phenyl-N,N-dimethyl carbamate, 4-(7-methyl-2,4-bis-pyrrolidin-1-yl-7H-pyrrolo[2,3-d]pyrimidin-6-yl)-benzoic acid ethyl ester, 6-(4-bromophenyl)-7-methyl-2,4-di-1-pyrrolidinyl-7H-pyrrolo[2,3-d]pyrimidine, 4-(7-methyl-2,4-bis-pyrrolidin-1-yl-7H-pyrrolo[2,3-d]pyrimidin-6-yl)-benzonitrile, 7-methyl-2,4-bispyrrolidin-1-yl-6-[4-(1H-tetrazol-5-yl)-phenyl]-7H-pyrrolo[2,3-d]pyrimidine, 4-(7-methyl-2,4-bis-pyrrolidin-1-yl-7H-pyrrolo(2,3-d)pyrimidine-6-yl)-benzamide, 4-(7-methyl-2,4-bis-pyrrolidin-1-yl-7H-pyrrolo[2,3-d]pyrimidin-6-yl)-benzoic acid, 2-[4-(7-methyl-2,4-bis-pyrrolidin-1-yl-7H-pyrrolo[2,3-d]pyrimidin-6-yl)benzoylamino]ethanesulfonic acid, 4-(7-methyl-2,4-bis-pyrrolidin-1-yl-7H-pyrrolo[2,3-d]pyrimidin-6-yl)—N-(1H-tetrazol-5-yl)-benzamide, 4-(7-methyl-2,4-di-1-pyrrolidinyl-7H-pyrrolo-[2,3-d]pyrimidin-6-yl)phenylamine, N-[4-(7-methyl-2,4-bis-pyrrolidin-1-yl-7H-pyrrolo[2,3-d]pyrimidin-6-yl)phenyl]methanesulfonamide, 4-(7-methyl-2,4-di-1-pyrrolidinyl-7H-pyrrolo[2,3-d]pyrimidin-6-yl)phenylamine bis(methanesulfonamide),

[4-(7-methyl-2,4-bis-pyrrolidin-1-yl-7H-pyrrolo[2,3-d]pyrimidin-6-yl)-phenyl]guanidine

13. A bicyclic amine of formula (XXX) according to claim 12 which is selected from the group consisting of 6-phenyl-2,4-di-(1-pyrrolidinyl)-7-methyl-7H-pyrrolo[2,3-d]pyrimidine, 6-phenyl-7-[2-(1-piperazinyl)ethyl]-2,4-di-1-pyrrolidinyl-7H-pyrrolo[2,3-d]pyrimidine, 7-[2-(1-morpholinyl)ethyl]-6-phenyl-2,4-di-1-pyrrolidinyl-7H-pyrrolo[2,3-d]pyrimidine, 2-[6-(4-hydroxyphenyl)-2,4-di-1-pyrrolidinyl-7H-pyrrolo[2,3-d]pyrimidin-7-yl]ethanol, 4-(7-methyl-2,4-di-1-pyrrolidinyl-7H-pyrrolo[2,3-d]pyrimidin-6-yl)phenol, 2,6-dimethyl-4-(7-methyl-2,4-di-1-pyrolidinyl-7H-pyrrolo[2,3-d]pyrimidin-6-yl)-phenol,

96

4,4'-(2,4-di-1-pyrrolidinyl-7H-pyrrolo[2,3-d]pyrimidine-6,7-diyl)bis-phenol, 5,6-bis(4-methoxyphenyl)-7-methyl-2,4-di-1-piperazinyl-7H-pyrrolo[2,3-d]pyrimidine, 7-[2-(1-(3,5-dimethyl)piperazinyl)ethyl]-6-(4-fluorophenyl)-2,4-di-1-pyrrolidinyl-7H-pyrrolo[2,3-d]pyrimidine, 6-(4-methylphenyl)-7-[2-(1-piperazinyl)ethyl]-2,4-di-1-pyrrolidinyl-7H-pyrrolo[2,3-d[pyrimidine.

14. A bicyclic amine of formula (XXX) according to claim 13 which is selected from the group consisting of 6-phenyl-2,4-di-(1-pyrrolidinyl)-7-methyl-7H-pyrrolo[2,3-d]pyrimidine, 4-(7-methyl-2,4-di-1-pyrrolidinyl-7H-pyrrolo[2,3-d]pyrimidin-6-yl)phenol.

15. A bicyclic heterocyclic amines of the formula (XXX)

$$\begin{array}{c} R_{2-2} \diagdown N \diagup R_{2-1} \\ \| \\ W_3 \diagup C \diagdown W_1 \\ R_{4-1} \diagdown N \diagup \diagdown \diagup N - R_7 \\ R_{4-2} \diagup \diagup \diagdown \diagup \\ W_5 = \\ R_6 \end{array} \quad (XXX)$$

where $W_1$ is —N═;

$W_3$ is —N═;

$W_5$ is —CR$_5$—;

($R_6$-2)

where $R_5$ and $R_6$ are taken together with the attached carbon atoms to form a ring selected from the group consisting of ($R_6$-2A)

—C*—(CH$_2$)$_{n7}$—C*— where the carbon atoms marked by an asterick (*) are the carbon atoms in the 5-member nitrogen containing ring which are bonded together by the double bond (C═C), where $n_7$ is 3–5, and ($R_6$-2B)

—C*—CR$_{56-1}$═CR$_{56-2}$—CR$_{56-3}$═CR$_{56-4}$—C*— where the carbon atoms marked by an asterick (*) are the carbon atoms in the 5-member nitrogen containing ring which are bonded together by the double bond (C═C), where $R_{56-1}$, $R_{56-2}$, $R_{56-3}$ and $R_{56-4}$ are —H, —F, —Cl, —Br, —OH, —NO$_2$, $C_1$–$C_3$ alkyl, —NH$_2$, —NHCH$_3$, N(CH$_3$)$_2$, —CO$_2$R$_{56-5}$ where $R_{56-5}$ is:

—H, $C_1$–$C_4$ alkyl, $C_6$–$C_{12}$ aryl, $C_6$–$C_{12}$ aralkyl;

where $R_{2-1}$ is (A) —H, (B) $C_1$–$C_8$ alkyl optionally substituted with 1 thru 4

(1) —F, (2) —Cl, (3) —OR$_{2-10}$ where $R_{2-10}$ is (a) —H, (b) $C_1$–$C_4$ alkyl, (c) phosphate, (d) sulfate, (e) —CO—R$_{2-11}$ where $R_{2-11}$ is $C_1$–$C_4$ alkyl or $C_6$–$C_9$ aralkyl, (f) —CO—NR$_{2-12}$R$_{2-13}$ where $R_{2-12}$ and $R_{2-13}$ are the same or different and are —H or $C_1$–$C_3$ alkyl, (g) sulfamate,
(h) glucosyl,
(i) galactosyl,
(j) glucuronic acid,
(k) maltosyl,
(l) arabinosyl,
(m) xylosyl,
(n) —CO—CH(NH$_2$)—H,
(o) —CO—CH(NH$_2$)—CH$_3$,
(p) —CO—CH(NH$_2$)—CH(CH$_3$)$_2$,
(q) —CO—CH(NH$_2$)—CH$_2$—CH(CH$_3$)$_2$,
(r) —CO—CH(NH$_2$)—CH(CH$_3$)—CH$_2$—CH$_3$,
(s) —CO—CH(NH$_2$)—CH$_2$—OH
(t) —CO—CH(NH$_2$)—CH(OH)—CH$_3$,
(u) —CO—CH(NH$_2$)—CH$_2$-φ,
(v) —CO—CH(NH$_2$)—CH$_2$-[p-phenyl]—OH,
(w) —CO—CH(NH$_2$)—CH$_2$-[2-indolyl]
(x) —CO—CH(NH$_2$)—CH$_2$—SH,
(y) —CO—CH(NH$_2$)—CH$_2$—CH$_2$—S—CH$_3$,
(z) —CO—C*H—NH—CH$_2$—CH$_2$—C*H$_2$ where the carbon atoms marked with an "*" are bonded together to form a heterocyclic ring,
(aa) —CO—C*H—NH—CH$_2$—CH(OH)—C*H$_2$ where the carbon atoms marked with an "*" are bonded together to form a heterocyclic ring,
(bb) —CO—CH(NH$_2$)—CH$_2$—COOH,
(cc) —CO—CH(NH$_2$)—CH$_2$—CONH$_2$,
(dd) —CO—CH(NH$_2$)—CH$_2$—CH$_2$—COOH,
(ee) —CO—CH(NH$_2$)—CH$_2$—CH$_2$—CONH$_2$,
(ff) —CO—CH(NH$_2$)—CH$_2$—C*—NH—CH=N—C*H= where the carbon atoms marked with an "*" are bonded together to form a heterocyclic ring,
(gg) —CO—CH(NH$_2$)—CH$_2$—CH$_2$—CH$_2$—NH—C(=NH)—NH$_2$,
(hh) —CO—CH(NH$_2$)—CH$_2$—CH$_2$—CH$_2$—CH$_2$—NH$_2$,
(ii) —CO—CH(NH$_2$)—CH$_2$—CH$_2$—CH(OH)—CH$_2$—NH$_2$,
(jj) —CO—CH$_2$—CH$_2$—NH$_2$,
(kk) —CO—CH$_2$—CH$_2$—CH$_2$—NH$_2$,
(ll) —CO—CH(NH$_2$)—CH$_2$—CH$_2$—CH$_2$—NH$_2$,
(mm) —CO—CH(NH$_2$)—CH$_2$—CH$_2$—CH$_2$—NH—CO—NH$_2$,
(nn) —CO—CH(NH$_2$)—CH$_2$—CH$_2$—OH, (4) —N(R$_{2-14}$)$_2$ where R$_{2-14}$ may be the same or different and is
(a) C$_1$–C$_6$ alkyl optionally substituted with 1 thru 3 —OH or —OCH$_3$,
(b) C$_1$–C$_6$ alkylcarbonyl,
(c) C$_1$–C$_6$ alkoxycarbonyl,
(d) C$_6$–C$_{12}$ arylalkyl,
(e) -φ,
(f) —SO$_2$—C$_1$–C$_8$ alkyl,
(g) CH$_3$—C*—O—CO—O—C*—CH$_2$— where the carbon atoms marked by an asterick (*) are attached by a double bond to form a five member ring, where
R$_{2-2}$ is
(A) —H,
(B) C$_1$–C$_8$ alkyl optionally substituted with 1 thru 4
(1) —F,
(2) —Cl,
(3) —OR$_{2-10}$ where R$_{2-10}$ is as defined above,
(4) —N(R$_{2-14}$)$_2$ where R$_{2-14}$ may be the same or different and is as defined above, or R$_{2-1}$ and R$_{2-2}$ are taken together with the attached nitrogen atom to form a heterocyclic ring selected from the group consisting of (A) 1-pyrrolidinyl optionally substituted on carbon with 1 thru 3 R$_{2-3}$ where R$_{2-3}$ is selected from the group of
(1) C$_1$–C$_6$ alkyl optionally substituted with 1 thru 3 —OH or —OCH$_3$,
(2) C$_1$–C$_6$ alkenyl optionally substituted with 1 thru 3 —OH or—OCH$_3$,
(3) C$_1$–C$_6$ alkylcarbonyl,
(4) C$_1$–C$_6$ alkoxycarbonyl,
(5) C$_6$–C$_{12}$ arylalkyl,
(6) =O,
(7) —OH,
(8) —C≡N,
(9) —CO$_2$R$_{2-4}$ where R$_{2-4}$ is
(a) —H,
(b) C$_1$–C$_4$ alkyl,
(c) C$_6$–C$_{12}$ aryl,
(d) C$_6$–C$_{12}$ aralkyl,
(10) —NH$_2$,
(11) —Cl,
(12) —F,
(13) —Br,
(14) -φ optionally substituted with 1 thru 3 —F, —Cl, —Br, —OH, —OCH$_3$, —OCH$_2$-φ, —NO$_2$, C$_1$C$_3$ alkyl, —NH$_2$, —NHCH$_3$, N(CH$_3$)$_2$, —CO$_2$R$_{2-4}$ where R$_{2-4}$ is as defined above,
(15) —(CH$_2$)$_{n4}$NR$_{2-6}$R$_{2-7}$ where R$_{2-6}$ and R$_{2-7}$ are the same or different and are C$_1$–C$_4$ alkyl or may taken together with the attached nitrogen atom to form the heterocyclic ring —N*—(CH$_2$)$_{n5}$—R$_{2-8}$—(CH$_2$)$_{n6}$* where the atoms marked with an asterisk (*) are bonded together resulting in the formation of a ring, where n$_4$ is 0 thru 3, n$_5$ is 1 thru 5, n$_6$ is 0 thru 3 and R$_{2-8}$ is
(a)—CH$_2$—,
(b) —O—,
(c) —S—,
(d) —NR$_{2-4}$ where R$_{2-4}$ is as defined above, (B) 1-piperdinyl optionally substituted on carbon with 1 thru 3 R$_{2-3}$ where R$_{2-3}$ is as defined above,
(C) 1-morpholinyl optionally substituted on carbon with 1 thru 3 R$_{2-3}$ where R$_{2-3}$ is as defined above,
(D) 1-piperazinyl optionally substituted on carbon with 1 thru 3 R$_{2-3}$ where R$_{2-3}$ is as defined above and optionally substituted in the 4-position with R$_{2-5}$ where R$_{2-5}$ is
(1) C$_1$–C$_6$ alkyl optionally substituted with 1 thru 3 —OH or —OCH$_3$,
(2) C$_1$–C$_6$ alkylcarbonyl,
(3) C$_1$–C$_6$ alkoxycarbonyl,
(4) C$_6$–C$_{12}$ arylalkyl,
(5) -φ,
(6)—SO$_2$—C$_1$–C$_8$ alkyl,
(7) CH$_3$—C*—O—CO—O—C*—CH$_2$— where the carbon atoms marked by an asterick (*) are attached by a double bond to form a five member ring,
(E) 1-aziridinyl optionally substituted on carbon with 1 thru 2 R$_{2-3}$ where R$_{2-3}$ is as defined above,
(F) 1-azetidinyl optionally substituted on carbon with 1 thru 3 R$_{2-3}$ where R$_{2-3}$ is as defined above,
(G) 1-hexamethyleneimino optionally substituted on carbon with 1 thru 3 R$_{2-3}$ where R$_{2-3}$ is as defined above,
(H) 1-pyrrolyl optionally substituted on carbon with 1 thru 3 R$_{2-3}$ where R$_{2-3}$ is as defined above, (I) 1-imidazolyl optionally substituted on carbon with 1 thru 3 $R_{2-3}$ where $R_{2-3}$ is as defined above, (J) 1-pyrazoyl optionally substituted on carbon with 1 thru 3 $R_{2-3}$ where $R_{2-3}$ is as defined above, (K) 1-pyrazolidinyl optionally substituted on carbon with 1 thru 3 $R_{2-3}$ where $R_{2-3}$ is as defined above, (L) 1,2,3-triazolyl optionally substituted on carbon with 1 thru 3 $R_{2-3}$ where $R_{2-3}$ is as defined above, (M) 1,2,4-triazolyl optionally substituted on carbon with 1 thru 3 $R_{2-3}$ where $R_{2-3}$ is as defined above, (N) 1-tetrazolyl optionally substituted on carbon with 1 thru 3 $R_{2-3}$ where $R_{2-3}$ is as defined above, (O) 1-thiomorpholinyl optionally substituted on carbon with 1 thru 3 $R_{2-3}$ where $R_{2-3}$ is as defined above, (P) 1-thiazolidinyl, optionally substituted on carbon with 1 thru 3 $R_{2-3}$ where $R_{2-3}$ is as defined above,

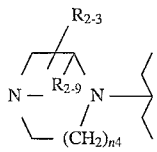 (Q)($R_{2-1}$/$R_{2-2}$-1)

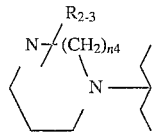 (R)($R_{2-1}$/$R_{2-2}$-2)

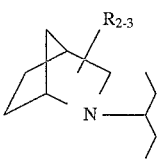 (S)($R_{2-1}$/$R_{2-2}$-3)

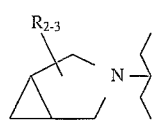 (T)($R_{2-1}$/$R_{2-2}$-4)

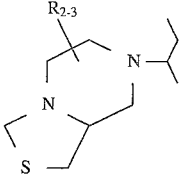 (U)($R_{2-1}$/$R_{2-2}$-5)

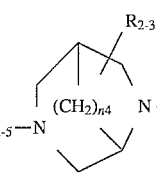 (V)($R_{2-1}$/$R_{2-2}$-6)

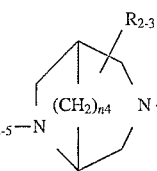 (W)($R_{2-1}$/$R_{2-2}$-7)

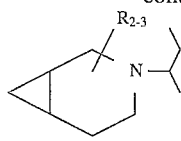 (X)($R_{2-1}$/$R_{2-2}$-8)

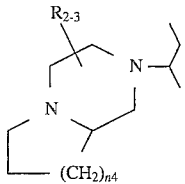 (Y)($R_{2-1}$/$R_{2-2}$-9)

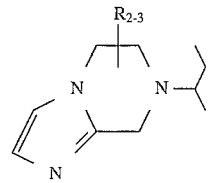 (Z)($R_{2-1}$/$R_{2-2}$-10)

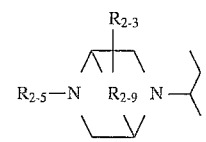 (AA)($R_{2-1}$/$R_{2-2}$-11)

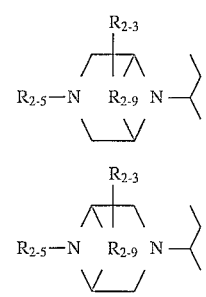 (BB)($R_{2-1}$/$R_{2-2}$-12)

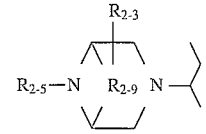 (CC)($R_{2-1}$/$R_{2-2}$-13)

where
$R_{2-3}$ and $R_{2-5}$ are as defined above,
where
$R_{2-9}$ is
(A) —$(CH_2)_{n4}$ where $n_4$ is 1 thru 3,
(B) —$CH_2OCH_2$,
(C) —$CH_2SCH_2$,
(D) —$CH_2SO_2CH_2$,
(E) —$CH_2S$,
(F) —$CH_2SO_2$,
(G) —$CH_2N(R_{2-5})CH_2$ where $R_{2-5}$ is as defined above, where $R_{4-1}$ is defined the same as $R_{2-1}$, but may be the same or different than $R_{2-1}$, where $R_{4-2}$ is defined the same as $R_{2-2}$, but may be the same or different than $R_{2-2}$; where $R_7$ is
($C_7$-1)
(A) —H,
($C_7$-2)
(B) $C_1$–$C_8$ alkyl optionally substituted with 1 thru 4 $R_{7-1}$ where $R_{7-1}$ is
(1) —F, —Cl, —Br,
(2) $C_1$–$C_4$ alkyl,
(3) —$CF_3$,
(4) -ϕ,
(5) —$OR_{7-2}$ where $R_{7-2}$ is
(a) —H,
(b) $C_1$–$C_4$ alkyl, (c) phosphate,
(d) sulfate,
(e) —CO—$R_{7-8}$ where $R_{7-8}$ is $C_1$–$C_4$ alkyl or $C_6$–$C_9$ aralkyl,
(f) —CO—$NR_{7-10}R_{7-11}$ where $R_{7-10}$ and $R_{7-11}$ are the same or different and are —H or $C_1$–$C_3$ alkyl,
(g) sulfamate,
(h) glucosyl,
(i) galactosyl,
(j) glucuronic acid,
(k) maltosyl,
(l) arabinosyl,
(m) xylosyl,
(n) —CO—CH($NH_2$)—H,
(o) —CO—CH($NH_2$)—$CH_3$,
(p) —CO—CH($NH_2$)—CH($CH_3$)$_2$,
(q) —CO—CH($NH_2$)—$CH_2$—CH($CH_3$)$_2$,
(r) —CO—CH($NH_2$)—CH($CH_3$)—$CH_2$—$CH_3$,
(s) —CO—CH($NH_2$)—$CH_2$—OH
(t) —CO—CH($NH_2$)—CH(OH)—$CH_3$,
(u) —CO—CH($NH_2$)—$CH_2$—$\phi$,
(v) —CO—CH($NH_2$)—$CH_2$—[p-phenyl]—OH,
(w) —CO—CH($NH_2$)—$CH_2$-[2-indolyl]
(x) —CO—CH($NH_2$)—$CH_2$—SH,
(y) —CO—CH($NH_2$)—$CH_2$—$CH_2$—S—$CH_3$,
(z) —CO—C*H—NH—$CH_2$—$CH_2$—C*$H_2$ where the carbon atoms marked with an asterick (*) are bonded together to form a heterocyclic ring,
(aa) —CO—C*H—NH—$CH_2$—CH(OH)—C*$H_2$ where the carbon atoms marked with an asterick (*) are bonded together to form a heterocyclic ring,
(bb) —CO—CH($NH_2$)—$CH_2$—COOH,
(cc) —CO—CH($NH_2$)—$CH_2$—$CONH_2$,
(dd) —CO—CH($NH_2$)—$CH_2$—$CH_2$—COOH,
(ee) —CO—CH($NH_2$)—$CH_2$—$CH_2$—$CONH_2$,
(ff) —CO—CH($NH_2$)—$CH_2$—C*—NH—CH=N—C*H= where the carbon atoms marked with an asterick (*) are bonded together to form a heterocyclic ring,
(gg) —CO—CH($NH_2$)—$CH_2$—$CH_2$—$CH_2$—NH—C(=NH)—$NH_2$,
(hh) —CO—CH($NH_2$)—$CH_2$—$CH_2$—$CH_2$—$CH_2$—$NH_2$,
(ii) —CO—CH($NH_2$)—$CH_2$—$CH_2$—CH(OH)—$CH_2$—$NH_2$,
(jj) —CO—$CH_2$—$CH_2$—$NH_2$,
(kk) —CO—$CH_2$—$CH_2$—$CH_2$—$NH_2$,
(ll) —CO—CH($NH_2$)—$CH_2$—$CH_2$—$CH_2$—$NH_2$,
(mm) —CO—CH($NH_2$)—$CH_2$—$CH_2$—$CH_2$—NH—CO—$NH_2$,
(nn) —CO—CH($NH_2$)—$CH_2$—$CH_2$—OH,
(6) —$SR_{7-2}$ where $R_{7-2}$ is defined above,
(7) —$NHR_{7-3}$ where $R_{7-3}$ is —H or $C_1$–$C_4$ alkyl,
(8) —$NR_{7-4}R_{7-5}$ where $R_{7-4}$ and $R_{7-5}$ are the same or different and are $C_1$–$C_4$ alkyl or may taken together with the attached nitrogen atom to form the heterocyclic ring —N*—($CH_2$)$_{n1}$—$R_{5-6}$—($CH_2$)$_{n2}$* where the atoms marked with an asterisk (*) are bonded together resulting in the formation of a ring, where $n_1$ is 1 thru 5, $n_2$ is 0 thru 3 and $R_{5-6}$ is
(a) —$CH_2$—,
(b) —O—,
(c) —S—,
(d) —$NR_{7-9}$ where $R_{7-9}$ is
  (i) $C_1$–$C_6$ alkyl optionally substituted with 1 thru 3 —OH or —$OCH_3$,
  (ii) $C_1$–$C_6$ alkylcarbonyl,
  (iii) $C_1$–$C_6$ alkoxycarbonyl,
  (iv) $C_6$–$C_{12}$ arylalkyl,
  (v) -$\phi$,
  (vi) —$SO_2$–$C_1$–$C_8$ alkyl,
  (vii) $CH_3$—C*—O—CO—O—C*—$CH_2$— where the carbon atoms designated by * are attached by a double bond to form a five member ring,
(9) —($CH_2$)$_{n3}$$CO_2R_{7-2}$, where $n_3$ is 0 thru 6 and $R_{7-2}$ is as defined above,
(10) —($CH_2$)$_{n3}$CON($R_{7-3}$)$_2$ where $n_3$ is as defined as above and where $R_{7-3}$ may be the same or different and is defined above,
(11) —($CH_2$)$_{n3}$$CONR_{7-4}R_{7-5}$ where $n_3$, $R_{7-4}$, $R_{7-5}$ are as defined above,
(12) —($CH_2$)$_{n1}$$OR_{7-2}$ where $R_{7-2}$ and $n_1$ are as defined above,
(13) —($CH_2$)$_{n1}$$OCOR_{7-3}$ where $R_{7-3}$ and $n_1$ are as defined above,
(14) —($CH_2$)$_{n1}$$SR_{7-2}$ where $R_{7-2}$ and $n_1$ are as defined above,
(15) —($CH_2$)$_{n1}$$NHR_{7-3}$ where $R_{7-3}$ and $n_1$ are as defined above,
(16) —($CH_2$)$_{n1}$$NR_{7-4}R_{7-5}$ where $R_{7-4}$, $R_{7-5}$, and $n_1$ are as defined above,
($C_5$-3)
(C) —($CH_2$)$_{n3}$-$\phi$ optionally substituted with 1 thru 4 $R_{7-1}$ where $R_{7-1}$ and $n_3$ are as defined as above,
(D) —($CH_2$)$_{n3}$-pyridin-2-, 3- or 4-yl optionally substituted with 1 thru 4 $R_{7-1}$ where $n_3$ and $R_{7-1}$ are as defined above,
(E) —($CH_2$)$_{n3}$-naphthalin-1-, 2-yl optionally substituted with 1 thru 4 $R_{7-1}$ where $n_3$ and $R_{7-1}$ are as defined above,
($C_5$-5)
(F) —($CH_2$)$_{n3}$$CO_2R_{7-2}$ where $n_3$ and $R_{7-2}$ are as defined above,
($C_5$-6)
(G) —($CH_2$)$_{n3}$CON($R_{7-3}$)$_2$ where $n_3$ is as defined as above and where $R_{7-3}$ may be the same or different and is as defined above,
($C_5$-7)
(H) —($CH_2$)$_{n3}$$CONR_{7-4}R_{7-5}$ where $n_3$, $R_{7-4}$, $R_{7-5}$ are as defined above,
($C_5$-8)
(I) —($CH_2$)$_{n3}$$SO_3R_{7-2}$ where $n_3$ and $R_{7-2}$ are as defined above,
($C_5$-9)
(J) —$C_3$–$C_7$ cycloalkyl; with the provisos:
  (1) that when $R_7$ is —H, $R_{56-1}$, $R_{56-3}$ and $R_{56-4}$ can not be —OH;
  (2) that when $R_{2-1}$ and $R_{2-2}$ is taken together with the attached nitrogen atom to form 1-pyrrolidinyl, and $R_{4-1}$ and $R_{4-2}$ is taken together with the attached nitrogen atom to form 1-pyrrolidinyl, $R_7$ is not —$CH_2$—$CH_2$-morphinyl; and pharmaceutically acceptable salts thereof.

16. A bicyclic amine of formula (XXX) according to claim 15 where $W_1$ and $W_3$ are both —N=.

17. A bicyclic amine of formula (XXX) according to claim 15 where $W_5$ is —$CR_5$=.

18. A bicyclic amine of formula (XXX) according to claim 15 where $R_{2-1}$ and $R_{2-2}$ are taken together with the attached nitrogen atom to form 1-pyrrolidinyl, 1-piperazinyl, 1-thiomorpholinyl and 4-methylpiperazin-1-yl.

19. A bicyclic amine of formula (XXX) according to claim 18 where $R_{2-1}$ and $R_{2-2}$ are 1-pyrrolidinyl and 1-piperazinyl.

20. A bicyclic amine of formula (XXX) according to claim 15 where $R_{4-1}$ and $R_{4-2}$ are taken together with the attached nitrogen atom to form 1-pyrrolidinyl, 1-piperazinyl, 1-thiomorpholinyl and 4-methylpiperazin-1-yl.

21. A bicyclic amine of formula (XXX) according to claim 20 where $R_{4-1}$ and $R_{4-2}$ are 1-pyrrolidinyl and 1-piperazinyl.

22. A bicyclic amine of formula (XXX) according to claim 15 where $R_7$ is —H, —CH$_3$, -φ, 2-(1-morpholinyl)ethyl and 2-(1-piperazinyl)ethyl.

23. A bicyclic amine of formula (XXX) according to claim 15 where the pharmaceutically acceptable salts are salts of the following acids hydrochloric, hydrobromic, methanesulfonic, sulfuric, phosphoric, nitric, benzoic, citric, tartaric, fumaric, maleic, CH$_3$—(CH$_2$)$_n$—COOH where n is 0 thru 4, HOOC—(CH$_2$)n—COOH where n is as defined above.

24. A bicyclic amine of formula (XXX) according to claim 15 where the bicyclic amine (XXX) is selected from the group consisting of 5,6,7,8-tetrahydro-9-methyl-2,4-di-1-pyrrolidinyl-5H-pyrimido[4,5-b]indole, 9-methyl-2,4-di-1-pyrrolidinyl-9H-pyrimido[4,5-b]indole, 5,6,7,8-tetrahydro-2,4-di-1-pyrrolidinyl-1H-pyrimido[4,5-b]indole, 5,6,7,8-tetrahydro-9-[2-(1-piperazinyl)ethyl]-2,4-di-1-pyrrolidinyl-5H-pyrimido[4,5b]-indole.

25. Bicyclic heterocyclic amines selected from the group consisting of 5,6,7,8-tetrahydro-9-(2-hydroxyethyl)-2,4-di-1-pyrrolidinyl-5H-pyrimido[4,5-b]indole, 5,6,7,8-tetrahydro-9-[2-(1-piperidinyl)ethyl]-2,4-di-1-pyrrolidinyl-5H-pyrimido[4,5-b]indole, 2,6-di-1-pyrrolidinyl-4-[2-(4-morpholinyl)ethylamino]-pyrimidine, 6-(4-fluorophenyl)-7-(2-hydroxyethyl)-2,4-di-1-pyrrolidinyl-7H-pyrrolo[2,3-d]pyrimidine, 6-(4-fluorophenyl)-7-[2-(1-imidazolyl)ethyl]-2,4-di-1-pyrrolidinyl-7H-pyrrolo[2,3-d]pyrimidine, 6-(4-fluorophenyl)-7-[2-(4-morpholinyl)ethyl]-2,4-di-1-pyrrolidinyl-7H-pyrrolo[2,3-d]pyrimidine, pyrimidine, 6-(4-fluorophenyl)-7-[2-(1-tetrazolyl)ethyl]-2,4-di-1-pyrrolidinyl-7H-pyrrolo[2,3-d]pyrimidine, 6-(4-fluorophenyl)-7-[2-(1-(4-[4-fluorophenyl]piperazinyl)ethyl)]-2,4-di-1-pyrrolidinyl-7H-pyrrolo[2,3-d]pyrimidine and 6-(4-fluorophenyl)-5-methyl-7-[2-(1-morpholinyl)ethyl]-2,4-di-1-pyrrolidinyl-7H-pyrrolo[2,3-d]pyrimidine and pharmaceutically acceptable salts thereof.

* * * * *